(12) United States Patent
Stuart et al.

(10) Patent No.: US 9,089,661 B2
(45) Date of Patent: Jul. 28, 2015

(54) DOSE COUNTER

(71) Applicant: 3M INNOVATIVE PROPERTIES COMPANY, St. Paul, MN (US)

(72) Inventors: Adam J. Stuart, Loughborough (GB); Graham R. Purkins, West Sussex (GB); Rachel V. Striebig, London (GB); Stephen J. Howgill, Thurcaston (GB); Peter D. Hodson, Breaston (GB); Richard D. Brewer, Loughborough (GB); Benjamin J. Holden, Herts (GB)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 85 days.

(21) Appl. No.: 13/933,148

(22) Filed: Jul. 2, 2013

(65) Prior Publication Data
US 2013/0291861 A1 Nov. 7, 2013

Related U.S. Application Data

(62) Division of application No. 12/297,942, filed as application No. PCT/US2007/067056 on Apr. 20, 2007, now Pat. No. 8,479,732.

(60) Provisional application No. 60/745,326, filed on Apr. 21, 2006.

(51) Int. Cl.
*A61M 15/00* (2006.01)
*G06M 1/24* (2006.01)
(Continued)

(52) U.S. Cl.
CPC ......... *A61M 15/0065* (2013.01); *A61M 15/009* (2013.01); *A61M 15/0073* (2014.02);
(Continued)

(58) Field of Classification Search
CPC .......... A61M 15/009; A61M 15/0075; A61M 15/0065; A61M 15/0073; A61M 15/0068; A61M 11/00; A61M 15/00; A61M 15/0026; A61M 15/0043; A61M 15/0045; A61M 15/0051; A61M 15/0076; A61M 15/008; B65D 83/46; B65D 83/54; B65D 83/75; B65D 51/00; B65D 83/04; B65D 85/00; G06M 1/24; G06M 1/16; G06M 1/041; G06M 1/163; G06M 1/083; G06M 1/00; G06M 1/028; G06M 1/04; G06M 1/045; G06M 1/08; G06M 1/241; G06M 1/248; G06M 1/26; G06M 1/283; G06M 3/025; G06M 3/12; A01C 7/08; A01C 7/10; A01C 7/16; A61J 7/04; A61J 9/00; A61J 9/085; A62B 11/00; A62B 7/00; A62B 9/00; A62B 71/0672; A63F 1/18; B67D 5/08; B67D 5/22; B67D 5/26; B67D 7/22; B67D 7/26; G01D 7/00; G06C 3/00; G06F 17/00; G07F 11/00; G09F 11/23; G09F 11/24; G09F 9/00
USPC ............ 128/200.11–200.24, 203.12, 203.15, 128/205.23; 222/36, 38, 48, 162, 32, 33, 222/402, 402.11, 402.13, 13, 25–29, 18, 19, 222/42, 68; 116/285, 308, 35 A, 231–232, 116/242, 248, 255, 269, 293, 300, 309–320, 116/329; 604/58; 215/230; 206/459.1, 206/459.5
See application file for complete search history.

(56) References Cited

U.S. PATENT DOCUMENTS 3,402,692 A 9/1968 Hickman et al.
3,822,808 A 7/1974 Katakura et al.
(Continued)

FOREIGN PATENT DOCUMENTS

DE 10 2006 040 194 3/2008
EP 0 949 584 10/1999
(Continued)

*Primary Examiner* — Annette Dixon
(74) *Attorney, Agent, or Firm* — Colene H. Blank

(57) ABSTRACT

A dose counter for use in connection with a device adapted for metered dispensing of a medication is described. The dose counter has a first count indicator that has a first indicia bearing surface, with the first count indicator being rotatable about a first axis. The dose counter also has a second count indicator that has a second indicia bearing surface, with the second count indicator being rotatable about a second axis. The second axis is disposed at an obtuse angle with respect to the first axis, and the first and second indicia bearing surfaces align at a common viewing area to collectively present at least a portion of a medication dosage count.

17 Claims, 38 Drawing Sheets

(51) Int. Cl.
   *B65D 83/46* (2006.01)
   *B65D 83/54* (2006.01)
   *B65D 83/14* (2006.01)
   *G06M 1/16* (2006.01)

(52) U.S. Cl.
   CPC ........... *A61M15/0075* (2014.02); *B65D 83/46* (2013.01); *B65D 83/54* (2013.01); *B65D 83/75* (2013.01); *G06M 1/16* (2013.01); *G06M 1/24* (2013.01)

(56) References Cited

U.S. PATENT DOCUMENTS

| | | |
|---|---|---|
| 4,561,565 A | 12/1985 | Wolf et al. |
| 4,817,822 A | 4/1989 | Rand et al. |
| 5,289,946 A | 3/1994 | Fuchs |
| 5,564,414 A | 10/1996 | Walker et al. |
| 5,829,434 A | 11/1998 | Ambrosio et al. |
| 5,988,496 A | 11/1999 | Bruna |
| 6,142,339 A | 11/2000 | Blacker et al. |
| 6,161,724 A | 12/2000 | Blacker et al. |
| 6,182,655 B1 | 2/2001 | Keller et al. |
| 6,234,168 B1 | 5/2001 | Bruna |
| 6,283,365 B1 | 9/2001 | Bason |
| 6,360,739 B1 | 3/2002 | Rand et al. |
| 6,446,627 B1 | 9/2002 | Bowman et al. |
| 6,474,331 B1 | 11/2002 | Rand et al. |
| 6,659,307 B1 | 12/2003 | Stradella |
| 6,679,251 B1 | 1/2004 | Gallem et al. |
| 6,752,153 B1 | 6/2004 | Eckert |
| 6,938,796 B2 | 9/2005 | Blacker et al. |
| 6,997,349 B2 | 2/2006 | Blacker et al. |
| 7,100,530 B2 | 9/2006 | Lu |
| 7,137,391 B2 | 11/2006 | Bruna |
| 7,222,736 B1 | 5/2007 | Seijas |
| 7,322,352 B2 | 1/2008 | Minshull et al. |
| 7,404,373 B2 | 7/2008 | Bailey |
| 7,575,003 B2 | 8/2009 | Rasmussen et al. |
| 7,575,130 B2 | 8/2009 | Blacker et al. |
| 7,621,273 B2 | 11/2009 | Morton et al. |
| 7,726,555 B2 | 6/2010 | Minshull et al. |
| 7,766,188 B2 | 8/2010 | Pocock et al. |
| 7,780,038 B2 | 8/2010 | Ingram et al. |
| 7,984,826 B2 | 7/2011 | Blacker et al. |
| 8,020,507 B2 * | 9/2011 | Strong ............ 116/308 |
| 8,113,199 B2 | 2/2012 | Augustyn et al. |
| 8,814,035 B2 * | 8/2014 | Stuart ............ 235/87 R |
| 2002/0153005 A1 | 10/2002 | Scarrott et al. |
| 2004/0149772 A1 | 8/2004 | Ouyang |
| 2004/0179773 A1 | 9/2004 | Aksyuk et al. |
| 2004/0211420 A1 | 10/2004 | Minshull et al. |
| 2004/0255935 A1 | 12/2004 | Bruna |
| 2005/0011515 A1 | 1/2005 | Lee et al. |
| 2005/0041850 A1 | 2/2005 | Watkins et al. |
| 2005/0087191 A1 | 4/2005 | Morton et al. |
| 2005/0126469 A1 | 6/2005 | Lu |
| 2006/0060192 A1 | 3/2006 | Lu et al. |
| 2006/0086749 A1 | 4/2006 | Blacker et al. |
| 2007/0051745 A1 | 3/2007 | Poulard |
| 2008/0173669 A1 | 7/2008 | Pocock et al. |
| 2009/0173346 A1 | 7/2009 | Stuart et al. |

FOREIGN PATENT DOCUMENTS

| | | |
|---|---|---|
| EP | 1 047 467 | 11/2000 |
| EP | 1 169 245 | 1/2002 |
| EP | 1 542 750 | 6/2005 |
| EP | 1 680 065 | 7/2006 |
| EP | 1 758 631 | 3/2007 |
| EP | 1 787 668 | 5/2007 |
| EP | 2 108 395 | 10/2009 |
| FR | 2 665 557 | 2/1992 |
| FR | 2 854 878 | 11/2004 |
| GB | 2 348 928 | 10/2000 |
| GB | 2 414 187 | 11/2005 |
| GB | 2 448 838 | 10/2008 |
| GB | 2 448 839 | 10/2008 |
| JP | 2005-503897 | 2/2005 |
| JP | 2006-505374 | 2/2006 |
| WO | WO 93/03782 | 3/1993 |
| WO | WO 96/39337 | 12/1996 |
| WO | WO 98/41258 | 9/1998 |
| WO | WO 98/52634 | 11/1998 |
| WO | WO 99/36115 | 7/1999 |
| WO | WO 00/59806 | 10/2000 |
| WO | WO 01/31578 | 5/2001 |
| WO | WO 01/37909 | 5/2001 |
| WO | WO 04/001664 | 12/2003 |
| WO | WO 2004/012801 | 2/2004 |
| WO | WO 2004/026380 | 4/2004 |
| WO | WO 2004/041334 | 5/2004 |
| WO | WO 2005/041850 | 5/2005 |
| WO | WO 2005/060535 | 7/2005 |
| WO | WO 2005/079727 | 9/2005 |
| WO | WO 2005/111927 | 11/2005 |
| WO | WO 2005/113044 | 12/2005 |

* cited by examiner

DOSE COUNTER

CROSS REFERENCE TO RELATED APPLICATIONS

This application is a divisional of U.S. patent application Ser. No. 12/297,942, filed Apr. 20, 2007 (Oct. 21, 2008), now allowed, which is a national stage filing under 35 U.S.C. 371 of PCT/US2007/067056, filed Apr. 20, 2007, which claims priority to U.S. Priority Application No. 60/745,326, filed Apr. 21, 2006, the disclosure of which is incorporated by reference in their entirety herein.

TECHNICAL FIELD

The present invention relates to a dose counter for use in connection with a device adapted for metered dispensing of a medication.

BACKGROUND

Metered medication dose dispensers take many forms, but have in common that a predetermined dosage (i.e., amount) of medication is dispensed during a dosage dispensing operation. One common form of metered medication dose dispenser is known as an inhaler. Inhalers are commonly used for the treatment of asthma and other respiratory conditions.

An inhaler typically takes the form of an aerosol dispensing assembly having an aerosol container and an actuator housing for receiving that container. In the case of a pressurized inhaler, the container includes medication that is formulated with a suitable propellant that is filled into the container to define an aerosol canister. The container is typically equipped with a medication dispenser, fitted by means of a ferrule, such as a valve, in particular, a metered dose valve, comprising a valve stem movable between closed and discharge positions. Such a container with medication therein (i.e., an aerosol canister) and having a dispenser thereon, thus defines a medication vial. The medication vial is not refillable, and is disposed of once the medication therein has been dispensed. The medication vial is typically used in conjunction with an actuator housing (which may be reusable) that has a patient port (e.g., a mouthpiece or a port adapted for nasal use). The actuator housing typically comprises a support block that has a socket adapted to receive the valve stem of the valve on the container of the medication vial, and has an orifice in communication with the socket and the patient port. The canister and the support block are reciprocally movable relative to each other along an axis to allow the valve stem to move to its discharge position during the operation or firing of the assembly, thereby dispensing a dose of the medication from the vial. The actuator housing also typically includes an elongate portion extending opposite the support block and providing a chamber to house at least a portion of the container of the vial. There are many related design features of the actuator housing and the medication vial that are employed in order to achieve the desired medication dispensing performance (i.e., the dispensing of one metered amount or dose of sprayed medication of appropriate particle size distribution each time the aerosol dispensing assembly is actuated by a user).

To dispense a dose of medication, an inhaler user normally squeezes or pushes down on the inhaler in an axial direction causing a relative movement of the canister into the actuator housing towards the support block. It is useful for an inhaler user to know how many doses remain in his or her inhaler (i.e., how much medication by dosage is in the container of the aerosol dispensing assembly). To this end, a reliable dose counter device and methodology is desired, in order to register how many doses have been dispensed from an aerosol dispensing assembly and in order to inform a user how many more doses still remain to be dispensed.

There have been numerous proposals, such as in WO2005/060535 A2 and WO2004/041334, for dose counters to be used with inhalers (whether the inhaler is, for example, a dry powder inhaler, a portable nebulizer, or a pressurized metered dose inhaler, or some other type). However, despite progress, there is still an important need for dose counters which are both economic and reliable.

SUMMARY

It has been found that some dose counter designs may not reliably count a single dose only when a dose of medication has been dispensed. A count should not be triggered if the valve stem is not sufficiently depressed to fire the valve and it should not count more than one dose during a firing cycle (e.g., if the return cycle of the valve is interrupted). Also, some dose counters may not be sufficiently sturdy, and stable over the life of the product, so that it will work as intended and will not alter the count when the inhaler is subject to the rigors of being carried in a pocket, purse, school bag, etc. Further, some designs may have difficulty compensating for normal manufacturing variations in the product with which they are used (e.g., inhalers with tolerances that may result in a slightly different length of the valve stem and/or a slightly different length of travel of the valve stem before the valve is triggered). When a dose counter is integrated into the housing for an aerosol inhaler container, it is desirable to minimize its complexity and ease of installation, as well as to provide an arrangement which is as compact as possible, yet which provides a readily reliable and readable medication dosage count to a user.

In one aspect, the invention provides a dose counter for use in connection with a device adapted for metered dispensing of a medication. The dose counter comprises a first count indicator and a second count indicator. The first count indicator has a first indicia bearing surface, and is rotatable about a first axis. The second count indicator has a second indicia bearing surface, and is rotatable about a second axis. The second axis is disposed at an obtuse angle with respect to the first axis, and the first and second indicia bearing surfaces aligned at a common viewing area to collectively present at least a portion of a medication dosage count.

In one aspect, the present invention is a dose counter for use in connection with a device adapted for metered dispensing of a medication. The dose counter comprises a first count indicator and a second count indicator. The first count indicator has a first indicia bearing surface, and is rotatable about a first axis. The second count indicator has a second indicia bearing surface, and is rotatable about a second axis. The first and second axes are not disposed in coaxial, parallel or perpendicular alignments relative to each other. The first and second indicia bearing surfaces align at a common viewing area to collectively present at least a portion of a medication dosage count.

Surprisingly it has been found that by using first and second counter indicators rotatable about a first and second axis, respectively, where the first and second axes of the two counter indicators are not disposed in co-axial, parallel or perpendicular alignments relative to each other or by using a first count indicator disposed on an axis that is at an obtuse angle (in particular, an angle greater than 90° and less than 180°) with respect to the axis of the second count indicator it is possible to provide a desirable compact counter which can fit into the available space within the housing with no or only minimal modification (in shape and/or size) of the housing. Also at the same time the counter, due to its compact size, is less influential on the product performance, e.g. the airflow of the inhaler. Further it has been surprisingly found that through the display of separate digits or indicia in juxtaposition provides an advantageous ease in reading of the counter by user even though the counter itself is quite compact.

This is achieved without the need for a transfer gear to convey movements from one count indicator to another, since the count indicators intersect. Such intersection has allowed structures to be designed that interact periodically between them. Accordingly the counters herein described are desirably free of a transfer gear, which again allows for the provision of compact counters.

In another aspect, the present invention is a dose counter for use in connection with a device adapted for metered dispensing of a medication. The dose counter comprises a first count indicator and a second count indicator. The first count indicator is rotatable about an axis, and the first count indicator has a first indicia bearing surface that is a conical surface relative to the axis. Movement of one of the count indicators is initiated as a function of movement of the other count indicator. The first and second bearing surfaces align at a common viewing area to collectively present at least a portion of a medication dosage count.

The use of a first count indicator that is conical in shape facilitates the mounting of the respective counter in the curved profile, in particular within the "elbow" bend of a typical inhaler actuator, in a stable manner, while requiring minimal or no changes to the inside and/or outside profile and/or volume of the actuator to accommodate the counter.

The dependent claims define further embodiments of the invention.

The invention, in its various combinations, either in apparatus or method form, may also be characterized by the following listing of embodiments:

In one embodiment, a dose counter for use in connection with a device adapted for metered dispensing of a medication is described, the dose counter comprising:
  a first count indicator having a first indicia bearing surface, the first count indicator rotatable about a first axis; and
  a second count indicator having a second indicia bearing surface, the second count indicator rotatable about a second axis,
  wherein the second axis is disposed at an obtuse angle with respect to the first axis, and
  wherein the first and second indicia bearing surfaces align at a common viewing area to collectively present at least a portion of a medication dosage count.

In a further embodiment, the first bearing surface is a conical surface relative to the first axis.

In a further embodiment, the first and second indicia bearing surfaces are tangential at the common viewing area.

In a further embodiment, the first and second axes are disposed at an angle of 110 degrees to 160 degrees relative to each other.

In a further embodiment, the first and second axes are disposed at an angle of 125 degrees to 145 degrees relative to each other.

In a further embodiment, the common viewing area is generally tangential to a circumferential surface of a cylinder disposed about the second axis.

In a further embodiment, the dose counter further comprises:
  a rotation initiating element on the second count indicator; and
  a rotation following element on the first count indicator;
  wherein rotation of the second count indicator engages the rotation initiating element thereon with the rotation following element on the first count indicator to cause rotation of the first count indicator as a function of the extent of rotation of the second count indicator.

In a further embodiment, the dose counter further comprises:
  a rotation limiting element on the second count indicator; and
  a rotation following element on the first count indicator;
  wherein the rotation limiting element and the rotation following element engage at times during rotation of the second count indicator to prevent rotation of the first count indicator.

In a further embodiment, the second indicia bearing surface is a cylindrical surface relative to the second axis.

In a further embodiment, the viewing area is generally parallel with the second indicia bearing surface of the second count indicator.

In a further embodiment, the dose counter further comprises:
  a rotation initiating element on the first count indicator; and
  a rotation following element on the second count indicator;
  wherein rotation of the first count indicator engages the rotation initiating element thereon with the rotation following element on the second count indicator to cause rotation of the second count indicator as a function of the extent of rotation of the first count indicator.

In a further embodiment, the dose counter further comprises:
  a rotation limiting element on the first count indicator; and
  a rotation following element on the second count indicator;
  wherein the rotation limiting element and the rotation following element engage at times during rotation of the first count indicator to prevent rotation of the second count indicator.

In a further embodiment, the second indicia bearing surface is a surface extending perpendicular to the second axis.

In a further embodiment, the dose counter further comprises:
  a third count indicator having a third indicia bearing surface, the third count indicator rotatable about a third axis;
  wherein the third axis is disposed at an obtuse angle with respect to the first axis; and
  wherein the first and third indicia bearing surfaces align to collectively present a medication dosage count at the common viewing area, in combination with the second indicia bearing surface.

In a further embodiment, the first and third indicia bearing surfaces align tangentially at the common viewing area.

In a further embodiment, the second and third axes are disposed at a 90 degree angle relative to each other.

In a further embodiment, the first, second and third axes are coplanar.

In a further embodiment, the dose counter is provided, in combination with a metered-dose inhaler having a container filled with a medication.

In a further embodiment, the first axis and second axis are coplanar.

In a further embodiment, a dose counter for use in connection with a device adapted for metered dispensing of a medication is described, the dose counter comprising:
  a first count indicator rotatable about an axis, the first count indicator having a first indicia bearing surface that is a conical surface relative to the axis; and a second count indicator having a second indicia bearing surface;

wherein movement of one of the count indicators is initiated as a function of movement of the other count indicator, and wherein the first and second indicia bearing surfaces align at a common viewing area to collectively present at least a portion of a medication dosage count.

In a further embodiment, the first and second indicia bearing surfaces are tangential at the common viewing area.

In a further embodiment, a dose counter for use in connection with a device adapted for metered dispensing of a medication is described, the dose counter comprising:

a first count indicator having a first indicia bearing surface, the first count indicator rotatable about a first axis; and a second count indicator having a second indicia bearing surface, the second count indicator rotatable about a second axis;

wherein the first and second axes are not disposed in coaxial, parallel or perpendicular alignments relative to each other; and wherein the first and second indicia bearing surfaces align at a common viewing area to collectively present at least a portion of a medication dosage count.

In a further embodiment, the first and second indicia bearing surfaces are tangential at the common viewing area.

In a further embodiment, the first and second axes are coplanar.

This summary is not intended to describe each disclosed embodiment or every implementation of the present invention. Many other novel advantages, features, and relationships will become apparent as this description proceeds. The figures and the description that follow more particularly exemplify illustrative embodiments.

BRIEF DESCRIPTION OF THE DRAWINGS

The present invention will be further explained with reference to the attached figures, wherein like structure or system elements are referred to by like reference numerals throughout the several views.

While the above-identified figures set forth several embodiments of the present invention, other embodiments are also contemplated, as noted in the disclosure. In all cases, this disclosure presents the invention by way of representation and not limitation. It should be understood that numerous other modifications and embodiments can be devised by those skilled in the art which fall within the scope and spirit of the principles of this invention.

DETAILED DESCRIPTION

As noted above, the present invention is directed to a dose counter for use in connection with a dispensing assembly adapted for metered dispensing of a medication. In the description and illustrations herein, orientation references such as top, bottom, above, below, vertical, horizontal, upwardly, downwardly and the like are not intended to be limiting in nature, but only to provide visual references for the reader. It is understood that the dose counter will function whether operated as illustrated in an upright orientation as seen, for example, in FIGS. 1-3, or in an any other orientation (e.g., upside down).

Figure 1:
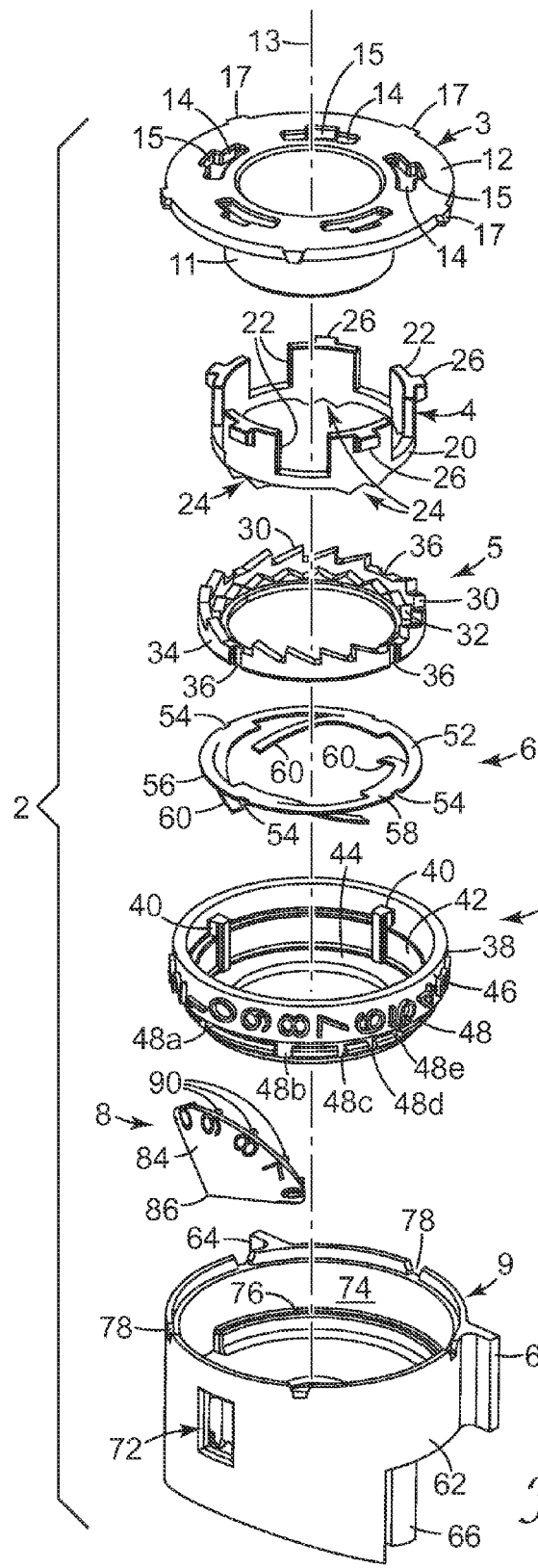
FIG. 1 represents an exploded isometric view of a first embodiment of a dose counter of the present invention.
Figure 2:
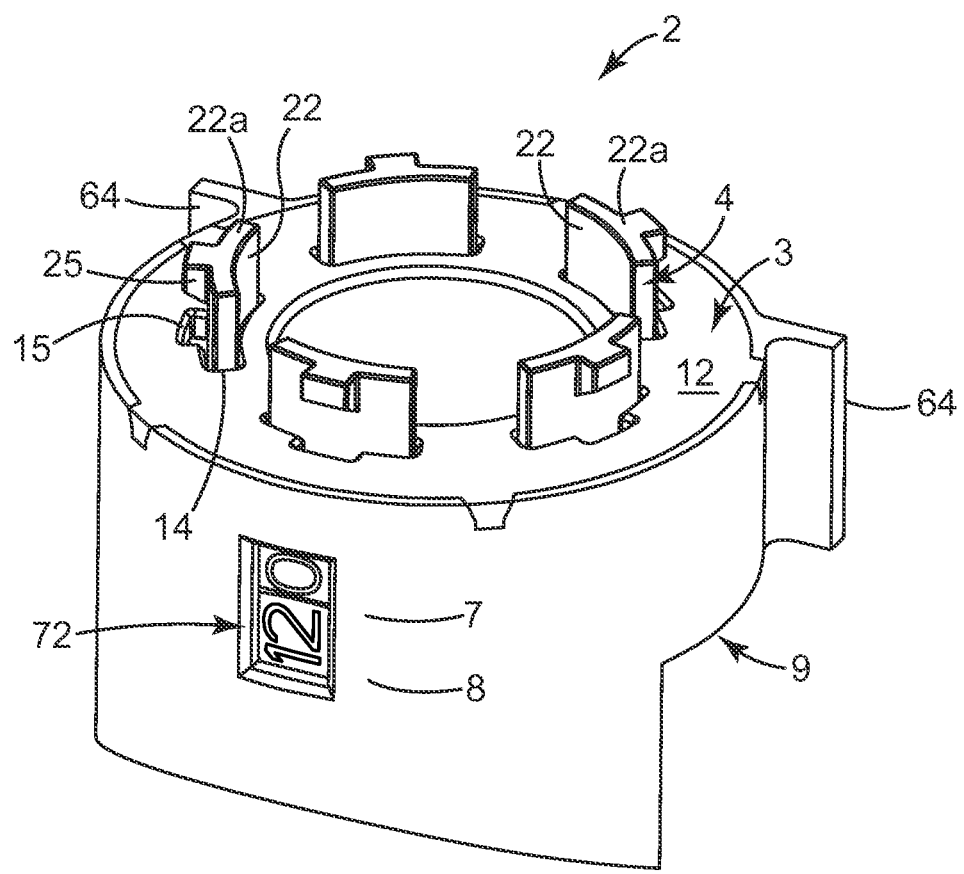
FIG. 2 represents an isometric assembled view of the dose counter of FIG. 1.
Figure 3:
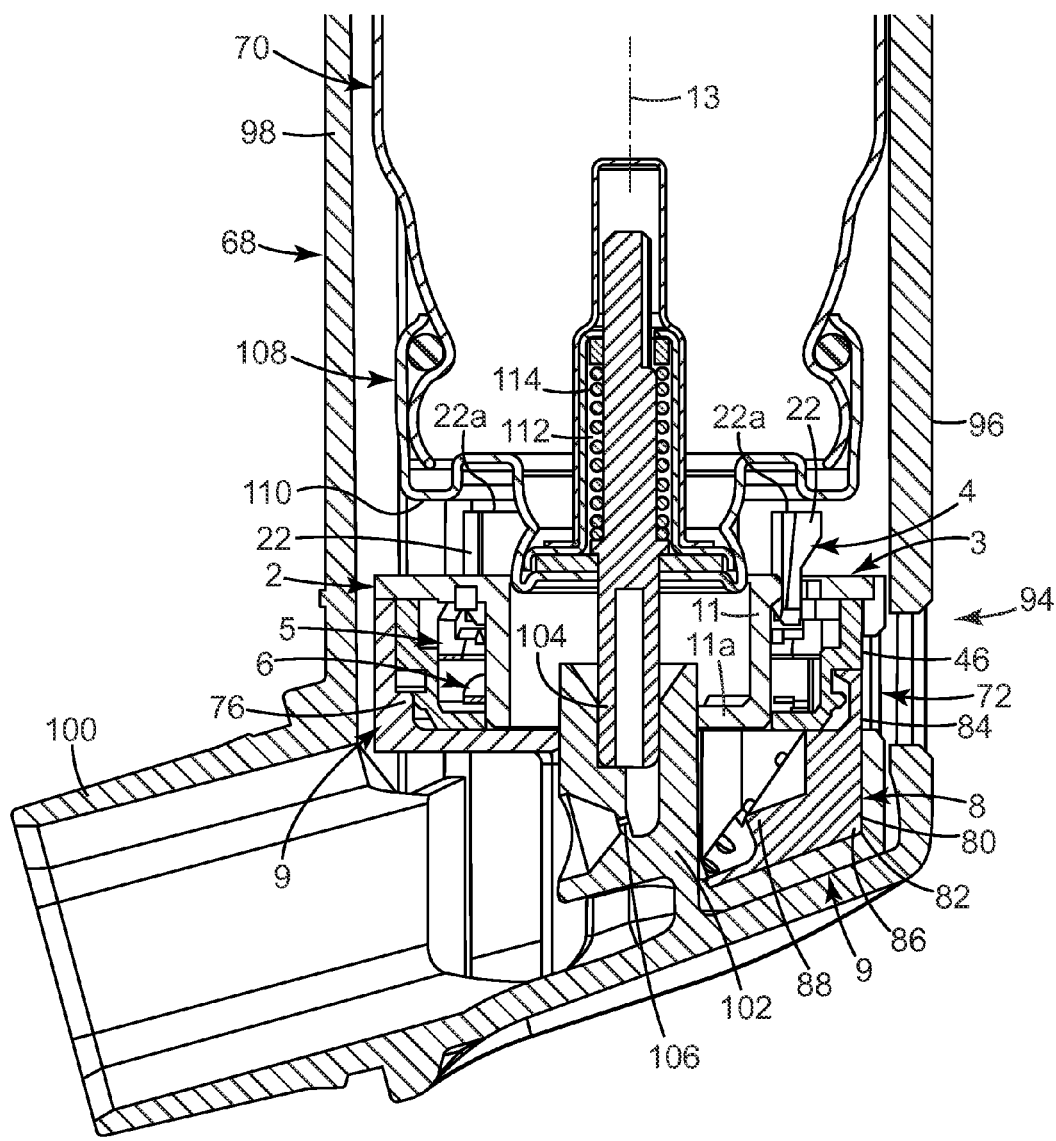
FIG. 3 represents a partial axial sectional view of a press-and-breathe inhaler incorporating the dose counter of FIGS. 1 and 2.
Figure 5:
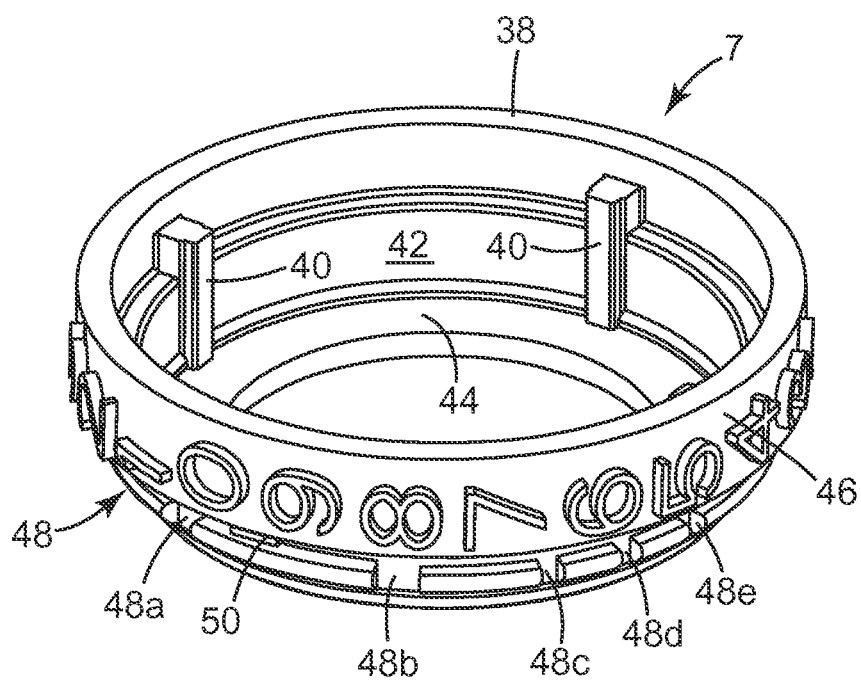
FIG. 5 represents an isometric view of a units rotational ring of the dose counter of FIGS. 1 and 2.
Figure 6:
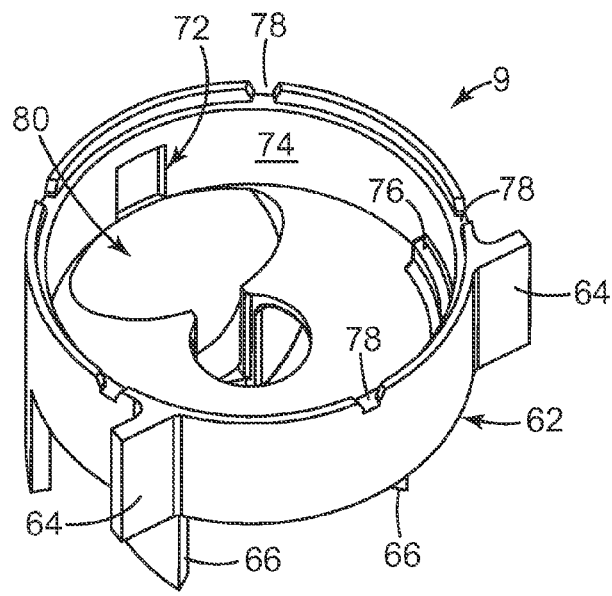
FIG. 6 represents an isometric view of a housing of the dose counter of FIGS. 1 and 2.
Figure 7:
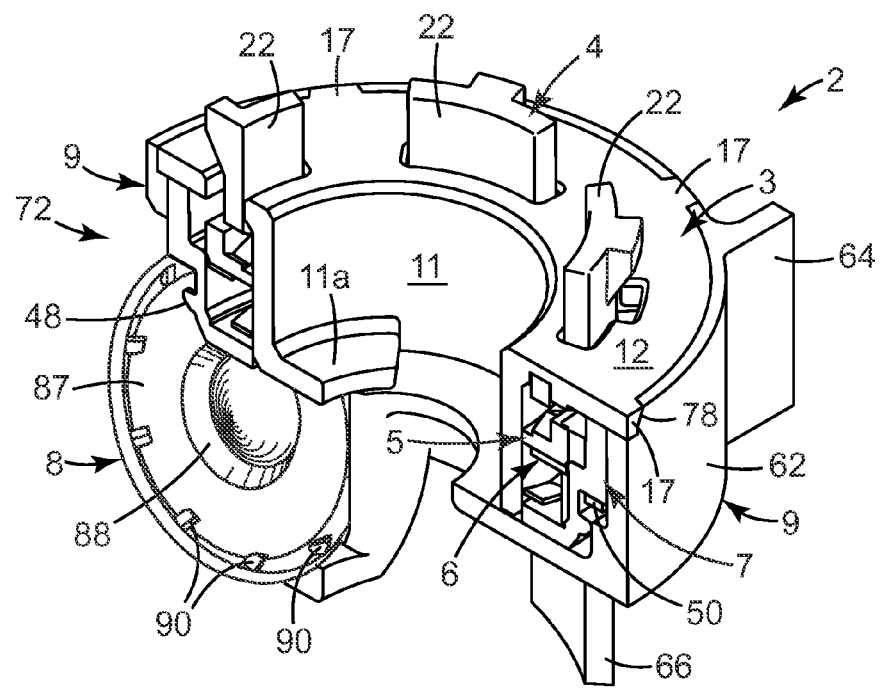
FIG. 7 represents an isometric sectional view of the assembled dose counter of FIGS. 1 and 2, with the lateral section taken through the viewing window thereof (and a tens cone not shown in section).

In a first embodiment illustrated in FIGS. 1-11, a dose counter 2 of the present invention includes a lid 3, an indexer 4, a units teeth ring 5, a compression spring 6, a units rotational ring 7, a tens cone 8 and a housing 9. Those components are assembled as illustrated in FIGS. 2, 3 and 7.

FIG. 1 represents an exploded view of a dose counter 2 of the present invention. The dose counter 2 comprises a units counter subassembly which counts individual doses in ones units as they are dispensed. In the embodiment illustrated in FIG. 1, the units counter subassembly includes all components shown except the tens cone 8. Alternative embodiments of the inventive dose counter 2 comprise additional counter components to count changes in tens units (and in some cases, changes in hundreds units) during the medication dosage counting process, as explained herein.

Figure 4:
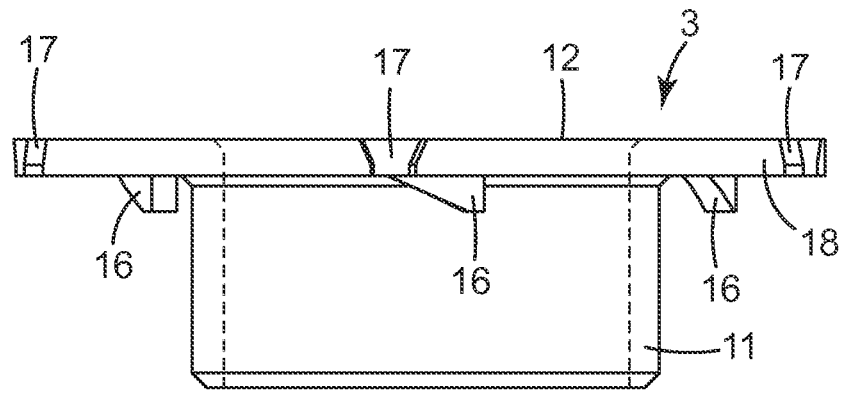
FIG. 4 represents a side view of a lid of the dose counter of FIGS. 1 and 2.

The lid 3 has an open cylindrical part 11 with a wide rim 12 at a top end thereof. The cylindrical part 11 has its axis aligned coaxially with an axis 13. A plurality (e.g., five) of equally spaced slots 14 extend through the rim 12, and each of the slots 14 has a curved portion disposed in an annular manner, coaxially with respect to the axis 13. Each slot 14 has a central slot projection 15 that extends radially outwardly from the curved portion of the slot 14. As illustrated in FIG. 4, a plurality (e.g., five) of ratchet members or teeth 16 project downwardly from a bottom surface of the rim 12, and are spaced circumferentially equally about the rim 12 relative to the axis 13. In one embodiment, the lid 3 has a plurality (e.g., five) of lugs 17 of trapezoidal cross-section on its outer rim 18, and the lugs 17 are formed to engage complementary slots on a top rim of the housing 9, as explained herein.

The indexer 4 is shaped like a castellated ring 20 that is coaxial with the axis 13. The ring has a plurality (e.g., five) of castellations 22 projecting upwardly therefrom. The castellations 22 are curved, like the curved portions of the slots 14. On a bottom side of the ring 20, a pair of downward sawtooth protrusions 24 is provided opposite each castellation 22. A protrusion 26 extends radially outward adjacent a top of each castellation 22, such that the lateral cross-section (relative to axis 13) of the top of each protrusion 26 and its respective castellation 22 corresponds closely to the shape of each of the curved slots 14 and each slot's respective central part 15. Accordingly, the castellations 22 can fit slidably through the slots 14 in the lid 12, in an axial direction.

A units teeth ring 5 is also coaxial with axis 13, and is provided with two rings of upstanding teeth. An outer ring of teeth 30 is disposed for engagement with ratchet members 16 on the bottom surface of the rim 12 of the lid 3. An inner ring of teeth 32 is arranged for engagement with the sawtooth protrusions 24 on the indexer 4. Units teeth ring 5 has an outer circumferential surface 34 that has a plurality (e.g., four) of axially aligned grooves 36 disposed therein. The interaction of the lid 3, indexer 4 and units teeth ring 5 is functionally similar to that disclosed in WO 2005/060535 A2, for causing the units teeth ring 5 to rotate about the axis 13 (i.e., to rotate the ring 5 an indexed amount as each dose of medication is dispensed). In WO 2005/060535 A2, count indicia were provided on an outer circumferential surface of the counter ring bearing the two rings of upstanding teeth. In the present case, however, no indicia are borne by the units teeth ring 5 itself. WO 2005/060535 A2 is hereby incorporated by reference herein.

The units rotational ring 7 is generally in the form of a hollow cylinder 38 that is coaxial with the axis 13. A plurality (e.g., four) of axially aligned ribs 40 extend radially inwardly from an internal surface 42 of the cylinder 38, terminating at a beveled ring 44 formed at the bottom of the cylinder 38. On an outer surface 46 of the cylinder 38, the units rotational ring 7 has a circumferential rim 48 extended thereabout adjacent the bottom of the cylinder 38. The circumferential rim 48 has a first set of missing arcuate segments or slots 48a, 48b, 48c, 48d and 48e, as seen in FIG. 1 (a second set of five missing arcuate segments or slots (not shown) are disposed 180 degrees around the other side of the units rotational ring 7 from the first set).

The units rotational ring 7 has, on its outer circumferential surface 46, indicia for indicating ones units dosage counts of medication being dispensed. As illustrated by FIG. 1, the indicia may take the form of digits from 9 to 0 arranged equally spaced twice about the circumference of the outer surface 46 of the cylinder 38. The digits are oriented so that they can be underlined by lines parallel to the axis 13, and the digits are arranged in two sequences of descending order in a clockwise direction when viewed from the bottom of the units rotational ring 7 (i.e., in the sequence: 9 8 7 6 5 4 3 2 1 0 9 8 7 6 5 4 3 2 1 0). As seen in FIGS. 5 and 7, the units rotational ring 7 has an oblong lug 50 spaced below and between each space between a 0 digit and its adjacent 9 digit. Since the digits 9 to 0 are arranged twice around the units rotational ring 7, there are two oblong lugs 50 thereon (on opposite sides of the ring 7).

The ribs 40 on the units rotational ring 7 are disposed to align with the grooves 36 on the units teeth ring 5. The outer circumferential surface 34 of the units teeth ring 5 is slightly smaller in diameter than the internal surface 42 of the cylinder 38, thus allowing axial movement of the units teeth ring 5 relative to the units rotational ring 7. However, while such axial movement is allowed, the interactions of the ribs 40 and respective grooves 36 couple the units teeth ring 5 and units rotational ring 7 for rotational purposes relative to the axis 13. As can be seen in FIG. 1, there are four teeth missing on the outer ring 30 where the grooves 36 are disposed, but this does not adversely affect the function of counting individual dosages of medication as they are dispensed.

The compression spring 6 is, in one embodiment, in the form of an annular leaf spring 52. The leaf spring 52 may be formed from a sheet of spring metal, although it may instead be formed of a suitable polymer material. The leaf spring 52 has a plurality (e.g., four) of cutouts 54 extending radially inwardly from an outer edge 56 thereof. Each of the cutouts 54 is formed and aligned to axially receive one of the ribs 40 of the units rotational ring 7 therein, thereby allowing axial movement of the compression spring 6 relative to the units rotational ring 7. The leaf spring 52 has an annular ring 58 with a plurality (e.g., four) of axially extending spring elements or leafs 60 thereon. The spring elements 60 are biased downwardly from the ring 58 for engagement with the top of the beveled ring 44 within the cylinder 38 of the units rotational ring 7. In one embodiment, the outer end of each leaf 60 is curved or otherwise formed to facilitate smooth sliding of the outer end with respect to the beveled ring 44. A top surface of the ring 58 of the leaf spring 52 engages a bottom surface of the units teeth ring 5. The leaf spring 52 thus urges the units teeth ring 5 axially away from the beveled ring 44 of the units rotational ring 7 and toward the sawtooth projections 24 on the indexer 4 and the ratchet members 16 on the bottom surface of the rim 12 of the lid 3. The leaf spring 52 may alternatively be assembled the other way up, so that the spring elements 60 are biased upwardly from the ring 58 for engagement with the bottom surface of the units teeth ring 5, while the other side of the leaf spring engages the top of the beveled ring 44. This alternative assembly may also be applied to other embodiments of the invention.

While ribs 40 and grooves 36 are shown, any suitable keyed feature between units teeth ring 5 and units rotational ring 7 will suffice to couple those two components together for rotation, yet allow relative axial movement. In one embodiment (not shown), rotation of the compression spring 6 relative to the units teeth ring 5 or units rotational ring 7 is permitted. However, to the extent it is desired that rotation of the compression spring 6 also be constrained with respect to the units teeth ring 5 or units rotational ring 7, while ribs 40 and cutouts 54 are shown for that purpose, any suitable keyed feature to accomplish that end will suffice.

The housing 9 has a generally cylindrical body 62, with two forward wings 64 projecting outwardly therefrom and two forward legs 66 extending downwardly therefrom (only one of which is shown in FIG. 1). The cylindrical body 62 and the wings 64 and the legs 66 are formed to mate with interior surfaces of an actuator housing 68 for an aerosol container 70 (see FIG. 3). A count viewing window 72 is provided in the cylindrical body 62. On an interior circumferential surface 74 of the cylindrical body 62, a ledge 76 is disposed for alignment with the units rotational ring 7, as seen in FIG. 3. The cylindrical body 62 has a top rim with a plurality (e.g., five) of slots 78 shaped for reception of the projections 17 on the lid 3 to provide a snap fit connection of the lid 3 and housing 9, or those components may be press fit together, or may be ultrasonically or otherwise (e.g., laser) welded together.

The housing 9 has a lower rear internal cone-shaped recess 80 designed to accommodate the tens cone 8 therein, as best seen in FIGS. 3 and 6. The tens cone 8 can thus rotate in a stable manner about an axis directed diagonally forward and upward from a rear corner 82 of the recess 80. In an alternative embodiment (not shown), the tens cone 8 protrudes partly from the housing 9, and is in part supported to rotate about an axis directed diagonally forward and upward from an inside of the actuator housing that receives the aerosol container.

Figure 8:
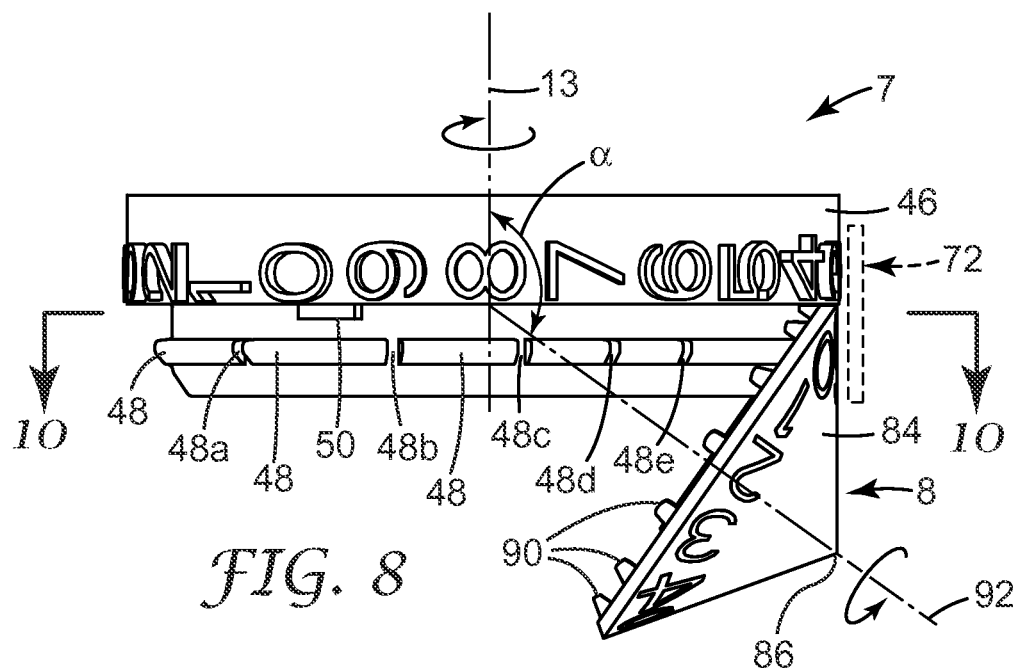
FIG. 8 represents a side view of the interface between the units rotational ring and the tens cone of the dose counter of FIGS. 1 and 2.
Figure 9:
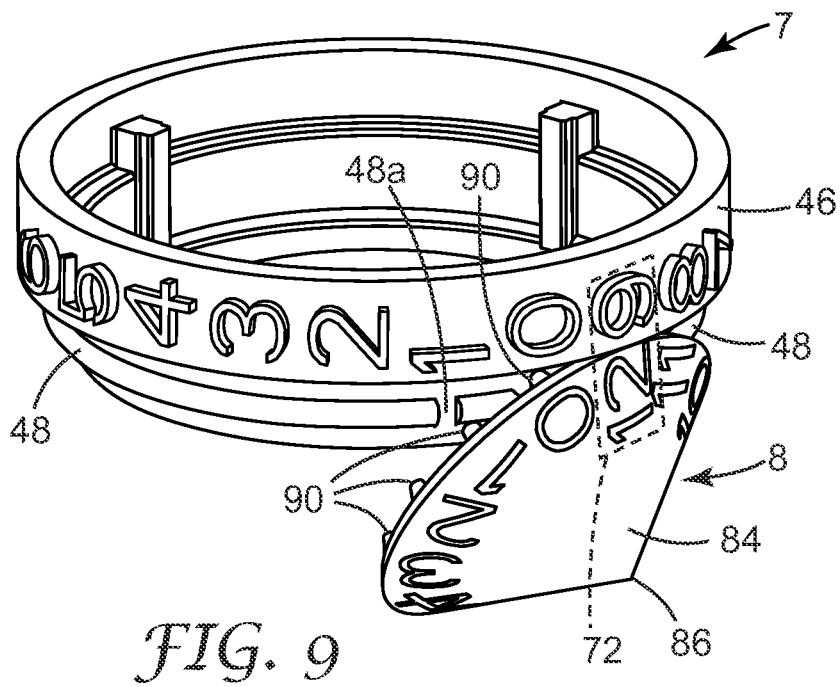
FIG. 9 represents an isometric view of the interface between the units rotational ring and the tens cone of FIG. 8, with the components each rotated to a different orientation relative to each other compared to the orientation shown in FIG. 8.

The tens cone 8 has numbers from 12 to 0 arranged descending clockwise about an external conical surface 84 of the tens cone 8 when viewed from its pointed end 86. The orientation of the numbers is such that they can be underlined by slanted lines from the apex of the conical surface 84 (e.g., in the sequence: 12 11 10 9 8 7 6 5 4 3 2 1 0). An internal surface 87 of the tens cone 8 has a raised frustum 88 pointing the opposite way from the conical surface 84, as can be seen in FIG. 7. Also on the internal surface 87 of the tens cone 8, an annular series of equally spaced pegs 90 extend parallel to and in the same direction as the frustum 88 (parallel to an axis 92 of rotation for the tens cone 8, as seen in FIG. 8). As further seen in FIG. 7, the cylindrical part 11 of the lid 3 has a lower arcuate shelf 11a that extends over the top of the cone shaped recess 80 of the housing 9 to inhibit the ingress of dust, fibers, fluff or other debris from going therein.

The dose counter 2 may be assembled by inserting the tens cone 8 into the housing 9, with the pointed end 86 of the conical surface 84 of the tens cone 8 seated in the rear corner 82 of the recess 80 in the housing 9. The circumferential rim 48 of the units rotational ring 7 has three slots 48c, 48d and 48e therein that correspond to positions of three of the pegs 90 on the tens cone 8, such that by correct orientation of the ring 7 and cone 8, the units rotational ring 7 can be seated on the ledge 76 of the housing 9, with three of the pegs 90 traversing the circumferential rim 48. The spring 6, units teeth ring 5, and indexer 4 can then be assembled in order over the units rotational ring 7, and the lid 3 fitted over the castellations 22 of the indexer 4 and then engaged with the housing 9. This complete assembly thus defines the dose counter 2, as seen in FIG. 2. Once assembled, the internal working components of the dose counter 2 are fairly well enclosed by the housing 9 and lid 3, thus inhibiting the ingress of dust, fibers, fluff and other debris therein to protect those working components. The enclosure of the working components of the dose counter 2 (with the lid 3 engaged to the housing 9) also provides an assembly that is somewhat tamper resistant, and is durable and shock-resistant.

FIG. 3 shows a vertical cross-sectional view through part of a press-and-breathe aerosol inhaler incorporating the dose counter 2 of FIGS. 1 and 2. The purpose of the dose counter is to provide a display that indicates the number of doses of medication remaining or (in an alternative embodiment, not shown) the number already dispensed. The indicia provided for review by a user may be suitable alphabetic, numeric, alphanumeric, or color symbols, or any combination thereof, providing a sequential count up or count down of dispensed doses, or providing a more general indication such as "full" or "empty". The indicia would be visible through a window 94 in a side wall 96 of the actuator housing 68; alternatively, the side wall 96 may be transparent or have at least a portion thereof made of a transparent material to provide a viewing area or lens for viewing the indicia and count. The press-and-breathe inhaler comprises the actuator housing 68 having a cylindrical body 98 to accommodate the aerosol container 70. The actuator housing 68 has a mouthpiece 100. A nozzle block 102 is positioned within the actuator housing 68 and has an aperture to accommodate a valve stem 104 of the aerosol container 70 and a spray orifice 106. A metering valve 108 of the aerosol container 70 comprises a valve ferrule 110, valve stem 104, metering chamber 112 and return spring 114. As illustrated in FIG. 3, the aerosol container 70 is also aligned coaxially with the axis 13.

The housing 9 is designed to minimize interference and obstruction of the medication spray and airflow paths in the actuator housing 68. In one embodiment, the dose counter 2 is clipped or retained within the actuator housing 68 by suitable detents or other engaging structure (not shown) between the actuator housing 68 and the dose counter 2. In addition, the dose counter 2 is designed to be useable with a variety of metering valve designs, and to fit compactly within commercially available actuator housing profiles so that it is not necessary to change the external configuration of those actuator housings to accommodate the inventive dose counter 2 therein. The FIGS. illustrate the dose counter 2 of the present invention in combination with an actuator housing for an inhaler of the type used for dispensing medication from a pressurized aerosol container (a pressurized metered dose inhaler or pMDI). However, inhalers in other forms may be used with the present invention including, for example, dry powder inhalers, portable nebulizers, and other metered dose dispensers that use reciprocal mechanism.

The inhaler is actuated to dispense a dosage of medication by pressing down on the aerosol container 70 relative to the actuator housing 68. When the inhaler is actuated, downward movement of the aerosol container 70 causes the valve ferrule 110 to engage top surfaces 22a of the castellations 22 of the indexer 4. The lid 3 is positioned low enough relative to the valve ferrule 110 so that those components never engage each other, thus ensuring sufficient space to allow adequate metering valve travel to guarantee the dispensing of a dose of medication. Engagement with the valve ferrule 100 causes the indexer 4 to move downwardly relative to the lid 3, and the sawtooth protrusions 24 of the indexer 4 engage teeth of the inner ring of teeth 32 of the units teeth ring 5. Once the outer ring of teeth 30 move low enough to clear the ratchet members 16 on the lid 3, the ring 5 rotates (as described in WO 2005/060535 A2). Such rotational movement results in coupled rotational movement of the units rotational ring 7. The compression spring 6 between the units rotational ring 7 and the units teeth ring 5 maintains relative engagement of the sawtooth protrusions 24 and inner ring of teeth 32 until the downward actuation force on the aerosol container 70 is removed, and the return spring 114 separates the valve ferrule 110 from the indexer 4. This allows the compression spring 6 to return the indexer 4 upwards, whereupon the interaction of the outer ring of teeth 30 on the units teeth ring 5 with the ratchet members 16 on the lid 3 results in further rotational motion of the units teeth ring 5 together with further coupled rotational motion of the units rotational ring 7, thereby completing the ones units change to the count, corresponding to the actuation and corresponding to a single dosage of medication. The dose counter 2 is designed to count at (or close before) the firing point of the metering valve 108 on the aerosol container 70, and then "lose" any subsequent excessive axial travel (i.e., lost "motion") of the axially moving components of the dose counter 2. Thus, for each actuation of the inhaler, the units rotational ring 7 is indexed to move rotationally one count increment, which will change the ones units count visible via the windows 72 and 94.

In order to change the tens units that are displayed via the windows 72 and 94, the tens cone 8 is rotated as a function of the rotation of the units rotational ring 7 to move the number bearing portion of the conical surface 84 past the window 72. The axes 13 and 92 of the units rotational ring 7 and tens cone 8 are, as shown in FIG. 8, disposed at an obtuse angle $\alpha$ relative to each other (i.e., disposed at an angle greater than 90 degrees and less than 180 degrees relative to each other). In one embodiment, the angle $\alpha$ ranges from 110 degrees to 160 degrees. In an alternative embodiment, the angle $\alpha$ ranges from 125 degrees to 145 degrees. In yet another embodiment, the angle $\alpha$ is 135 degrees. In one embodiment, the axes 13 and 92 are coplanar, but not coaxial, parallel or perpendicular relative to each other.

As seen in FIGS. 3 and 7, portions of the tens cone 8 and units rotational ring 7 converge adjacent the viewing window 72 of the housing 9. At the viewing window 72, a circumferential segment of the outer surface 46 of the units rotational ring 7 that bears ones units indicia and an arcuate segment of the conical surface 84 that bears tens units indicia are aligned to collectively present at least a portion of a medication dosage count (for example, in FIG. 2, the count "120" is seen, and in FIG. 9, the count "129" is seen). At this juxtaposition of the indicia bearing surfaces of the units rotational ring 7 and the tens cone 8, those surfaces are tangential to each other at the viewing window 72, which provides a common view area for observing the indicia on the two separate indicia bearing surfaces. As noted above, when the dose counter 2 is disposed within the actuator housing 68 (see FIG. 3), the viewing window 72 is aligned with the viewing window 94 in the side wall 96 of the actuator housing 68, thus presenting the common viewing area for observation by a user. In one embodiment, the common viewing area is generally tangential to a circumferential surface of a cylinder disposed about the axis 13 (see FIG. 8).

Every tenth movement of the units rotational ring 7 results in a movement of the tens cone 8 due to interaction between one of the oblong lugs 50 (on the units rotational ring 7) and one of the pegs 90 (on the tens cone 8). The relationship between the lugs 50 and pegs 90 is illustrated schematically in FIGS. 10A-10D and FIGS. 11A-11D. This direct interaction between the units rotational ring 7 and the tens cone 8 eliminates the need for any transfer gear or other motion translation components between a component bearing ones units indicia (i.e., the units rotational ring 7) and a component bearing tens units indicia (i.e., the tens cone 8). This arrangement requires fewer parts, is more economical in function and is more compact. In addition, the use of fewer components in a dose counter reduces the number of components that must be manufactured within certain tolerance ranges, and thus reduces the possibility of component incompatibility or inoperabilities due to tolerance stack-up.

Figure 10A:
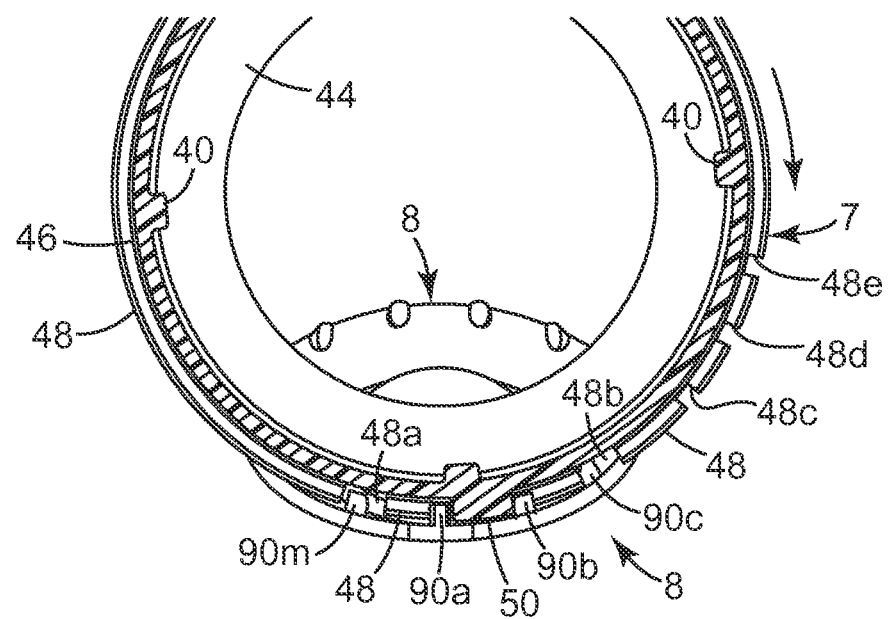
FIGS. 10A, 10B, 10C and 10D represent sectional views as taken generally along line 10-10 in FIG. 8, illustrating rotation of the tens cone as a function of rotation of the units rotational ring.
Figure 10B:
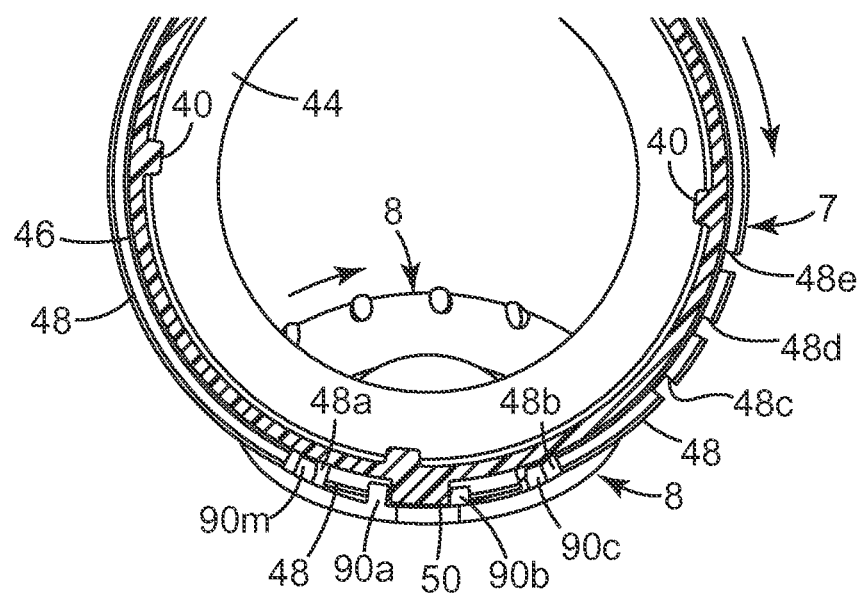
Figure 10C:
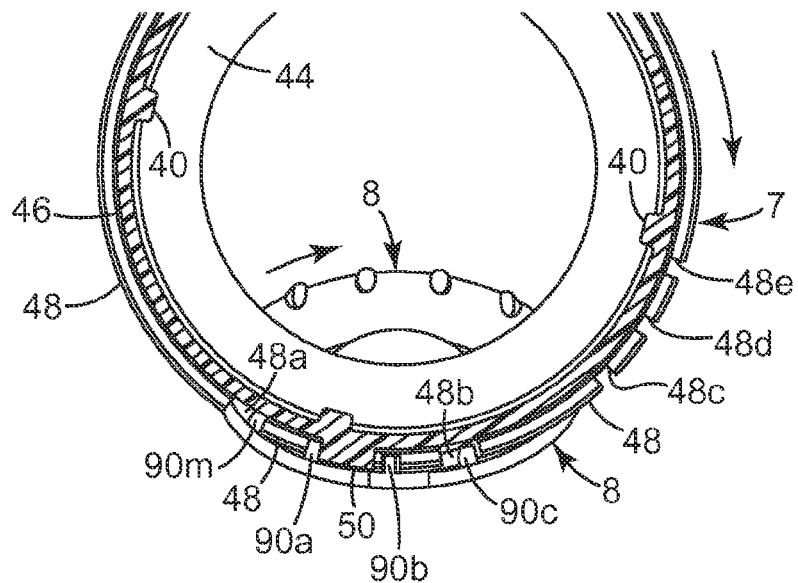
Figure 10D:
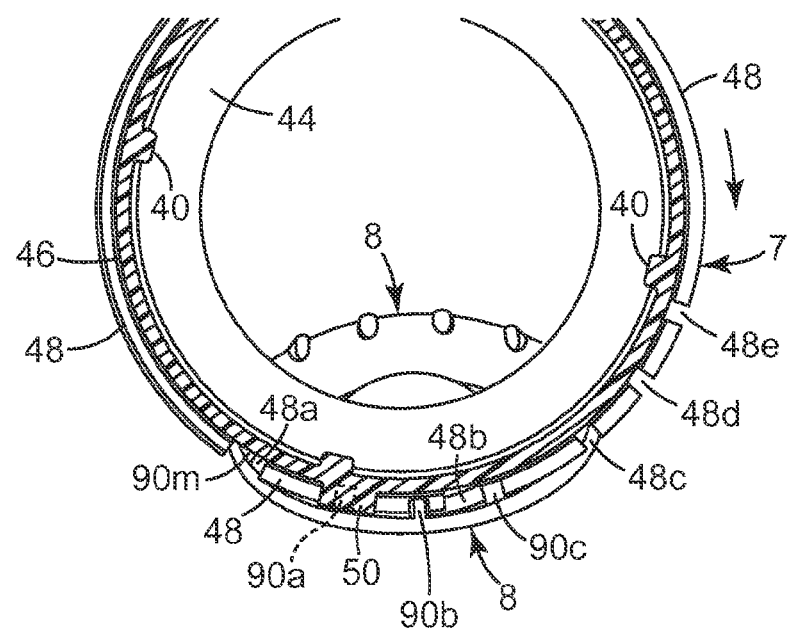
Figure 11A:
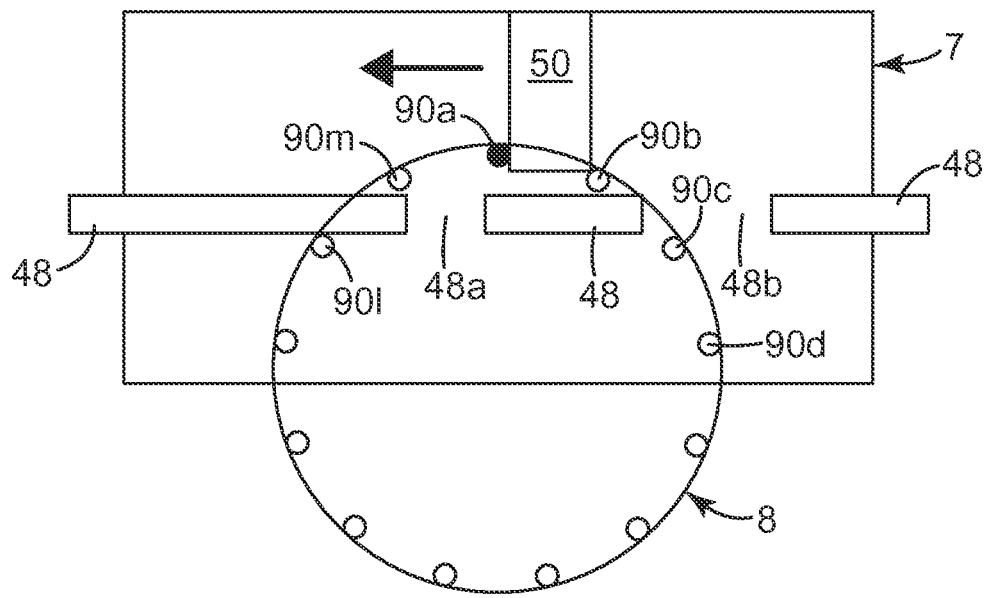
FIGS. 11A, 11B, 11C and 11D represent schematically the interface between the units rotational ring and tens cone that facilitates rotation of the tens cone as a function of rotation of the units rotational ring.
Figure 11B:
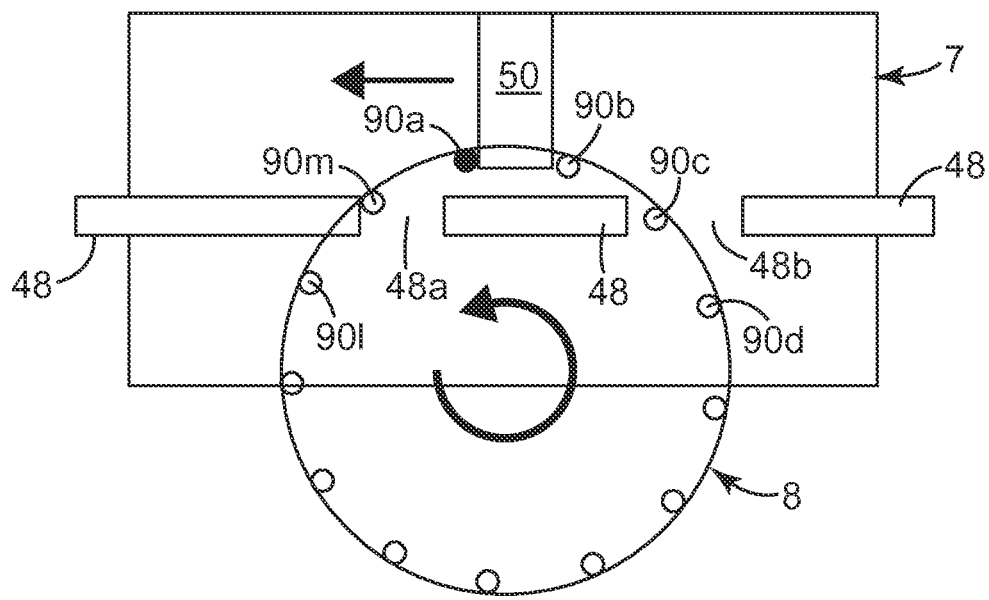
Figure 11C:
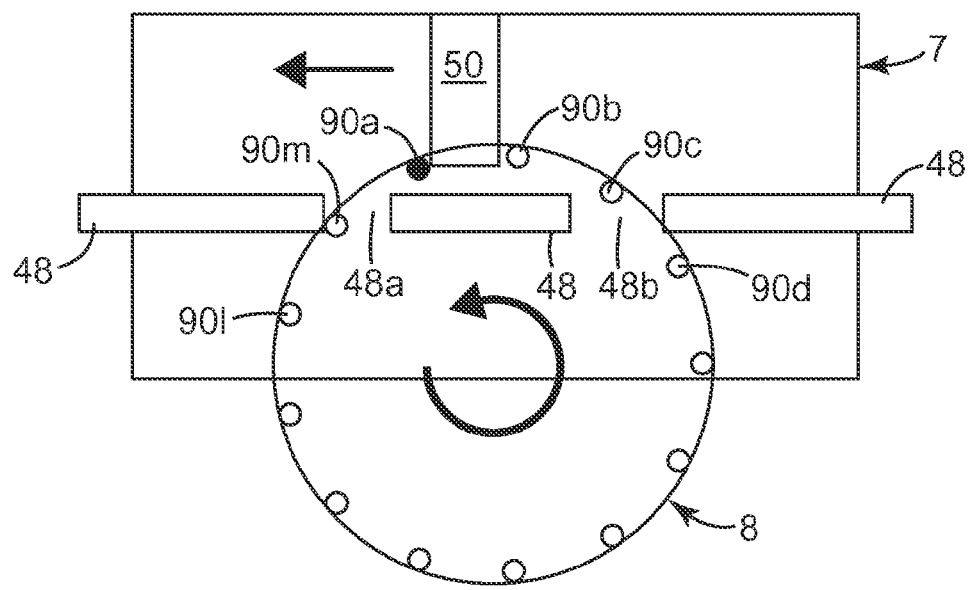
Figure 11D:
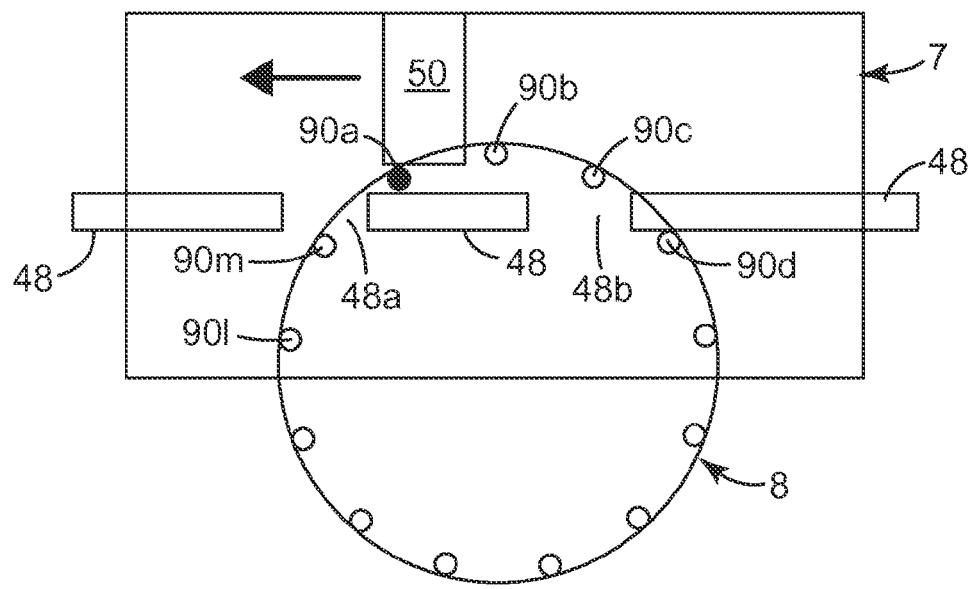
Figure 12:
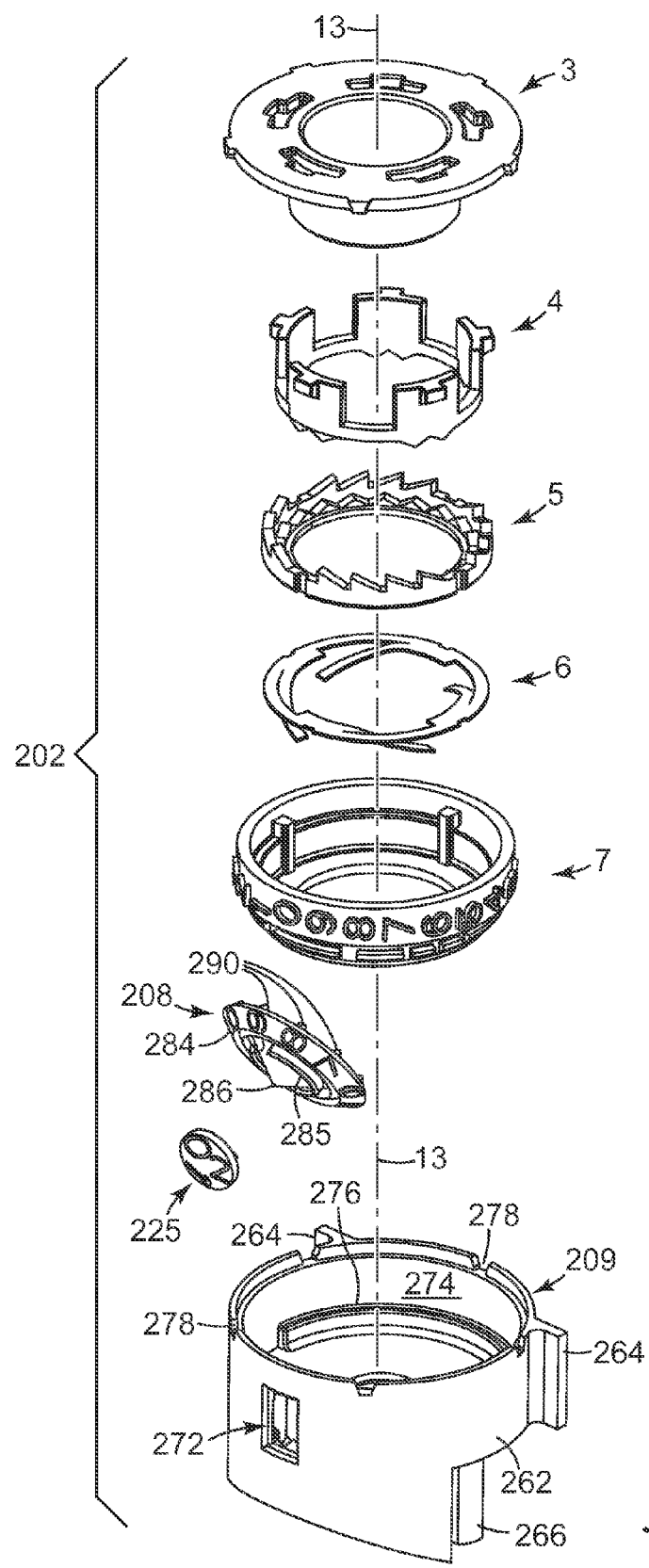
FIG. 12 represents an exploded isometric view of a second embodiment of the dose counter of the present invention.
Figure 13:
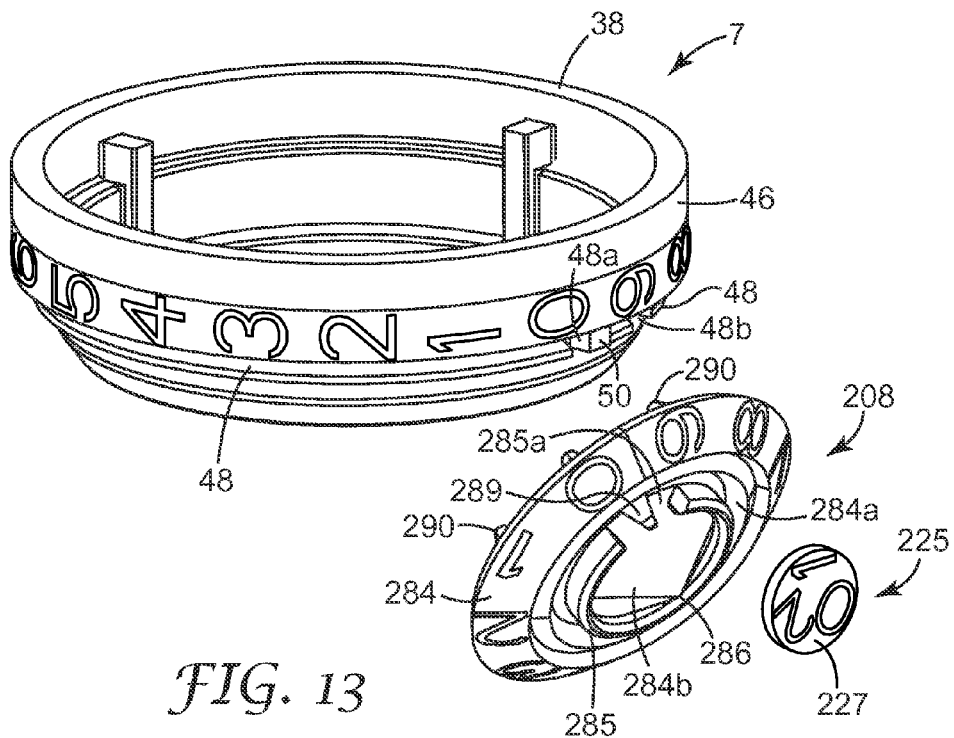
FIG. 13 represents an exploded isometric view of the indicia display components of the dose counter of FIG. 12 (i.e., a units rotational ring, a tens cone and a hundreds disk).
Figure 14:
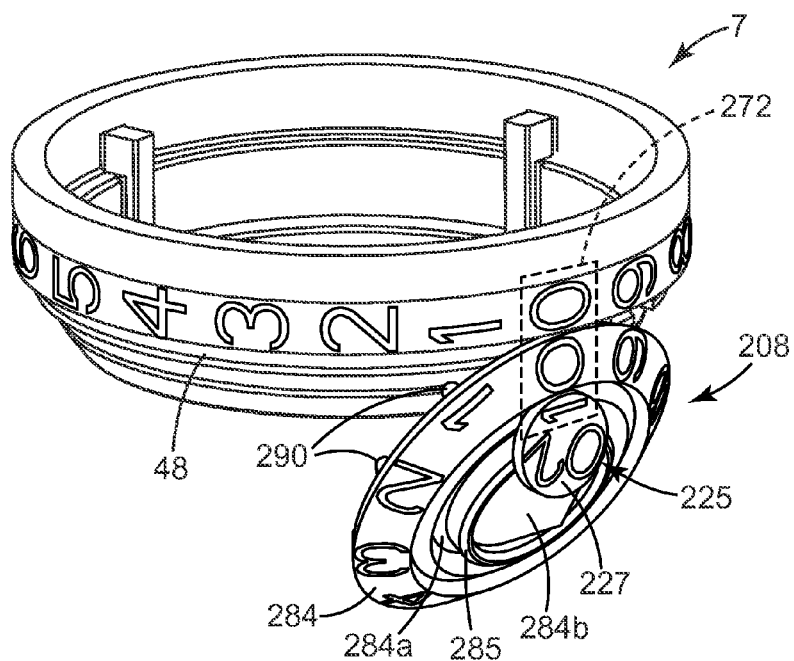
FIG. 14 represents an isometric assembled view of the indicia display components of FIG. 13.

The interaction in sequence for causing the tens cone 8 to change the indicia displayed in viewing window 72 involves engagement of one of the lugs 50 on the units rotational ring 7 with one of the pegs 90 on the tens cone 8. As seen in FIG. 10A, as the units rotational ring 7 rotates clockwise, one of the lugs 50 thereon eventually moves into engagement with the peg 90a on the tens cone 8. FIG. 11A illustrates the relationship of the lug 50 and peg 90a at the time of their initial engagement caused by rotation of the units rotational ring 7 relative to the tens cone 8. As the units rotational ring 7 continues its clockwise rotation, as seen in FIG. 10B, the lug 50 pushes the peg 90a to the left as viewed in FIG. 10B, thereby causing the tens cone 8 to rotate about its axis as further illustrated in FIG. 11B in a counterclockwise manner. As shown in FIG. 10C, continued clockwise rotation of the units rotational ring 7 causes the lug 50 to further push the peg 90a to the left (as viewed in FIGS. 10C and 11C), thereby causing further rotation of the tens cone 8 in a counterclockwise manner about its axis. Eventually, as illustrated in FIGS. 10D and 11D, the lug 50 pushes the peg 90a so far that rotation of the tens cone 8 moves the peg 90a out of the path of the advancing lug 50 (i.e., below the lug 50 as seen in FIG. 11D). Once this happens, further counterclockwise rotational movement of the tens cone 8 stops, and a new tens units number is aligned for observation through the viewing window 72. In an embodiment where the tens units number is rotated to show a countdown of the number of dosages remaining, the new tens units number displayed will be a number smaller than the previous number that was displayed.

Rotation of the tens cone 8 relative to the rotation of the units rotational ring 7 occurs each time one of the lugs 50 engages one of the pegs 90. In one embodiment, there are two lugs on the units rotational ring 7, so for every complete rotation of the units rotational ring 7 (which represents twenty ones units numbers), the tens cone 8 is rotated through two tens units numbers. In alternative embodiments, the rotation of the tens cone 8 as a function of rotation of the units rotational ring 7 may be made more frequent or less frequent by providing more or less lugs 50 on the units rotational ring 7. In the illustrated embodiment, the conical surface 84 of the tens cone 8 has thirteen tens units number bearing arcuate segments, and on its internal surface 87 the tens cone 8 correspondingly has thirteen pegs 90. If more or fewer number segments are desired to be provided on the tens cone 8, the number of pegs 90 must therefore accordingly be adjusted in a likewise fashion.

In FIGS. 10 and 11, the pegs on the tens cone 8 are referenced as pegs 90a, 90b, 90c, etc. As noted above, the outer surface 46 of the units rotational ring 7 has the circumferential rim 48 thereon, which has slots 48a and 48b aligned adjacent each lug 50 to allow movement of pegs 90, as can be seen in the sequential illustrations of FIGS. 10 and 11. Thus, as peg 90a is moved by lug 50, peg 90c moves through slot 48b in circumferential ring 48 (from below the slot 48b as seen in FIG. 11A to above the slot 48b as seen in FIG. 11D). Likewise, peg 90m moves through slot 48a as the tens cone 8 is rotated (from above the circumferential rim 48 as seen in FIG. 11A to below the circumferential rim 48 as seen in FIG. 11D).

The circumferential rim 48 acts to prevent rotation of the tens cone 8 except when one of the lugs 50 engages one of the pegs 90. For example, as seen in FIG. 11A, tens cone 8 is constrained from movement about its axis by the circumferential rim 48 extending between the pegs 90m and 90l. While movement of the tens cone 8 is allowed when the units rotational ring 7 and tens cone 8 are aligned as seen in FIGS. 10B and 10C (and in FIGS. 11B and 11C), the tens cone 8 is again prevented from movement once in the configuration shown in FIG. 11D. In the position shown in FIG. 11D, the circumferential rim 48 extends between the pegs 90a and 90d, and with further rotation of the units rotational ring 7, the circumferential rim 48 will extend between adjacent pegs 90a and 90m, and between adjacent pegs 90c and 90d. Thus, once the tens cone 8 has been moved by interaction with one of the lugs 50 on the units rotational ring 7, it cannot rotate again until another lug 50 presents itself for engagement with the peg 90b on the tens cone 8, even though the units rotational ring 7 is rotating about its axis 13 to display differing ones units digits. In one embodiment, cooperative features are provided between the housing 9 and tens cone 8 that will, when the tens cone 8 has been rotated to a position that shows a tens units 0 numeral in the view window 72, prevent further rotation of the tens cone 8. The units rotational ring 7 can continue to rotate as it counts down its nine remaining ones units counts, and then it would be prevented from further rotation by the tens cone 8. At this point, the viewing window would display a zero count for the dose counter 2. To the extent further medication is present in the aerosol container, it may be dispensed by a user using the aerosol dispensing assembly, but the dose counter 2 will not register any further dosage counts. As an alternative, the aerosol dispensing assembly could be designed to cease dispensing doses of medication once the zero count has been reached, for example by limiting the free movement of the indexer 4.

In essence, the inventive dose counter in the embodiment illustrated in FIGS. 1-11 operates in the following fashion. When a user actuates the inhaler by pushing the aerosol container 70 downwardly into the actuator housing 68, the valve ferrule 110 engages the indexer 4 to push it downwardly. Indexer 4 engages and then causes rotation of units teeth ring 5. The units rotational ring 7 is coupled rotationally to the units teeth ring 5, so it rotates as well. As the aerosol container 70 reciprocates down and up to complete a single dosage of medication therein, the indexer 4 and units teeth ring 5 also reciprocate down and up relative to the units rotational ring 7. One complete down and up reciprocal movement of the units teeth ring 5 causes the units rotational ring 7 to rotate on its axis 13 a single ones units count change in position thereof. Rotation of the units rotational ring 7 is translated into rotation of the tens cone 8 by engagement of the lug 50 on the units rotational ring 7 with one of the pegs 90 on the tens cone 8. However, the tens cone 8 is only rotated periodically relative to the units rotational ring 7, to indicate a change in decade of the counts (i.e., the tens cone 8 is only moved once for every ten movements of the units rotational ring 7). Each time the units rotational ring 7 counts ten ones units counts, the tens cone 8 is indexed one position to change the tens units count displayed thereon.

In the illustrated embodiment, a maximum dosage count of "129" medication dosages is shown. This allows for some testing of the aerosol dispensing assembly (e.g., 9 initial "tester" counts available), with 120 user available dispensing counts remaining. As noted above, changing the frequency or spacing of indicia on the units rotational ring and/or tens cone (along with corresponding changes in the interactive geometry between those components) allows modification of the possible count indicia shown.

One reason to alter the dosage count indicia would be where a single prescribed dose for a product requires two actuations of the inhaler. In this system, the possibility of counting 240 actuations is achieved by the following modifications. The units rotational ring would have only one oblong lug 50 (not 2) and similarly, only one set of slots 48a and 48b in the circumferential rim 48 (not 2 slots). The indicia on the units rotational ring 7 would be disposed in the following order about its circumference: 9*8*7*6*5*4*3*2*1*0* (or with "½" in place of each asterisk) rather than the 9 8 7 6 5 4 3 2 1 0 9 8 7 6 5 4 3 2 1 0 indicia pattern described above. The tens cone 8 would then be moved after every twenty actuations (ten dosages) of the units rotational ring 7, rather than after every ten actuations thereof. This would allow the inventive dosage counter to achieve 240 actuation events, rather than have it limited to 120.

While the embodiment of the inventive dose counter illustrated in FIGS. 1-11 allows an indicia display changing in ones units and in tens units, it does not allow a change in display of hundreds units. FIGS. 12-20 illustrate a dose counter 202 of the present invention which provides a user with a possible dosage count ranging from 0 to 299. The dose counter 202 is similar to the dose counter 2 of FIGS. 1-11, but includes a modified tens cone 208, a modified housing 209 and a hundreds disk 225. The other components of the dose counter 202 are essentially the same as those set forth for dose counter 2. For instance, the lid 3, indexer 4, units teeth ring 5, compression spring 6 and units rotational ring 7 are essentially the same, and operate the same as previously described. The interaction of the lid 3, indexer 4 and units teeth ring 5 is functionally similar to that disclosed in WO 2005/060535 A2, for causing the units teeth ring 5 to rotate about the axis 13 (i.e., to rotate the ring 5 an indexed amount as each dose of medication is dispensed). The interaction between the units rotational ring 7 and tens cone 208 is also similar in terms of causing rotation of the tens cone 208 about its axis as a function of rotation of the units rotational ring 7.

Figure 18:
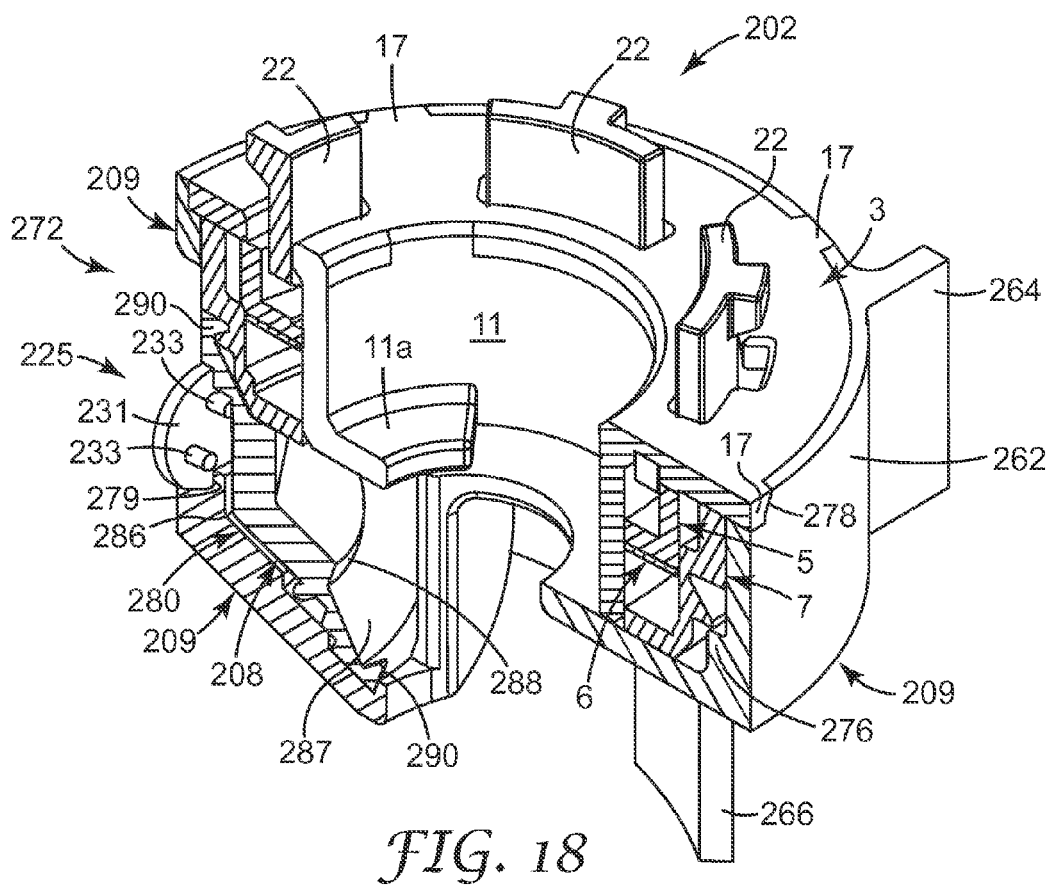
FIG. 18 represents an isometric sectional view of the assembled dose counter of FIGS. 12 and 15, with the lateral section taken through the viewing window thereof (and the hundreds disk not shown in section).
Figure 19:
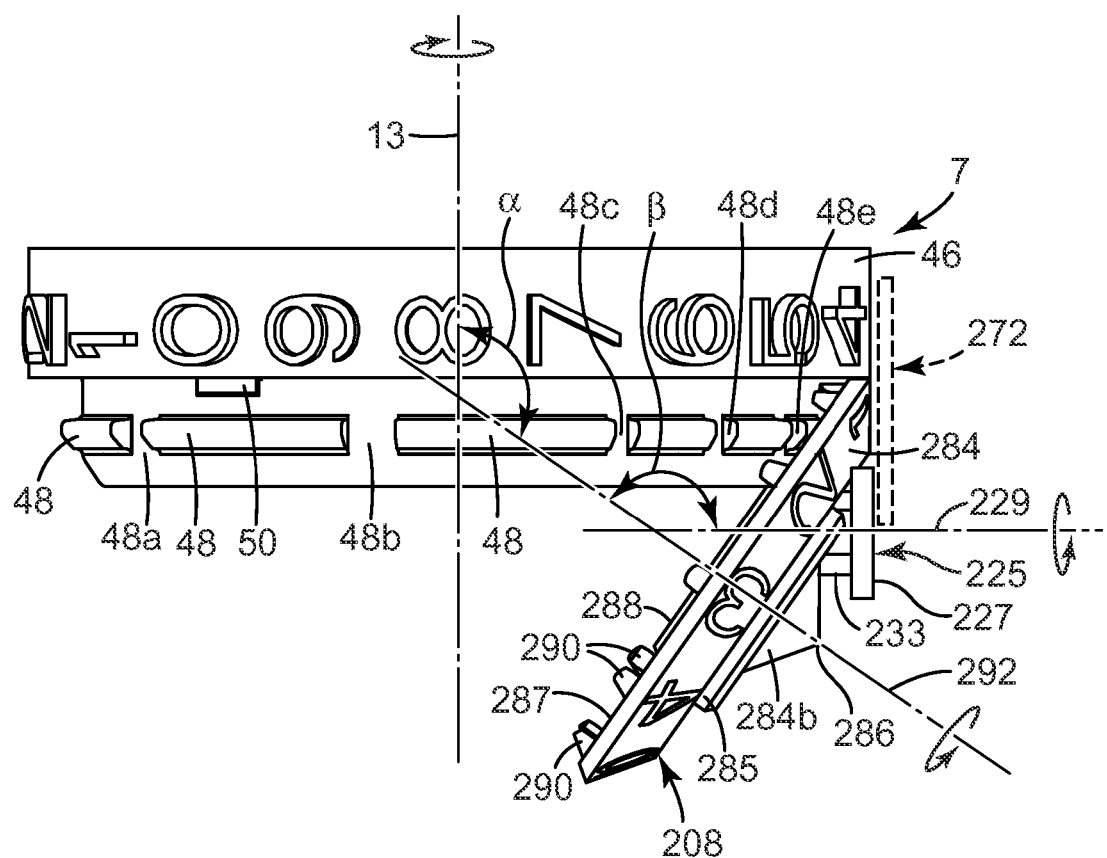
FIG. 19 represents a side view of the interface between the units rotational ring, the tens cone and the hundreds disk of the dose counter of FIGS. 12-18.

In this embodiment, the tens cone 208 has numbers 9 to 0 arranged descending clockwise about external conical surface 284 of the tens cone 208 when viewed from a pointed end 286 thereof (i.e., in the sequence 9 8 7 6 5 4 3 2 1 0). The orientation for readability of the numbers is similar to the orientation on the tens cone 8. On the tens cone 208, the conical surface 284 does not extend to the pointed end 286. The tens cone conical surface 284 extends only in a band adjacent an outer circumferential edge of the tens cone 208. An annual recess 284a is concentrically disposed within the band, and a small cone 284b protrudes concentrically within that recess 284a, capped by the pointed end 286. Also protruding within the recess 284a is a circumferential rim 285 surrounding the cone 284b. The rim 285 has a single gap 285a therein, and the recess 284a also has a ramp 289 projecting outwardly therefrom, which extends generally radially and outwardly from the gap 285a. An internal surface 287 of the tens cone 208 has a raised frustum 288 pointing the opposite way from the conical surface 284 as can be seen in FIG. 18. Also on its internal surface 287 of the tens cone 208, an annular series of equally spaced pegs 290 extend parallel to and in the same direction as the frustum 288 (generally parallel to an axis 292 of rotation for the tens cone 208, as seen in FIG. 19). Since there are only ten numbers on the external surface 284 of the tens cone 208, there are only ten corresponding pegs 290 on the internal surface 287 thereof.

Figure 16:
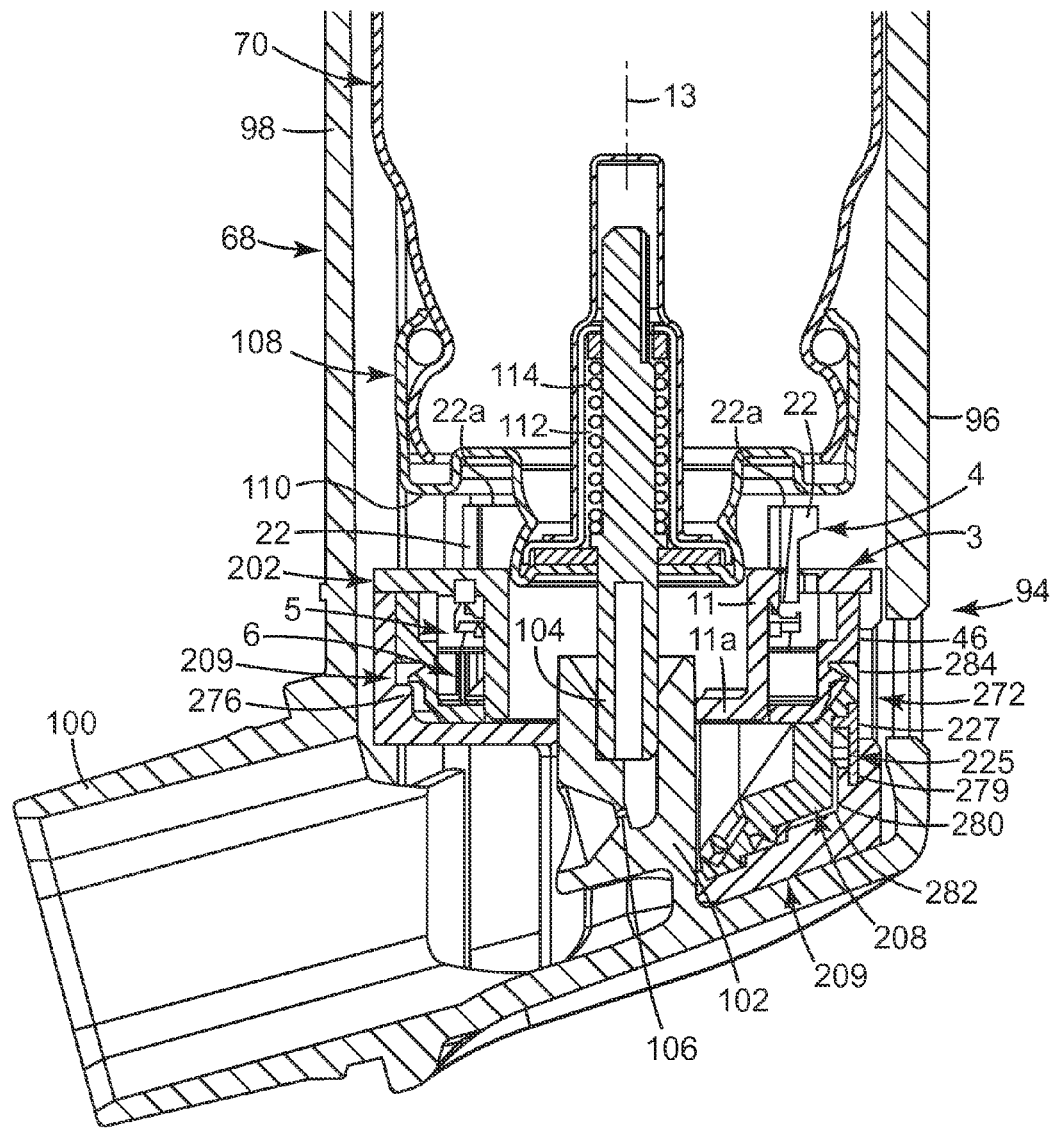
FIG. 16 represents a partial axial sectional view of a press-and-breathe inhaler incorporating the dose counter of FIGS. 12 and 15.
Figure 17:
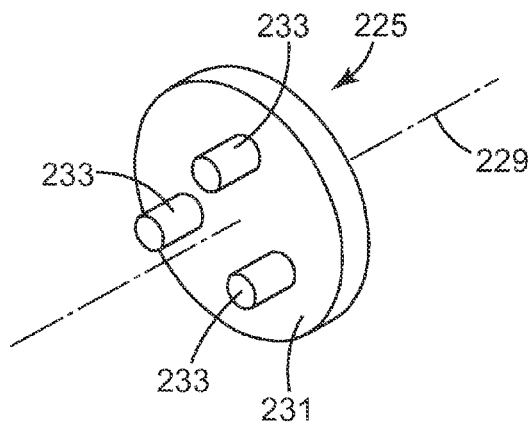
FIG. 17 represents an isometric view an interior side of the hundreds disk of the dose counter of FIG. 12.

The housing 209 again has a generally cylindrical body 262, with two forward wings 264 projecting outwardly therefrom and two legs 266 extending downwardly therefrom. The cylindrical body 262 and the wings 264 and the legs 266 are formed to mate with interior surfaces of the actuator housing 68 for the aerosol container 70 (see FIG. 16). A count viewing window 272 is provided in the cylindrical body 262. On an interior circumferential surface 274 of the cylindrical body 262, a ledge 276 is disposed for alignment with the units rotational ring 7, as seen in FIG. 16. The cylindrical body 262 has a top rim with a plurality (e.g., five) of slots 278 shaped for reception of the projections 17 on the lid 3 to provide a snap fit connection of the lid 3 and housing 209 or those components may be press fit together, or maybe ultrasonically or otherwise (e.g., laser) welded together.

The housing 209 has a lower rear internal cone shaped recess 280 designed to accommodate the tens cone 208 therein, as best seen in FIGS. 16 and 18. The tens cone 208 can thus rotate in a stable manner about an axis directed diagonally forward and upward from a rear corner 282 of the recess 280. The housing 209 also has a generally vertically aligned arcuate slot 279 adjacent the recess 280 for reception and partial rotatable support of the hundreds disk 225. The hundreds disk 225 has an external indicia bearing surface 227 extending generally perpendicular to a rotational axis 229 thereof (see, e.g., FIG. 19). The external surface 227 has numbers from 2 to 0 arranged descending clockwise thereon. The orientation of the numbers is generally adjacent and tangential to a circumferential edge of the circular external surface 227, with each number bisected horizontally by a radial line extending outwardly from the axis 229. An internal surface 231 of the hundreds disk 225 has three annularly equally spaced pegs 233 projecting outwardly therefrom, in a direction generally parallel to the axis 229 (see FIG. 17). Higher counts are possible by incorporating more numbers on a larger hundreds disc and correspondingly more pegs to match. When assembled, the internal surface 231 of the hundreds disk 225 faces and engages portions of the external surface 284 of the tens cone 208.

Figure 15:
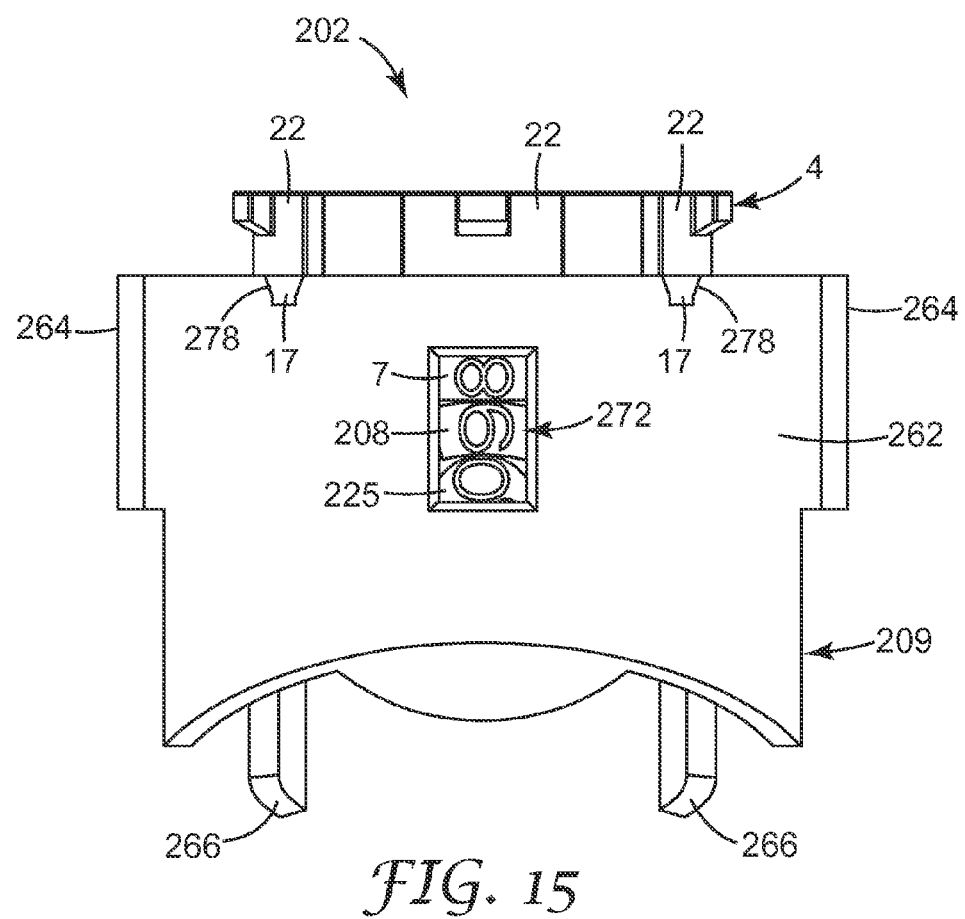
FIG. 15 represents a rear view of the assembled dose counter of FIG. 12.

The dose counter 202 may be assembled by inserting the hundreds disk 225 into the slot 279 of the housing 209. The tens cone 208 is then inserted into the housing 209, with the pointed end 286 of the small cone 284b thereon seated in the rear corner 282 of the recess 280 in the housing 209. In the indicia count mode, the hundreds units number "2" of the hundreds disk 225 is aligned for observation through the viewing window 272, and the tens units number "0" on the tens cone 208 is aligned for observation through the viewing window 272. The circumferential rim 48 of the units rotational ring again has three slots 48c, 48d and 48e (such as shown in FIG. 1) that correspond to positions of three of the pegs 290 on the tens cone 208 such that by correct orientation of the ring 7 and the cone 208, the units rotational ring 7 can be seated on the ledge 276 of the housing 209, with three of the pegs 290 traversing the circumferential rim 48. Once initially assembled, the ones units number "9" on the units rotational ring 7 is aligned for observation through the viewing window 272. The spring 6, units teeth ring 5, and indexer 4 can then be assembled in order over the units rotational ring 7, and the lid 3 fitted over the castellations 22 of the indexer 4 and then engaged with the housing 209. This complete assembly thus defines the dose counter 202 as seen in FIG. 15. Once assembled, the internal working components of the dose counter 202 are fairly well enclosed by the housing 9 and lid 3, thus inhibiting the ingress of dust, fibers, fluff and other debris therein to protect those working components. The enclosure of the working components of the dose counter 202

(with the lid 3 engaged to the housing 9) also provides an assembly that is somewhat tamper resistant, and is durable and shock-resistant.

In the illustrated second embodiment, a maximum dosage count of "299" medication dosages is shown. This allows for some testing of the aerosol dispensing assembly (e.g., 9 initial "tester" counts available), with 200 user available dispensing counts remaining Changing the frequency or spacing of indicia on the units rotational ring, tens cone and/or hundreds disk (along with corresponding changes in the interactive geometry between those components) allows modification of the possible count indicia shown.

FIG. 16 shows a vertical cross-sectional view through part of a press-and-breathe aerosol inhaler incorporating the dose counter 202 of FIGS. 12, 15 and 18. As noted above, the purpose of the dose counter is to provide a display that indicates the number of doses of medication remaining or (in an alternative embodiment, not shown) the number already dispensed. The indicia provided for review by a user may be a suitable alphabetic, numeric, alphanumeric or color symbols, or any combination thereof, providing a sequential count up or count down of dispensed doses, or providing a more general indication, such as "full" or "empty". The indicia would be visible through a window 94 in a side wall 96 of the actuator housing 68; alternatively, the side wall 96 may be transparent or have at least a portion thereof made of a transparent material to provide a viewing area or lens for viewing the indicia and count. The press-and-breathe inhaler is of the same structure and components as illustrated in FIG. 3, and likewise cooperates with the dose counter 202 in the same manner to initiate a single ones units dosage count, as well as a change of decades (i.e., tens units) for counting by cooperation of the units rotational ring 7 and the tens cone 208. As illustrated in FIG. 16, the aerosol container 70 is aligned coaxially with the axis 13.

The housing 9 is designed to minimize interference and obstruction of the medication spray and airflow paths in the actuator housing 68. In one embodiment, the dose counter 202 is clipped or retained within the actuator housing 68 by suitable detents or other engaging structure (not shown) between the actuator housing 68 and the dose counter 202. In addition, the dose counter 202 is designed to be useable with a variety of metering valve designs, and to fit compactly within commercially available actuator housing profiles so that it is not necessary to change the external configuration of those actuator housings to accommodate the inventive dose counter 202 therein. The FIGS. illustrate the dose counter 202 of the present invention in combination with an actuator housing for an inhaler of the type used for dispensing medication from a pressurized aerosol container. However, inhalers in other forms may be used with the present invention including, for example, dry powder inhalers, portable nebulizers, and other dispensers that use reciprocal mechanism.

As seen in FIGS. 14, 16, 18 and 19, portions of the hundreds disk 225, the tens cone 208 and the units rotational ring 7 converge adjacent the viewing window 272 of the housing 209. At the viewing window 272, a circumferential segment of the outer surface 46 of the units rotational ring 7 that bear ones units indicia, an arcuate segment of the conical surface 284 of the tens cone 208 that bears tens units indicia, and an arcuate segment of the external surface 227 of the hundreds disk 225 that bears hundreds units indicia are aligned to collectively present a medication dosage count (for example, in FIG. 14, the count "100" is seen, and in FIG. 15, the count "098" is seen). At this juxtaposition of the indicia bearing surfaces of the units rotational ring 7, the tens cone 208 and the hundreds disk 225, those surfaces are sequentially tangential to each other at the viewing window 272, which provides a common view area for observing the indicia on the three separate indicia bearing surfaces. The external surface 227 of the hundreds disk 225 is thus generally parallel with the viewing area 272. As noted above, when a dose counter 202 is disposed within the actuator housing 68 (see FIG. 16), the viewing window 272 is aligned with the viewing window 94 in the side wall 96 of the actuator housing 68, thus presenting the common viewing area for observation by a user. The common viewing area is generally tangential to a circumferential surface of a cylinder disposed about the axis 13.

As seen in FIG. 19, the rotational axis 229 of the hundreds disk 225 and the rotational axis 13 of the units rotational ring 7 are perpendicular to one another. The axis 229 of the hundreds disk 225 is disposed at an obtuse angle $\beta$ with respect to the axis 92 of the tens cone 208. The angle $\beta$ may assume the same ranges or value as stated above with respect to the angle $\alpha$. In one embodiment, the axes 13 and 292 are coplanar, but not coaxial, parallel or perpendicular relative to each other. Likewise, in one embodiment, the axes 292 and 229 are coplanar, but not coaxial, parallel or perpendicular relative to each other. In other embodiments of the invention, these pairs of axes need not be coplanar.

Every tenth movement of the units rotational ring 7 results in a movement of the tens cone 208 due to interaction between one of the oblong lugs 50 (on the units rotational ring 7) and one of the pegs 290 (on the tens cone 208). The tens cone 208 thus rotates about its axis 292 as a function of the rotation of the units rotational ring 7 about its axis 13. Although the number of pegs 290 on the tens cone 208 is different from that illustrated in the first embodiment, the mechanics of the interaction between the tens cone 208 and the units rotational ring 7 are the same as illustrated in FIGS. 10 and 11. The lug 50 on the units rotational ring 7 engages sequentially each peg 290 of the tens cone 208 to cause the tens cone 208 to rotate as function of rotation of the units rotational ring 7. The circumferential ring 48 on the units rotational ring 7, in cooperation with the slots 48*a* and 48*b* therein (disposed relative to the lug 50), permit rotation of the tens cone 208 when desired, but inhibit its rotation at other times, while allowing continued rotation of the units rotational ring 7.

Every complete rotation of the tens cone 208 results in a rotational movement of the hundreds disk 225 due to interaction between the ramp 289 (on the tens cone 208) and one of the pegs 233 (on the hundreds disk 225). The relationship between the ramp 289 and the pegs 233 is illustrated schematically in FIGS. 20A-20F. This direct interaction between the tens cone 208 and hundreds disk 225 eliminates the need for any transfer gear or other translation components between a component bearing tens units (i.e., the tens cone 208) and a component bearing hundreds units (i.e., the hundreds disk 225). This arrangement requires fewer parts, is more economical in function, and is more compact.

The interaction and sequence for causing the hundreds disk 225 to change the hundreds units indicia displayed in the viewing window 272 involves engagement of the ramp 289 on the tens cone 208 with one of the pegs 233 on the hundreds disk 225. As seen in FIG. 20A, the tens cone 208 rotates counterclockwise, and the ramp 289 eventually moves into engagement with the peg 233*a* on the hundreds disk 225. As the tens cone 208 continues its counterclockwise rotation, as seen in FIG. 20B, the ramp 289 pushes the peg 233*a* (down and to the left, as viewed in FIG. 20B) and thereby causes the hundreds disk 225 to rotate about its axis in a counterclockwise manner. As shown in FIG. 20C, further counterclockwise rotation of the units rotational ring 7 causes the ramp 289 to further push the peg 233*a* down and to the left, thereby causing further rotation of the hundreds disk 225 in a counterclockwise manner about its axis. As shown in FIG. 10D, further counterclockwise rotation of the tens cone 208 causes the ramp 289 to further push the peg 233*a* down and to the left, thereby causing further rotation of the hundreds disk 225 in a counterclockwise manner about its axis. Eventually, as illustrated in FIG. 20E, the ramp 289 pushes the peg 233*a* so far down that rotation of the hundreds disk 225 moves the peg 233*a* out of the arcuate path of the advancing ramp 289 (i.e., out of reach of the ramp 289, as seen in FIG. 20E). Once this happens, further counterclockwise rotational movement of the hundreds disk 225 stops, and a new hundreds units number is aligned for observation through the viewing window 272. In an embodiment where the hundreds disk is rotated to show a count down of the number of dosages remaining, the new hundreds units number displayed will be a smaller number than the previous number that was displayed.

Rotation of the hundreds disk 225 relative to the rotation of the tens cone 208 occurs each time the ramp 289 engages one of the pegs 233. In the embodiment illustrated, there is a single ramp 289, so for every single rotation of the tens cone 208, the hundreds disk 225 is rotated through one hundreds unit number (or, in the case where the hundreds disk 225 has three hundreds units thereon, the hundreds disk 225 is rotated 120°).

Figure 20A:
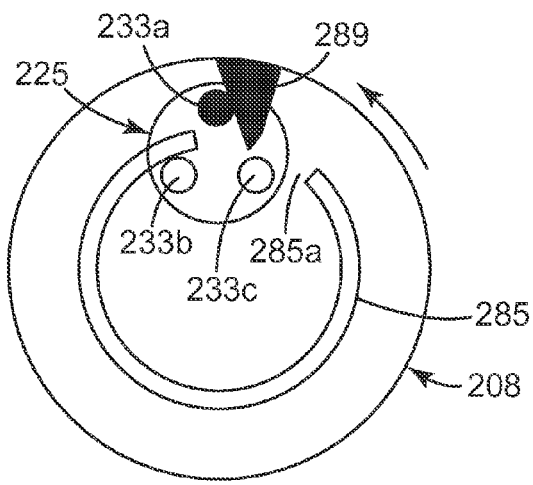
FIGS. 20A, 20B, 20C, 20D, 20E and 20F represent schematically the interface between the tens cone and the hundreds disk that facilitates rotation of the hundreds disk as a function of rotation of the tens cone, for the embodiment of the dose counter illustrated in FIGS. 12-19.
Figure 20B:
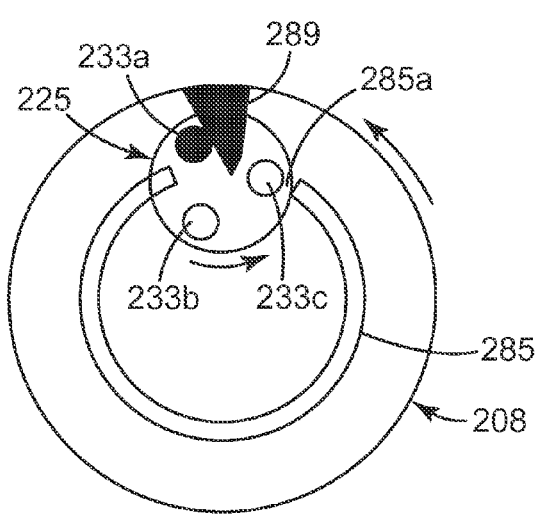
Figure 20C:
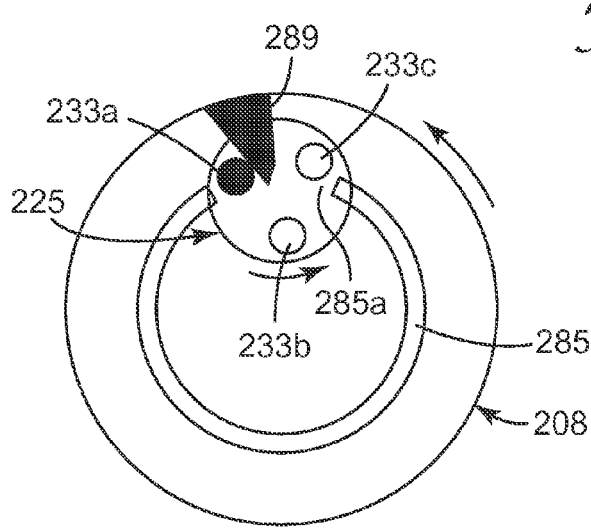
Figure 20D:
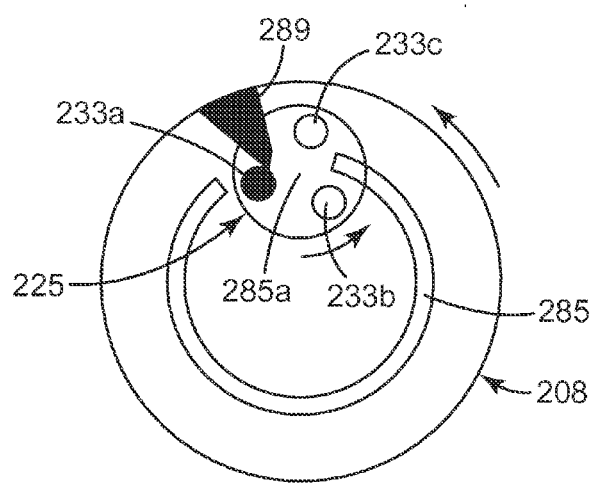
Figure 20E:
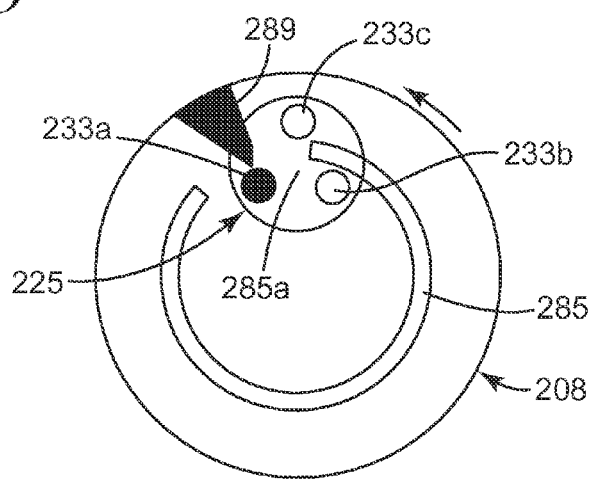

In FIGS. 20A-20F, the pegs on the hundreds disk 225 are referenced as pegs 233*a*, 233*b* and 233*c*. As noted above, the external surface 284 of the tens cone 208 has an annular recess 284*a* thereon. The recess 284*a* is formed to accommodate the pegs 233. The circumferential rim 285 has a slot 285*a* aligned adjacent the ramp 289 and is provided to prevent movement of the pegs 233, as can be seen in the sequential illustrations of FIGS. 20A-20F. Thus, as peg 233*a* is moved by the ramp 289, peg 233*c* moves through the slot 285*a* in the circumferential ring 285 (from below the slot 285*a*, as seen in FIG. 20A, to above the slot 285*a*, as seen in FIG. 20D). At the same time, peg 233*a* moves from above the slot 285*a* (see FIG. 20A) to below the slot 285*a* (see FIG. 20E).

Figure 20F:
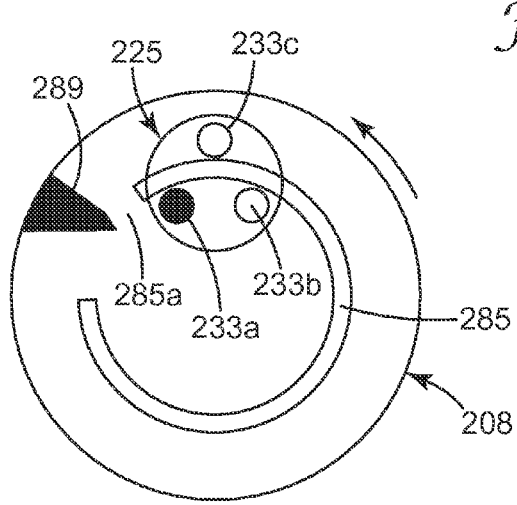

The circumferential rim 285 acts to prevent rotation of the hundreds disk 225 except when the ramp 289 engages one of the pegs 233. For example, as seen in FIG. 20F, hundreds disk 225 is constrained from movement about its axis by the circumferential rim 285 extending between the peg 233*c* and the peg 233*a* (and the peg 233*b*). While movement of the hundreds disk 225 is allowed when the tens cone 208 and hundreds disk 225 are aligned as seen in FIGS. 20A-20E, the hundreds disk 225 is prevented from movement once in the configuration shown in FIG. 20F. The circumferential rim 285 extends between the opposed pegs 233*c* and 233*a* (or pegs 233*c* and 233*b*), and continued rotation of the tens cone 208 will maintain this relationship until the slot 285*a* of the circumferential rim 285 again reaches the position shown in FIG. 20A. Thus, once the hundreds disk 225 has been moved by interaction with the ramp 289 on the tens cone 208, it cannot begin further rotation until the ramp 289 again presents itself for engagement with the peg 233*c* on the hundreds disk 225, even though the tens cone 208 is rotating about its axis to display differing tens units numbers.

In one embodiment, cooperative features are provided between the housing 9 and hundreds disk 225 that will, when the hundreds disk 225 has been rotated to a position that shows a hundreds units 0 numeral in the view window 272, prevent further rotation of the hundreds disk 225. The tens cone 208 can continue to rotate as it counts down its ten remaining tens units counts, and then it would be prevented from further rotation by the hundreds disk 225. At this point, the units rotational ring 7 can continue to rotate as it counts down its nine remaining ones units counts, and then it would be prevented from further rotation by the tens cone 208. At this point, the viewing window would display a zero count for the dose counter 202. To the extent further medication is present in the aerosol container, it may be dispensed by a user using the aerosol dispensing assembly, but the dose counter 202 will not register any further dosage counts. As an alternative, the aerosol dispensing assembly could be designed to cease dispensing doses of medication once the zero count has been reached, for example by limiting the free movement of the indexer 4.

In essence, the inventive dose counter in the embodiment illustrated in FIGS. 12-20, operates in the following fashion. When a user actuates the inhaler by pushing the aerosol container 70 downwardly into the actuator housing 68, the valve ferrule 110 engages the indexer 4 to push it downwardly. Indexer 4 engages and then causes rotation of units teeth ring 5. The unit rotational ring 7 is coupled rotationally to the units teeth ring 5, so it rotates as well. As the aerosol container 70 reciprocates down and up to complete a single dosage of medication therein, the indexer 4 and units teeth ring 5 also reciprocate down and up relative to the units rotational ring 7. One complete down and up reciprocal motion of the units teeth ring 5 causes the units rotational ring 7 to rotate on its axis 13, a single ones units count change in position thereof. Rotation of the units rotational ring 7 is translated into rotation of the tens cone 208 by engagement of the lug 50 on the units rotational ring 7 with one of the pegs 290 on the tens cone 208. However, the tens cone 208 is only rotated periodically relative to the units rotational ring 7, to indicate a change in decade of the counts (i.e., the tens cone 208 is only moved once for every ten movements of the units rotational ring 7). Each time the units rotational ring 7 counts ten ones units counts, the tens cone 208 is indexed one position to change the tens unit count displayed thereon. Rotation of the tens cone 208 is translated into rotation of the hundreds disk 225 by engagement of the ramp 289 on the tens cone 208 with one of the pegs 233 on the hundreds disk 225. However, the hundreds disk 225 is only rotated periodically relative to the tens cone 208, to indicate a change in hundreds units of the counts (i.e., the hundreds disk 225 is only moved once for every ten movements of the tens cone 208). Each time the tens cone 208 counts ten tens units counts, the hundreds disk 225 is indexed one position to change the hundreds units count displayed thereon.

Figure 21:
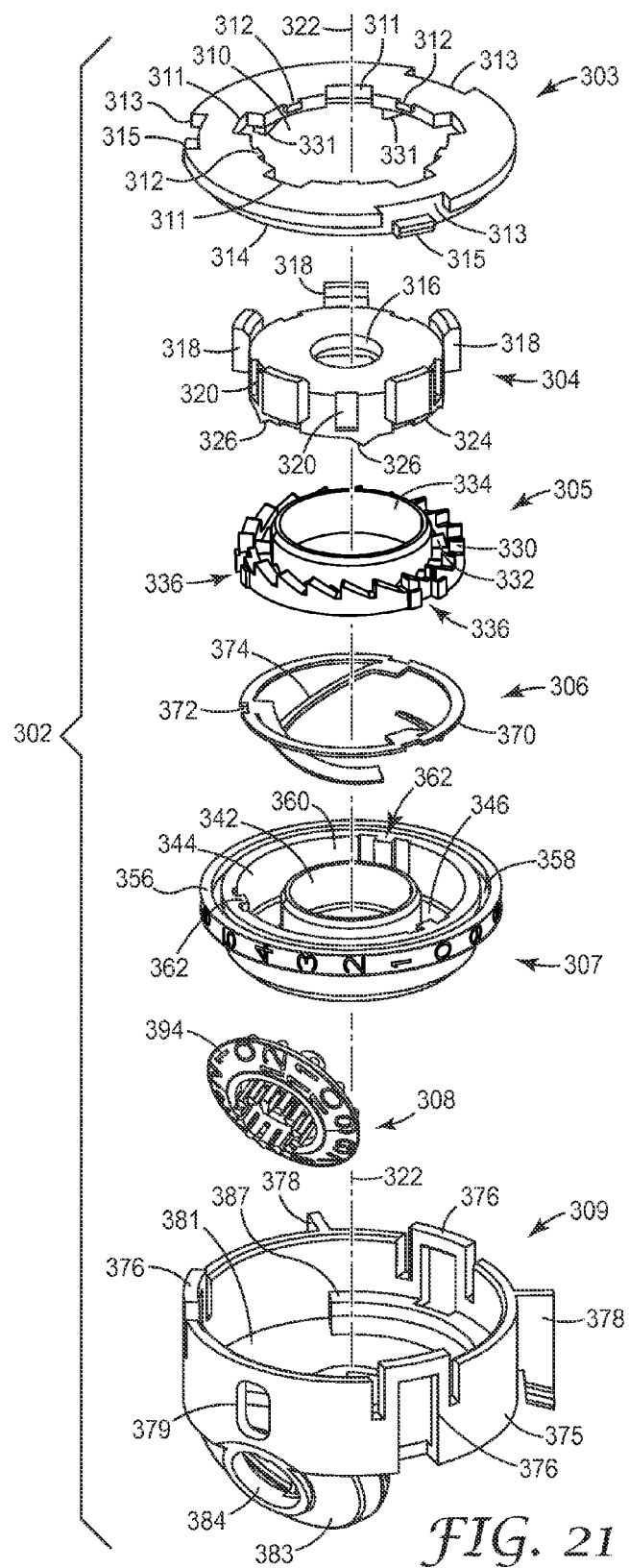
FIG. 21 represents an exploded isometric view of a third embodiment of the dose counter of the present invention.

A third embodiment of the inventive dose counter is illustrated in FIGS. 21-30. FIG. 21 illustrates a dose counter 302 of the present invention which provides a user with a possible dosage count ranging from 0 to 129. The dose counter 302 is similar to the dose counter 2 of FIGS. 1-11, but each component thereof is modified. However, the dose counter 302 does include the same relative components, such as a lid 303, indexer 304, units teeth ring 305, compression spring 306, units rotational ring 307, tens cone 308 and housing 309. While the components differ in structure, they operate similarly to those described with respect to the dose counter 2 of FIGS. 1-11. Actuation of the indexer 304 by a user causes indexed rotation of the units rotational ring 307, and the tens cone 308 is rotated as a function of rotation of the units rotational ring 307.

The lid 303 is generally annular. A central circular hole 310 has a plurality (e.g., five) of circumferentially equally spaced radial hole extensions 311 of slightly greater radius thereon. Between adjacent hole extensions 311, the lid 303 has a plurality (e.g., five) of circumferentially equally spaced small radially inward protrusions 312 thereon. Adjacent an outer circumferential edge of the lid 303, a plurality (e.g., three) of circumferentially equally spaced cutaways 313 are defined by a radius slightly smaller than the outer edge. A cylindrical extension 314 extends downwardly from the lid 303, and has a smaller radius than the outer edge of the lid 303 (equal to the radius of the cutaways 313). Below each cutaway 313, the cylindrical extension 314 has an outward radial protrusion 315, shorter in circumferential length than the cutaways 313. The protrusions 315 are designed to form a snap fit with three doorframes 376 in the housing 309, as explained herein.

The indexer 304 is shaped generally like a cylindrical cap with a central hole 316. The indexer 304 has a plurality (e.g., five) peripheral castellations 318 that are designed to pass through the hole extensions 311 of slightly greater radius in the central hole 310 of the lid 303. The indexer 304 also has a plurality (e.g., five) of peripheral grooves 320 extending from a top thereof to almost a bottom thereof, in directions parallel to an axis 322 of the indexer 304 and its associated lid 303 and designed to accommodate the protrusions 312 of the lid. On a bottom circumferential edge 324 of the indexer 304, a plurality (e.g., five) of circumferentially equally spaced sawtooth projections 326 are provided for interaction with an inner ring of teeth on the units teeth ring 305.

The units teeth ring 305 is also coaxial with axis 322, and is provided with two rings of upstanding teeth. An outer ring of teeth 330 is disposed for engagement with ratchet members 331 on the bottom surface of the lid 303. An inner ring of teeth 332 is arranged for engagement with the sawtooth protrusions 326 on the indexer 304. A central cylinder 334 extends upwardly from the units teeth ring 305 to aid in keeping dust out of the dosage counter mechanism, and to serve as a guide for relative axial movement with the an inner cylinder 342 of the units rotational ring 307 (see FIG. 26). A circumferential perimeter of the units teeth ring 305 has a plurality (e.g., four) of circumferentially equally spaced features 336, with each feature 336 comprising a vertical recess with a pair of vertically oblong lugs on each side thereof.

The interaction of the lid 303, indexer 304 and units teeth ring 305 is functionally similar to that disclosed in WO 2005/060535 A2 for causing units teeth ring 305 to rotate about the axis 322 (i.e., to rotate the ring 305 an indexed amount as each dose of medication is dispensed).

Figure 22:
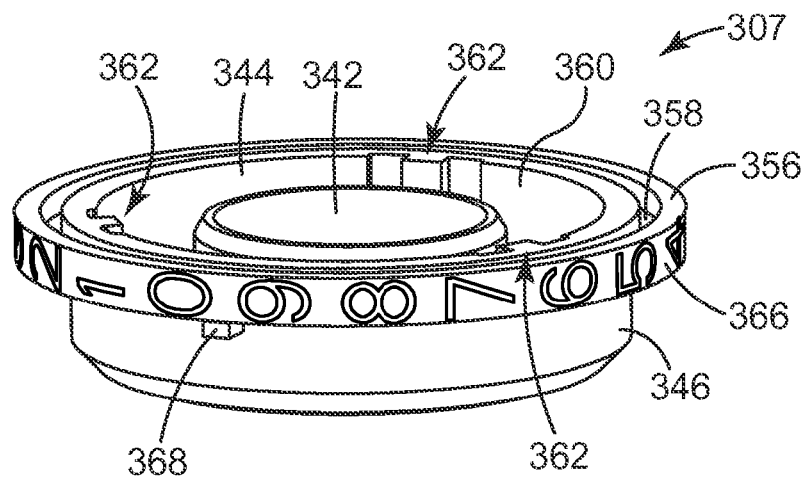
FIG. 22 represents an isometric view of a units rotational ring of the dose counter of FIG. 21.
Figure 23:
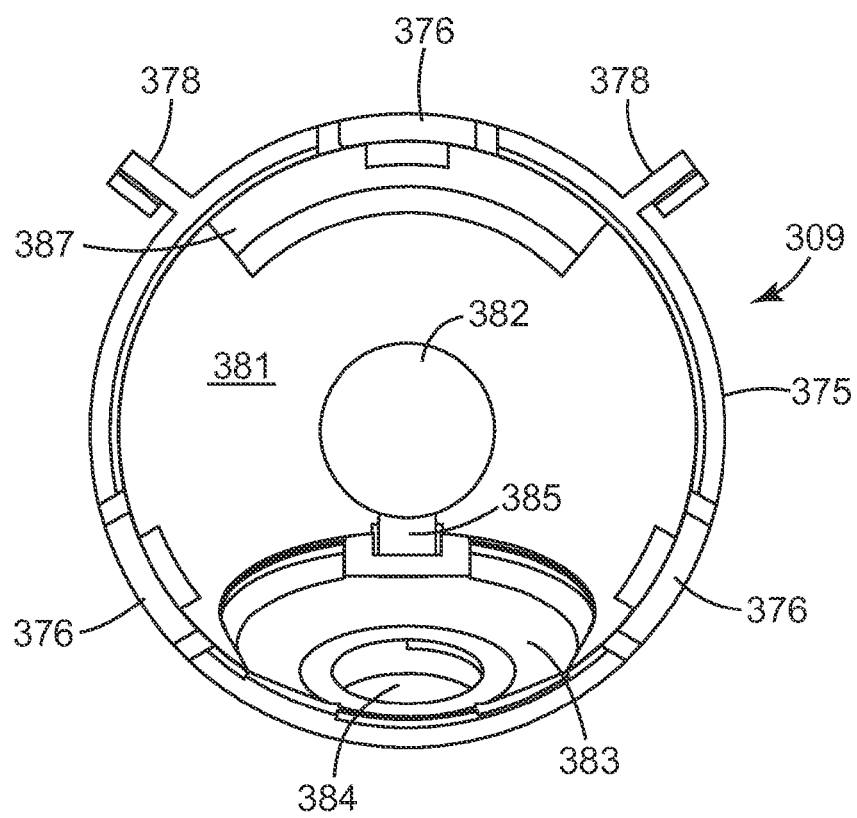
FIG. 23 represents a top view of a housing for the dose counter of FIG. 21.
Figure 26:
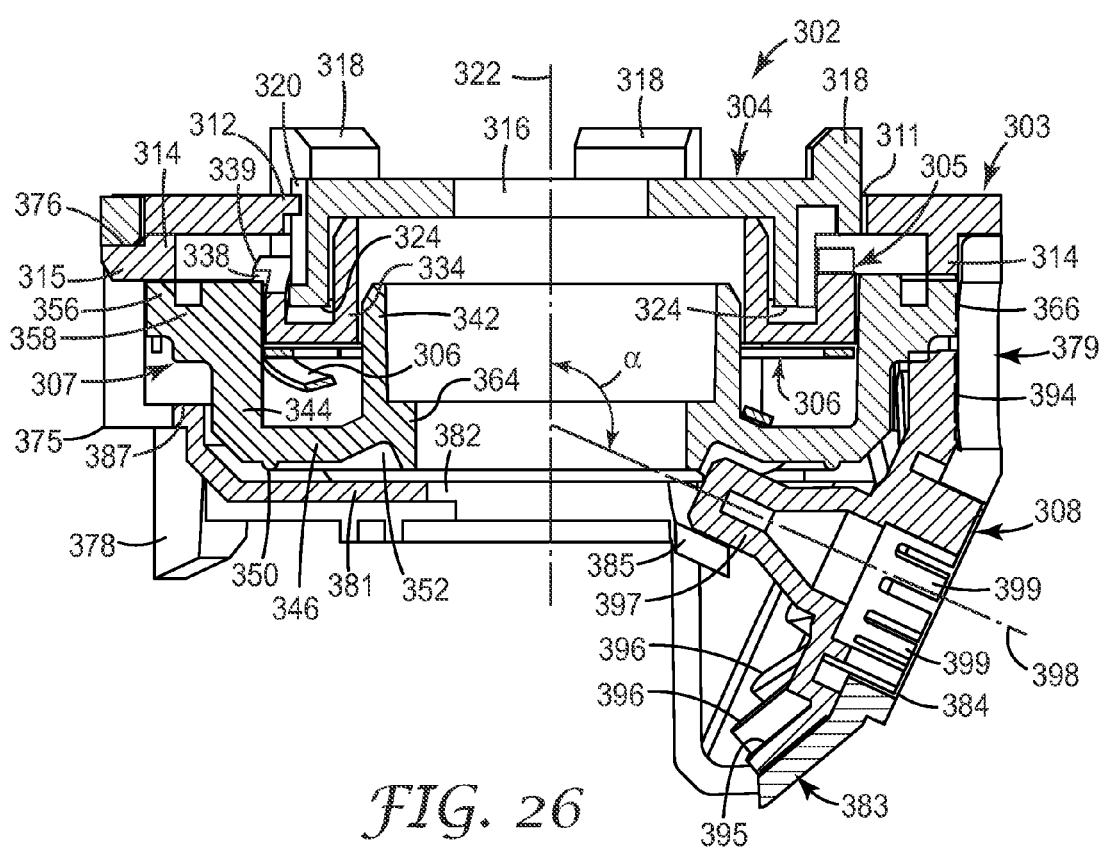
FIG. 26 represents a sectional view of the assembled dose counter of FIGS. 24 and 25, with the lateral section taken through the viewing window thereof.
Figure 27:
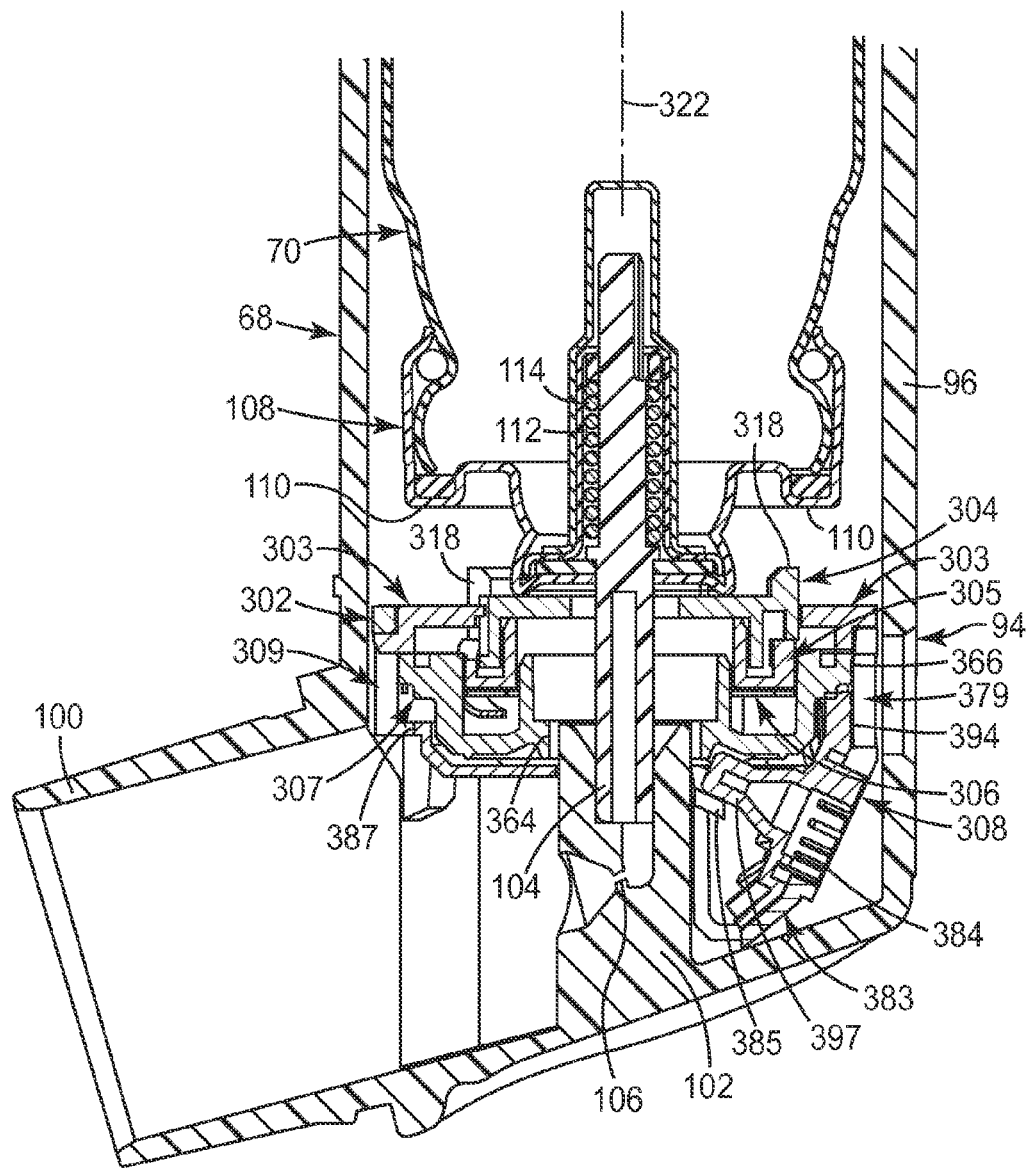
FIG. 27 represents a partial axial sectional view of a press-and-breathe inhaler incorporating the dose counter of FIGS. 21, 24, 25 and 26.
Figure 28:
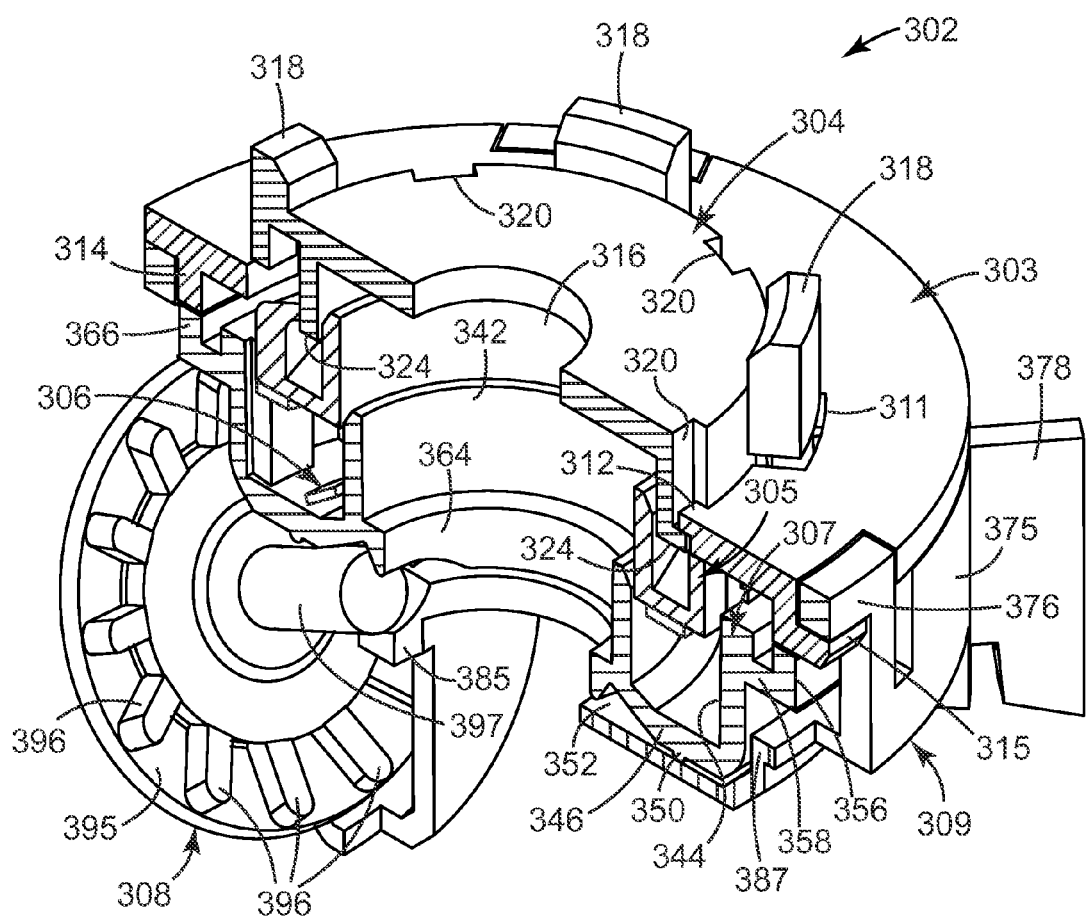
FIG. 28 represents an isometric sectional view of the assembled dose counter of FIGS. 21, 24, 25 and 26, with the lateral section taken through the viewing window thereof (and a tens cone not shown in section).

The units rotational ring 307 is generally in the form of inner and outer coaxial cylinders 342 and 344, joined by an annular base 346. As seen in FIG. 26, a circumferential rib 350 is disposed on a bottom side of the annular base 346. The rib 350 provides a low friction surface for the units rotational ring 307 to rotate relative to a shelf 381 of the housing 309 on which it rests. An upwardly extending circumferential groove 352 is also provided on a bottom surface of the annular base 346, coaxially within the rib 350, to accommodate a spindle 397 of the tens cone 308, at all rotational positions of the units rotational ring 307 with respect to the tens cone 308. The outer cylinder 344 has a further external cylindrical section 356 joined approximately midway up an outer surface of the outer cylinder 344 via an annular wall 358. An internal circumferential surface 360 of the outer cylinder 344 has a plurality (e.g., four) of features 362 (see FIG. 22). Each feature 362 comprises a pair of grooves on either side of a vertically oriented radially inwardly projecting rib. The features 362 are designed to slide in an axial orientation with the corresponding features 336 of the units teeth ring 305. The inner cylinder 342 of the units rotational ring 307 has a diameter such that it slides axially inside the central cylinder 334 of the units teeth ring 305. As seen in FIGS. 26 and 27, an additional small cylindrical section 364 (of smaller diameter than the inner cylinder 342) extends from a lower end of the units rotational ring 307, and is designed to fit around the nozzle block 102 of the actuator housing 68. The external cylindrical section 356 has an outer cylindrical surface 366 bearing indicia for indicating ones units dosage counts of medication being dispensed. As illustrated by FIGS. 21 and 22, the indicia may take the form of digits from 9 to 0 arranged equally spaced twice about the circumference of the outer surface 366 of the external cylindrical segment 356. The digits are oriented so that they can be underlined by lines parallel to the axis 322, and the digits are arranged in two sequences of descending order in a clockwise direction when viewed from the bottom of the units rotational ring 307 (i.e., in the sequence: 9 8 7 6 5 4 3 2 1 0 9 8 7 6 5 4 3 2 1 0). As seen in FIG. 22, the units rotational ring 307 has an oblong lug 368 spaced below and between each space between a 0 digit and its adjacent 9 digit. Since the digits 9 to 0 are arranged twice around that units rotational ring 307, there are two oblong lugs 368 thereon (on opposite sides of the ring 307).

The features 362 on the units rotational ring 307 are disposed to align with the features 336 on the units teeth ring 305. The outer circumferential edge of the units teeth ring 305 is slightly smaller in diameter than the internal surface 360 of the outer cylinder 344, thus allowing axial movement of the units teeth ring 305 relative to the units rotational ring 307. However, while such axial movement is allowed, the interaction of the features 362 and 336 couple the units teeth ring 305 and units rotational ring 307 for rotational purposes relative to the axis 322.

The compression spring 306 is similar to that disclosed in the embodiments above. For example, it can be in the form an annular leaf spring 370. In the embodiment illustrated in FIG. 21, the leaf spring 370 has a plurality (e.g., three) of cutouts 372 extending radially inwardly from an outer circumferential edge thereof. Each of the cutouts 372 is formed and aligned to axially receive one of the features 362 of the units rotational ring 307 therein, thereby allowing axial movement of the compression spring 306 relative to the units rotational ring 307. The leaf spring 370 has an annular ring with a plurality (e.g., three) of axially extending spring elements or leafs 374 thereon. The spring elements 374 are biased downwardly from the leaf spring 370 for engagement with the top of the annular base 346 of the units rotational ring 307. In one embodiment, the outer end of each leaf 374 is curved or otherwise formed to facilitate to smooth sliding of the outer end with respect to the annular base 346. A top surface of the ring of the leaf spring 370 engages a bottom surface of the units teeth ring 305. The leaf spring 370 thus urges the units teeth ring 305 axially away from the annular base 346 of the units rotational ring 307 and toward the sawtooth projections 326 on the indexer 304 and the ratchet members 331 on the bottom surface of the lid 303.

While cooperative features 336 and 362 are shown, any suitable keyed features between units teeth ring 305 and units rotational ring 307 will suffice to couple those two components together for rotation, yet allow relative axial movement. In one embodiment (not shown), rotation of the compression spring 306 relative to the units teeth ring 305 or units rotational ring 307 is permitted. However, to the extent it is desired that rotation of the compression spring 306 also be constrained with respect to the units teeth ring 305 or units rotational ring 307, while features 362 and cutouts 372 are shown for that purpose, any suitable keyed feature to accomplish that end will suffice. The housing 309 has a generally cylindrical body 375 with a plurality (e.g., three) of doorframe features 376, two forward legs 378 and a viewing window 379 thereon. The housing 309 is also generally coaxial with respect to the axis 322, and has a lateral shelf 381 therein. The shelf 381 has a central hole 382 therethrough for accommodating the nozzle block 102 of the actuator housing 68, as seen in FIGS. 26 and 27. On a rear side thereof (defined as including the viewing window 379), the housing 309 has a conical housing section 383 extending downwardly therefrom and designed to accommodate the tens cone 308 therein, as seen in FIGS. 24-28. The tens cone 308 is aligned to rotate in a stable manner about an axis directed diagonally forward and upward from the rear of the housing 309. The relationship of the axis of the tens cone 308 relative to the axis 322 of the units rotational ring 307 in this embodiment is similar to that illustrated and stated for those components in FIGS. 8 and 19 of the first and second embodiments (i.e., for FIG. 8, the axis 92 of tens cone 8 and the axis 13 of units rotational ring 7, and for the FIG. 19, the axis 292 of the tens cone 208 and the axis 13 of the units rotational ring 7). The conical housing section 383 has a central hole 384 therethrough, and internally is shaped to support a conical wall of the tens cone 308 and to surround and engage splines thereon (as well as providing upper and lower axis passages for assembly and tooling). In addition, the conical housing section 383 has a gutter portion 385 (see FIG. 26) at its apex end where it adjoins the shelf 381 to support an upper part of a spindle of the tens cone 308. The circular hole 384 has a projection 386 extending radially inwardly thereon (see FIGS. 30A-D). Adjacent a lower front end of the housing 309, the cylindrical wall 375 has a stepped portion 387 which partly conforms to an external surface of units rotational ring 307. This stepped portion 387 on the external profile of the housing 309 is shaped to minimize potential interference with medication spray emerging from the spray orifice 106 of the nozzle block 102 when the inhaler is actuated.

Figure 24:
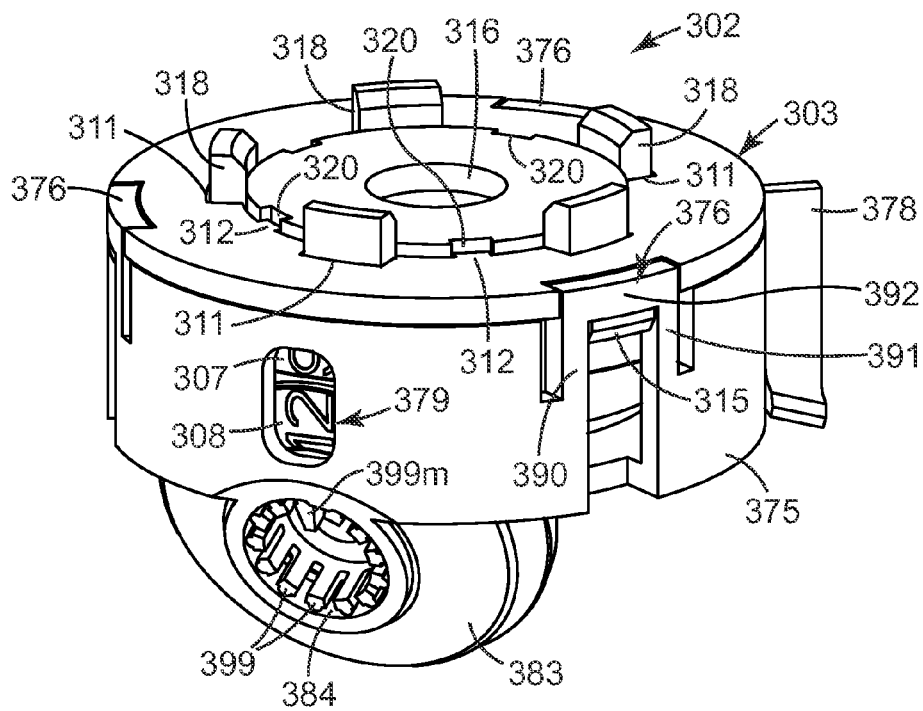
FIG. 24 represents an isometric assembled view of the dose counter of FIG. 21, as viewed partially from above.
Figure 25:
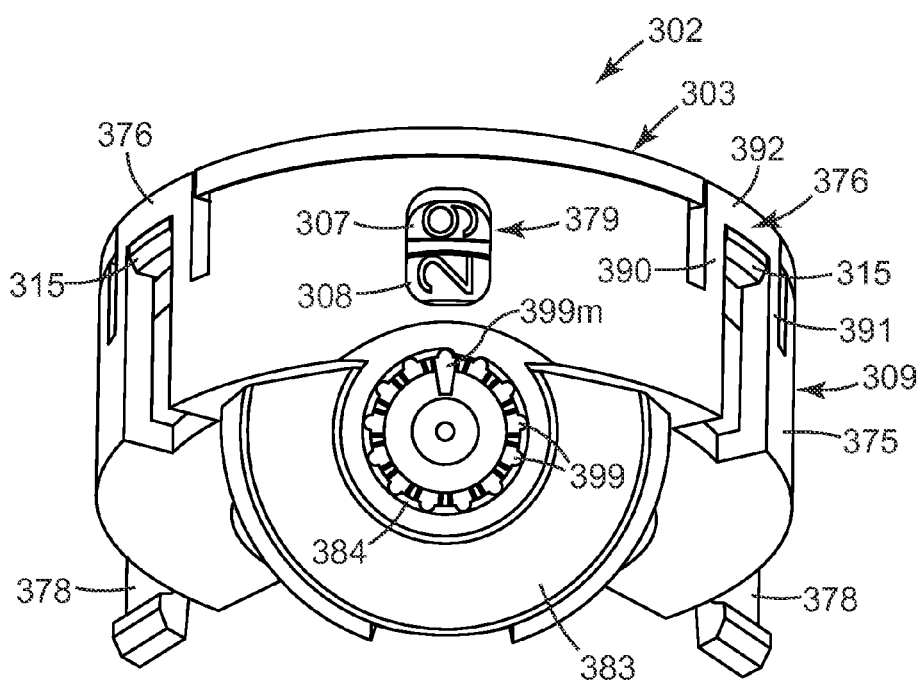
FIG. 25 represents an isometric assembled view of the dose counter of FIG. 21, as viewed partially from below.

Each doorframe feature 376 has an inverted U-shaped section defined by upwardly extending legs 390 and 391 and cross beam member 392 (see FIGS. 24 and 25). Upon assembly of the dose counter 302, each protrusion 315 is aligned within one of the doorframe features 376. Each doorframe feature 376 flexes outwardly as the protrusion 315 passes by it during assembly, and then snaps back into place with the cross beam member 92 over the protrusion 315, thereby fixing the lid 303 to the housing 309. Of course, the lid 303 and housing 309 may be otherwise connected together, such as by press fit connections, or may be ultrasonically or otherwise (e.g., laser) welded together.

The tens cone 308 has numbers from 12 to 0 arranged descending clockwise about an external conical surface 394 of the tens cone 308 when viewed from an apex of the conical surface 394 (e.g., in the sequence: 12 11 10 9 8 7 6 5 4 3 2 1 0). The orientation for readability of the numbers is similar to the orientation on the tens cone 8. On the tens cone 308, the conical surface 394 extends only in a band adjacent an outer circumferential edge of the tens cone 308. An internal surface 395 of the tens cone 308 is also generally conical (inversely) and is provided with a plurality (e.g., thirteen) of radial spokes 396. A forward and upwardly directed spindle 397 extends from the center of the internal surface 395 of the tens cone 308.

The tens cone 308 rotates about an axis 398, once assembled in the dose counter 302 (as seen in FIG. 26). On its external side, the tens cone 308 has a plurality (e.g., thirteen) of splines 399 arranged annularly about and parallel to the axis 398. The splines 399 project externally from the tens cone 308 in a generally cylindrical configuration to define a boss that is, upon assembly, received within the hole 384 of the conical housing section 383 in the housing 309. The splines 399 thus point in an opposite direction from the spindle 397 on the tens cone 308. Twelve of the splines 399 are identical in lateral cross section, having a cross section similar to that of a "fairy cake" or "cupcake" (see, e.g., splines 399a to 399l in FIG. 30A). A curved top portion or cap of each spline 399 is farthest from the axis 398 of the tens cone 308. The thirteenth spline 399m is, in part, similarly shaped, but has a base portion 400 extended axially inwardly toward the axis 398 of the tens cone 308. The splines 399a to 399l are formed to be able to flex slightly radially inwardly relative to the axis 398, while the spline 399m is more rigid than the other splines 399a to 399l, and is not able to flex radially inwardly.

The dose counter 302 may be assembled by inserting the tens cone 308 into the housing 309, with the spindle 397 of the tens cone 308 seated upon the gutter portion 385 in the conical housing section 383 of the housing 309. The boss formed by the splines 399 is also aligned to extend into the hole 384 of the conical housing section 383. The units rotational ring 307 is then inserted and seated on the shelf 381 of the housing 309, above the tens cone 308 (see FIG. 26). In this embodiment, the units rotational ring 307 completely covers the tens cone 308 in the conical housing section 383, to inhibit the ingress of dust, fibers, fluff or other debris from falling into the tens cone 308.

The spring 306, units teeth ring 305 and indexer 304 can then be assembled in order over the units rotational ring 307, and the lid 303 fitted about the castellations 311 of the indexer 304. As explained above, the lid 303 is snap-fit engaged with the housing 309 by engagement of the protrusions 315 and associated doorframe features 376. This complete assembly thus defines the dose counter 302 as seen in FIGS. 24, 25, 26 and 27. Once assembled, the internal working components of the dose counter 302 are fairly well enclosed by the housing 309 and lid 303, thus inhibiting the ingress of dust, fibers, fluff and other debris therein to protect those working components. The enclosure of the working components of the dose counter 302 (with the lid 303 engaged to the housing 309) also provides an assembly that is somewhat tamper resistant, and is durable and shock-resistant.

FIG. 27 shows a vertical cross sectional view through part of a press-and-breath aerosol inhaler incorporating the dose counter 302 of FIGS. 21, 24, 25, 26 and 28. The purpose of the dose counter is to provide a display that indicates the number of doses of medication remaining, or (in an alternative embodiment, not shown) the number already dispensed. The indicia provided for review by a user may be suitable alphabetic, numeric, alphanumeric, or color symbols or any combination thereof, providing a sequential count up or count down of dispensed doses, or providing a more general indication, such as "full" or "empty". The indicia would be visible through a window 94 in a side wall 96 of the actuator housing 68; alternatively, the side wall 96 may be transparent or have at least a portion thereof made of a transparent material to provide a viewing area or lens for viewing the indicia and count. The press-and-breathe inhaler is of the same structure and components as illustrated in FIG. 3, and likewise cooperates with the dose counter 302 in a similar manner to initiate a single ones units dosage count, as well as a change of decades (i.e., tens units) for counting by cooperation of the units rotational ring 307 and the tens cone 308. As illustrated in FIG. 27, the aerosol container 70 is also aligned coaxially with the axis 322. In this embodiment, the ferrule 110 engages a top surface of the indexer 304. It will be appreciated by those familiar with metering valves that the profiles of various kinds of valve ferrule differ, and that the indexer is suitably designed to abut a the ferrule flatly to minimize variations in travel between valves of the same kind due to tolerances on components.

The inhaler is actuated to dispense a dosage of medication by pressing down on the aerosol container 70 relative to the actuator housing 68. When the inhaler is actuated, downward movement of the aerosol container 70 causes the valve ferrule 110 to push down on the indexer 304. The lid 303 is positioned low enough relative to the valve ferrule 110 so that those components never engage each other, thus ensuring sufficient space to allow adequate metering valve travel to guarantee the dispensing of a dose of medication. Engagement with the valve ferrule 100 causes the indexer 304 to move downwardly relative to the lid 303, and the sawtooth protrusions 326 of the indexer 304 engage teeth of the inner ring of teeth 332 of the units teeth ring 305. Once the outer ring of teeth 330 move low enough to clear the ratchet members 331 on the lid 303, the ring 305 rotates (as described in WO 2005/060535 A2). Such rotational movement results in coupled rotational movement of the units rotational ring 307. The compression spring 306 between the units rotational ring 307 and the units teeth ring 305 maintains relative engagement of the sawtooth protrusions 326 and inner ring of teeth 332 until the downward actuation force on the aerosol container 70 is removed, and the return spring 114 urges the valve ferrule 110 upwardly relative to the nozzle block 102. This allows the compression spring 306 to urge the indexer 304 upwards, whereupon the interaction of the outer ring of teeth 330 on the units teeth ring 305 with the ratchet members 331 on the lid 303 results in further rotational motion of the units teeth ring 305 together with further coupled rotational motion of the units rotational ring 307, thereby completing the ones units change to the count, corresponding to the actuation and corresponding to a single dosage of medication. The dose counter 302 is designed to count at (or close before) the firing point of the metering valve 108 on the aerosol container 70, and then "lose" any subsequent excessive axial travel (i.e., lost "motion") of the axially moving components of the dose counter 302. Thus, for each actuation of the inhaler, the units rotational ring 307 is indexed to move rotationally one count increment, which will change the ones units count visible via the windows 379 and 94.

The housing 309 is designed to minimize interference and obstruction of the medication spray and airflow paths in the actuator housing 68. In one embodiment, the dose counter 302 is clipped or retained within the actuator housing 68 by suitable detents or other engaging structure (not shown) between the actuator housing 68 and the dose counter 302. In addition, the dose counter 302 is designed to be useable with a variety of metering valve designs, and to fit compactly within commercially available actuator housing profiles so that it is not necessary to change the external configuration of those actuator housings to accommodate the inventive dose counter 302 therein. The FIGS. illustrate the dose counter 302 of the present invention in combination with an actuator housing for an inhaler of the type used for dispensing medication from a pressurized aerosol container. However, inhalers in other forms may be used with the present invention including, for example, dry powder inhalers, portable nebulizers, and other dispensers that use reciprocal mechanism.

As seen in FIGS. 24, 25, 26 and 27, portions of the tens cone 308 and units rotational ring 307 converge adjacent the viewing window 379 of the housing 309. At the viewing window 379, a circumferential segment of the outer surface 366 of the units rotational ring 307 that bears ones units indicia and an arcuate segment of the conical surface 394 of the tens cone 308 are aligned to collectively present at least a portion of a medication dosage count (for example, in FIG. 24, the count "129" is seen, and in FIG. 25, the count "29" is seen). At this juxtaposition of the indicia bearing surfaces of the units rotational ring 307 and the tens cone 308, those surfaces are tangential to each other at the viewing window 379, which provides a common viewing area for viewing the indicia on the two separate indicia viewing surfaces. As noted above, when the dose counter 302 is disposed within the actuator housing 68 (see FIG. 27), the viewing window 379 is aligned with the viewing window 94 in the side wall 96 of the actuator housing 68, thus presenting the common viewing area for observation by a user. In one embodiment, the common viewing area is generally tangential to a circumferential surface of a cylinder disposed about the axis 322.

Every tenth movement of the units rotational ring 307 results in a movement of the tens cone 308 due to interaction between one of the oblong lugs 368 (on the units rotational ring 307) and one of the spokes 396 (on the tens cone 308). The relationship between the lugs 368 and spokes 396 is illustrated schematically in FIGS. 29A-29D. This direct interaction between the units rotational ring 307 and the tens cone 308 eliminates the need for any transfer gear or other motion translation components between the component bearing ones units indicia (i.e., the units rotational ring 307) and the component bearing tens units indicia (i.e., the tens cone 308). This arrangement requires fewer parts, is more economical in function, and is more compact. In addition, the use of fewer components in a dose counter reduces the number of components that must be manufactured within certain tolerance ranges, and thus reduces the possibility of component incompatibility or inoperabilities due to tolerance stack up.

Figure 29A:
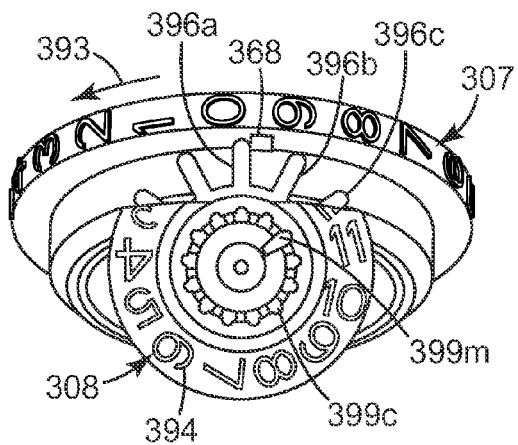
FIGS. 29A, 29B, 29C and 29D represent schematically the interface between the units rotational ring and the tens cone that facilitates rotation of the tens cone as a function of rotation of the units rotational ring.
Figure 29B:
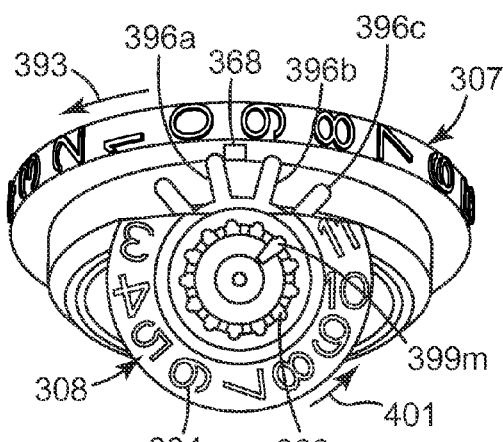
Figure 29C:
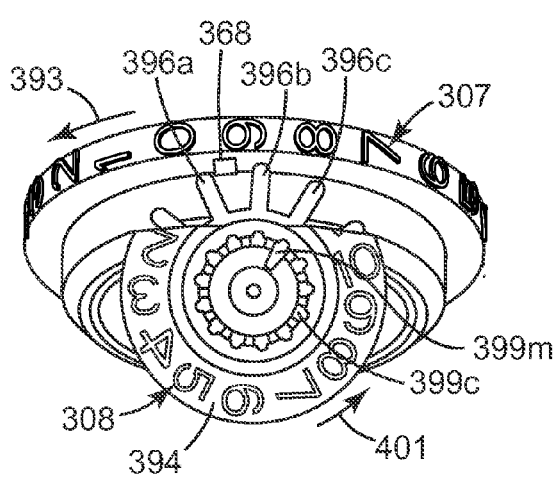
Figure 29D:
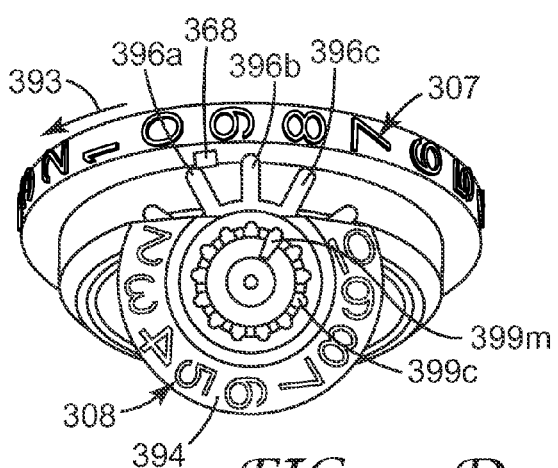

The interaction and sequence for causing the tens cone 308 to change the indicia displayed in the viewing window 379 involves engagement of one of the lugs 368 on the units rotational ring 307 with one of the spokes 396 on the tens cone 308. As seen in FIG. 29A, as the units rotational ring 307 rotates (in direction of arrow 393) one of the lugs 368 thereon eventually moves into engagement with the spoke 396a on the tens cone 308. FIG. 29A illustrates the relationship of the lug 368 and spoke 396a at the time of their initial engagement caused by rotation of the units rotational ring 307 relative to the tens cone 308. As the units rotational ring 307 continues its rotation, the lug 368 pushes the spoke 396a to the left as viewed in FIG. 29B, thereby causing the tens cone 308 to rotate about its axis in a counterclockwise manner (as illustrated by arrow 401). As shown in FIG. 29C, continued rotation of the units rotational ring 307 causes the lug 368 to further push the spoke 396a to the left, thereby causing further counterclockwise rotation of the tens cone 308 about its axis in direction of arrow 401. Eventually, as illustrated in FIG. 29D, the lug 368 pushes the spoke 396a so far that rotation of the tens cone 308 moves the spoke 396a out of the path of the advancing lug 368 (i.e., below the lug 368 as seen in FIG. 29D). Once this happens, further counter clockwise rotational movement of the tens cone 308 stops, and a new tens units number is aligned for observation through the viewing window 379. In an embodiment where the tens units number is rotated to show a count down of the number of dosages remaining, the new tens units number displayed will be a number smaller than the previous number that was displayed.

Rotation of the tens cone 308 relative to the rotation of the units rotational ring 307 occurs each time one of the lugs 368 engages one of the spokes 396. In one embodiment, there are two lugs 368 on the units rotational ring 307, so for every complete rotation of the units rotational ring 307 (which represents twenty ones units numbers) the tens cone 308 is rotated through two tens units numbers. In alternative embodiments, the rotation of the tens cone 308 as a function of rotation of the units rotational ring 307 may be made more frequent or less frequent by providing more or fewer lugs 368 on the units rotational ring 307. In the illustrated embodiment, the conical surface 394 of the tens cone 308 has thirteen tens units numbers bearing arcuate segments, and on its internal surface 395 the tens cone 308 correspondingly has thirteen spokes 396. If more or fewer arcuate number segments are desired to be provided on the tens cone 308, the number of spokes 396 must therefore accordingly be adjusted in a likewise fashion.

Figure 30A:
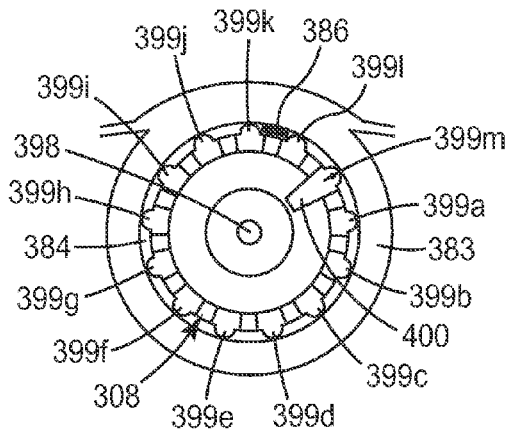
FIGS. 30A, 30B, 30C and 30D represent schematically the interface between the tens cone and a projection on the housing provided to stop rotation of the tens cone.
Figure 30B:
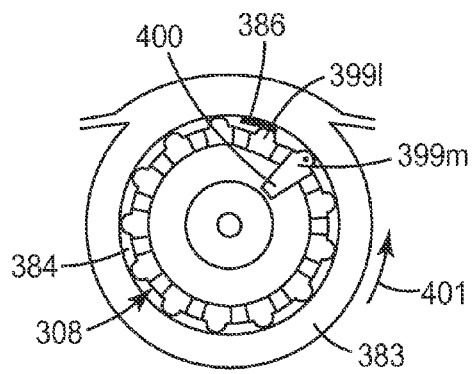
Figure 30C:
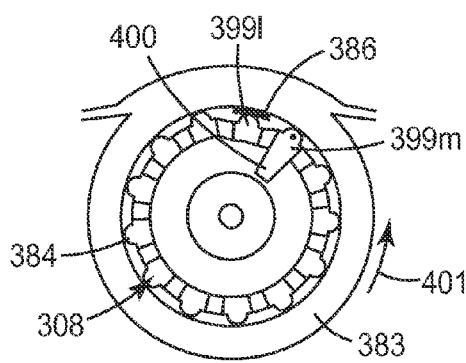
Figure 30D:
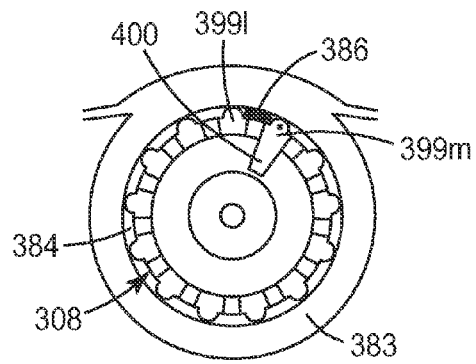
Figure 31:
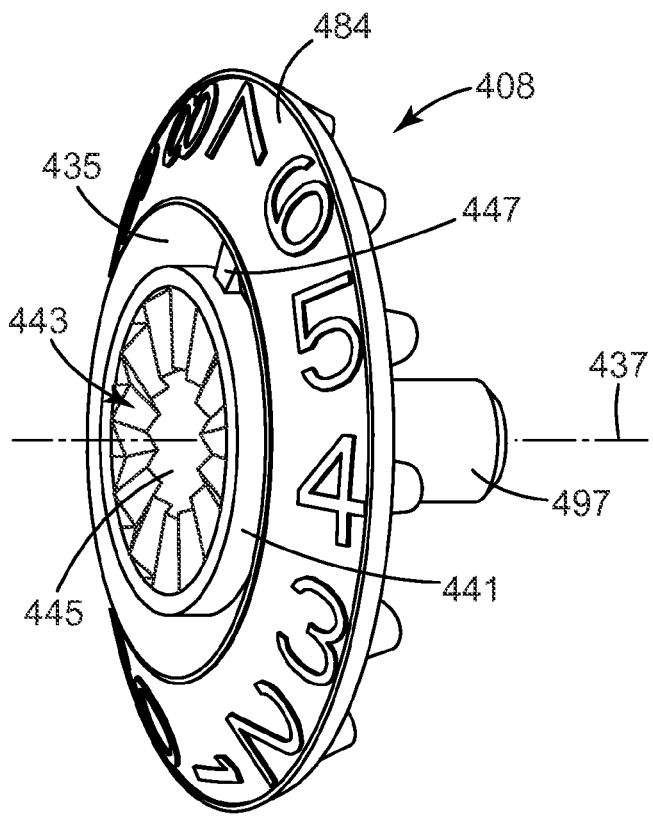
FIG. 31 represents an isometric view of a tens cone of a fourth embodiment of the dose counter of the present invention, as viewed generally from the external or front side thereof.
Figure 32:
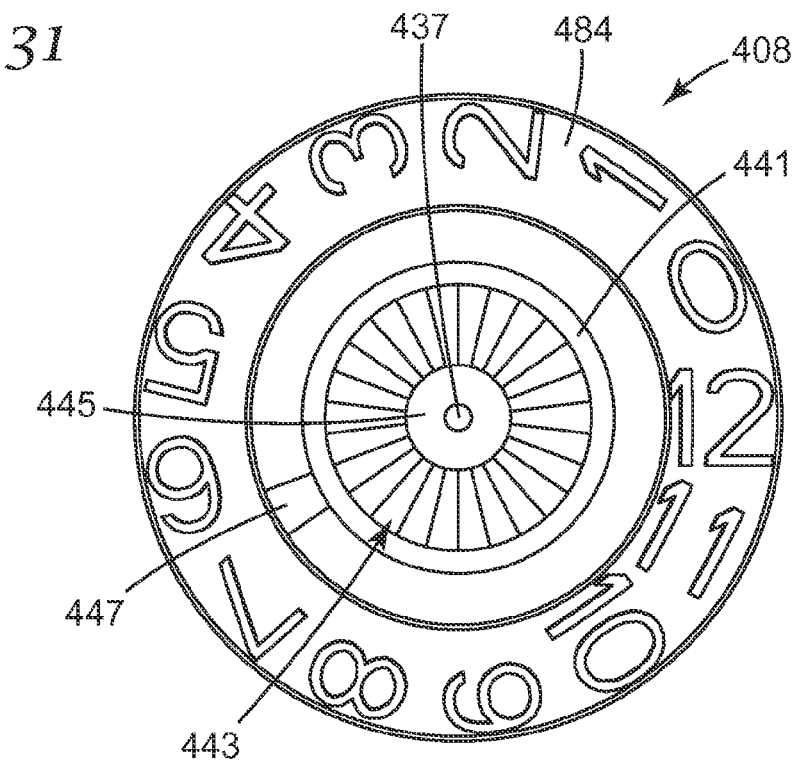
FIG. 32 represents a front or external view of the tens cone of FIG. 31.

The position of the tens cone 308 is maintained as it is indexed through each of its tens units numbers for display by the interaction of the splines 399 and the projection 386 on the housing 309, as illustrated in FIGS. 30A-30D. This arrangement also provides a mechanism for establishing a zero count for the dose counter 302, thus preventing further count down number changes when that zero dosage count is reached. As seen in FIG. 30A, the projection 386 is shaped to extend between adjacent splines 399 (such as between splines 399k and 399l). The sequence of movement shown in FIGS. 30A-30D corresponds generally in position to the sequential movement positions of the tens cone 308 in FIGS. 29A-29D. As seen in FIG. 30B, as the tens cone 308 is rotated in direction of arrow 401 (relative to the conical housing section 383), the spline 399l engages the projection 386 and bends axially inwardly to ride over the projection 386. FIG. 30C illustrates continued movement of the tens cone 308 relative to the projection 386. Once the spline 399l has moved past the projection 386, it snaps back to its original configuration as seen in FIG. 30D.

When the projection 386 reaches the spline 399m, a locking of components occurs. Spline 399m is larger than the other splines, and thus unable to bend radially inwardly upon engagement with the projections 386. This thus locks the tens cone 308 in rotational position relative to the conical housing section 383, and also with respect to further rotation relative to the units rotational ring 307. Once one of the lugs 368 on the units rotational ring 307 again moves into engagement with one of the spokes 396 on the tens cone 308, further rotation of the units rotational ring 307 is prevented. At that point, both the units rotational ring 307 and the tens cone 308 will display a "0" numeral in the viewing window 379. To the extent further medication is present in the aerosol container, it may be dispensed by a user using the aerosol dispensing assembly, but the dose counter 302 will not register any further dosage counts. As an alternative, the aerosol dispensing assembly could be designed to cease dispensing doses of medication once the zero count has been reached, for example by limiting the free movement of the indexer 304.

In essence, the inventive dose counter 302 in the embodiment illustrated in FIGS. 21-30 operates in the following fashion. When a user actuates the inhaler by pushing the aerosol container 70 downwardly into the actuator housing 68, the valve ferrule 110 engages the indexer 304 to push it downwardly. Indexer 304 engages and then causes rotation of the units teeth ring 305. The units rotational ring 307 is coupled rotationally to the units teeth ring 305, so it rotates as well. As the aerosol container 70 reciprocates down and up to complete a single dosage of medication therein, the indexer 304 and units teeth ring 305 also reciprocate down and up relative to the units rotational ring 307. When complete down and up reciprocal movement of the units teeth ring 305 causes the units rotational ring 307 to rotate on its axis 322, the ring 307 has a single ones units count change in position thereof. Rotation of the units rotational ring 307 is translated into rotation of the tens cone 308 by engagement of the lug 368 on the units rotational ring 307 with one of the spokes 396 on the tens cone 308. However, the tens cone 308 is only rotated periodically relative to the units rotational ring 307, to indicate a change in decade of the counts (i.e., the tens cone 308 is only moved once for every ten movements of the units rotational ring 307). Each time the units rotational ring 307 counts ten ones units counts, the tens cone 308 is indexed one position to change the tens units count displayed thereon.

In the illustrated embodiment shown in FIG. 24, a maximum dosage count of "129" medication dosages is shown. This allows for some testing of the aerosol dispensing assembly (e.g., nine initial "tester" counts available with 120 user available dispensing counts remaining) As noted above, changing the frequency or spacing of indicia on the units rotational ring and/or tens cone (along with corresponding changes in the interactive geometry between those components) allows modification of the possible count indicia shown.

A fourth embodiment of the inventive dose counter is illustrated in FIGS. 31-40. This embodiment is referenced as dose counter 402 (see FIGS. 37A and 37B), and is generally similar to the third embodiment, except that the mechanism for preventing reverse movement of the counter components has been modified. The tens cone no longer has splines visible through a circular hole in a conical housing section of the housing. Instead, the tens cone has an annular sawtooth array disposed to engage a beveled protrusion on an inner movable face of the housing.

FIGS. 31-34 illustrate a tens cone 408 of the fourth embodiment dose counter 402. The tens cone 408 has numbers 12 to 0 arranged descending clockwise about an external conical surface 484 of the tens cone 408 when viewed from an apex of the conical surface 484 (i.e., in the sequence 12 11 10 9 8 7 6 5 4 3 2 1 0). The orientation for readability of the numbers is similar to the orientation on the tens cone 8. On the tens cone 408, the conical surface 484 extends only in a band adjacent an outer circumferential edge of the tens cone 408. Concentrically within the band, the tens cone 408 has an annular recess 435 sloped such that the recess 435 is deepest nearest an axis 437 of the tens cone 408. A short cylindrical wall 441 forms an inside wall of the recess 435. Radially within the cylindrical wall 441 is an annular sawtooth array 443 surrounding an axial hole 445. A narrow radial in-fill element 447 bridges the deepest part of the recess 435 between the external conical surface 484 and the cylindrical wall 441, at about the "6 o'clock" position, as indicated by the tens units digits on the external conical surface 484 (see FIG. 32).

Figure 33:
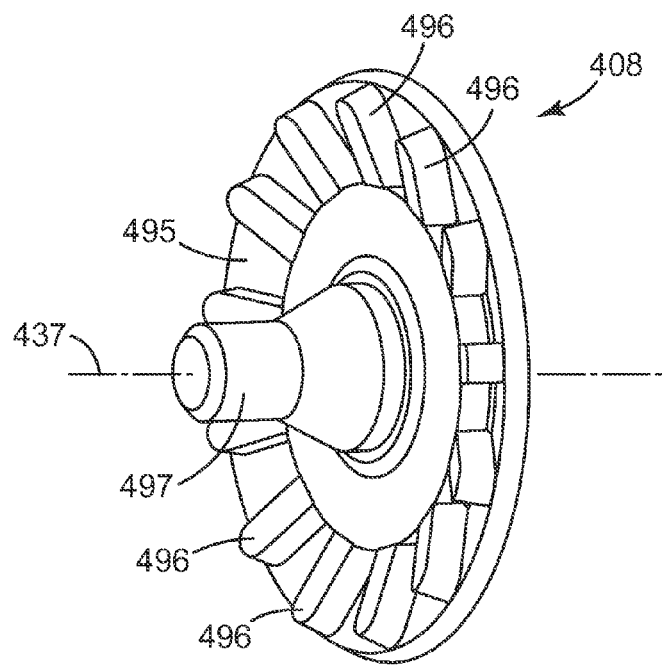
FIG. 33 represents an isometric view of the tens cone of FIG. 31, as viewed generally from an internal or back side thereof.
Figure 34:
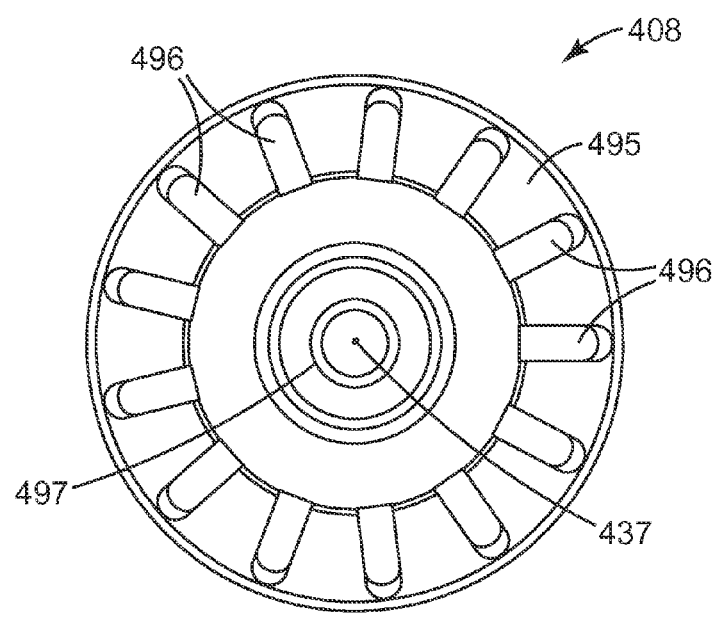
FIG. 34 represents a back or internal side view of the tens cone of FIG. 31.

An internal surface 495 of the tens cone 408 is formed the same as the internal surface 395 of the tens cone 308, bearing radial spokes 496 and a spindle 497 thereon (see FIGS. 33 and 34).

For this fourth embodiment, a housing 409 is provided, which again has a generally cylindrical body 462 with two forward legs 466 extending downwardly therefrom, and a viewing window 472 thereon. Like the housing 309, the housing 409 has a plurality (e.g., three) of doorframe features 476 thereon, shaped similarly and for the same function as the doorframe features 376 of housing 309 (to clip the housing 409 to a lid for the dose counter 402). The housing 409 also has a lateral shelf 481 therein, which has a central hole 482 therethrough for accommodating the nozzle block of the actuator housing.

Figure 37A:
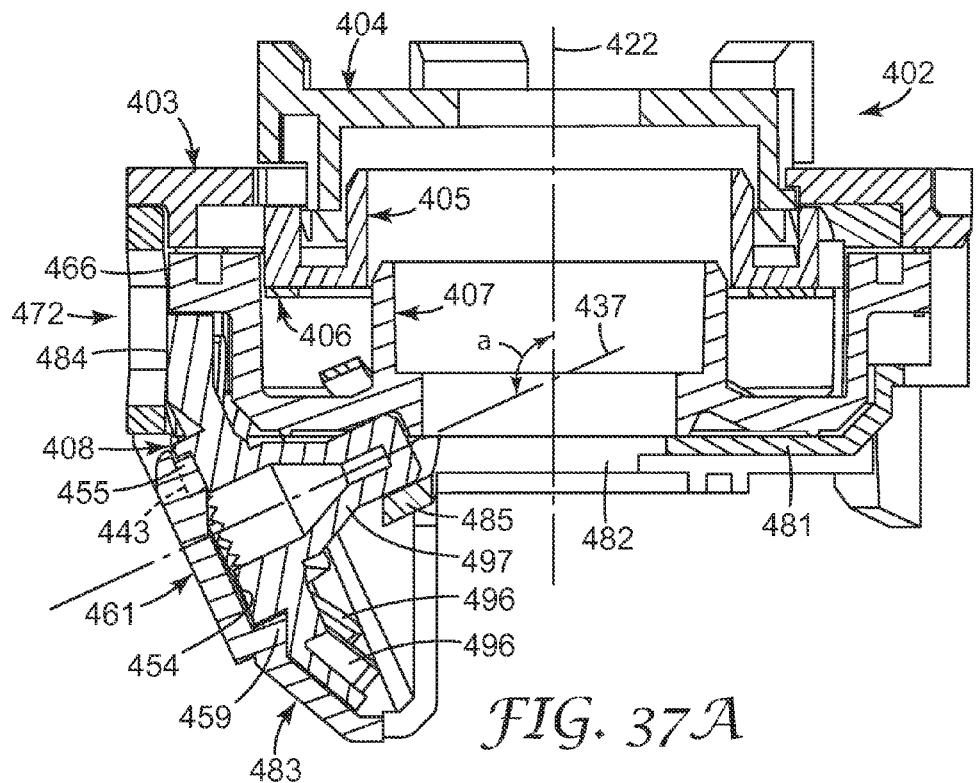
FIGS. 37A and 37B represent sectional views of the assembled dose counter of the fourth embodiment, embodying the tens cone of FIGS. 31-34 and the housing of FIGS. 35 and 36.
Figure 37B:
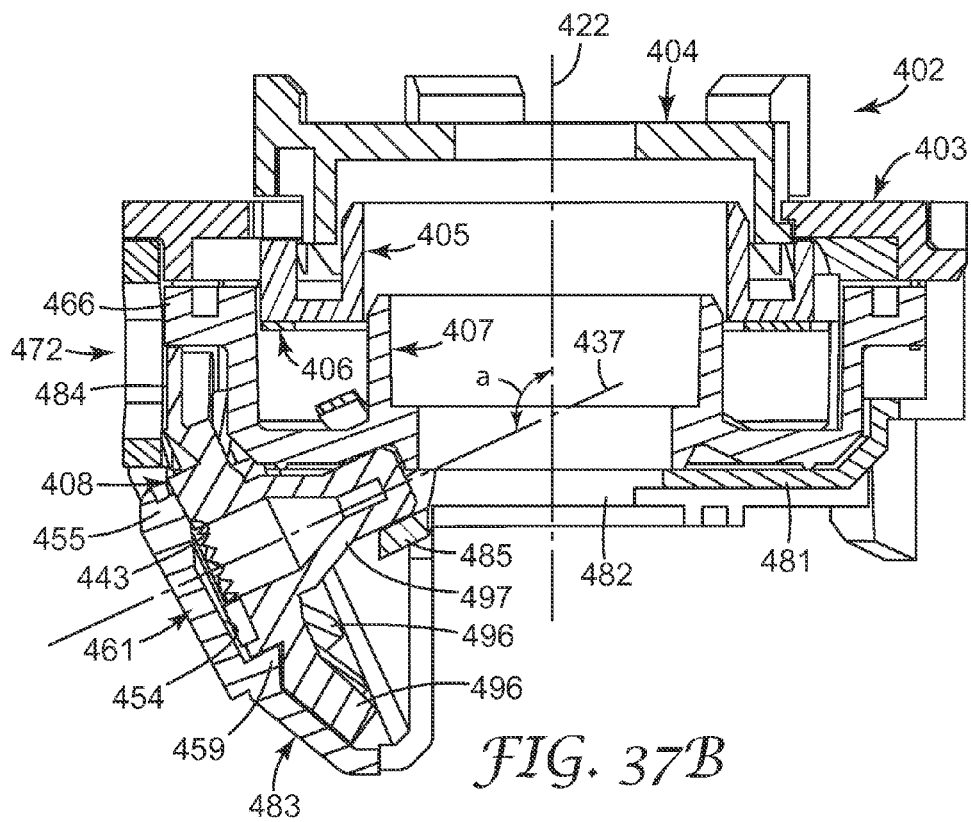

On a rear side thereof (defined as including the viewing window 472), the housing 409 has a conical housing section 483 extending downwardly therefrom and designed to accommodate the tens cone 408 therein, as seen in FIGS. 37A and 37B. The tens cone 408 is aligned to rotate in a stable manner about an axis directed diagonally forward and upward from the rear of the housing 409. The relationship of the axis 437 of the tens cone 408 relative to an axis 422 of the housing 409 in this embodiment is similar to that illustrated and stated for the those axes of the same components of the third embodiment (compare FIGS. 37A and 37B with FIG. 26). The conical housing section 483 is shaped internally to generally conform to the external side of the tens cone 408 except within the cylindrical wall 441 and recess 435 thereof. The conical housing section 483 has an inner planar face 454 that is flush with a top surface which corresponds to the cylindrical wall 441, except for a beveled protrusion 455 designed to fit between the teeth of the sawtooth array 443. That portion 457 of the conical housing section 483 that corresponds to the recess 435 of the tens cone 408 has a protruding ramp 459 directed axially inwards and designed to abut the in-fill element 447 when the tens cone 408 has rotated far enough to bring the ramp 459 and in-fill element 447 into engagement. This ultimately corresponds to the zero position for the counter elements of the dose counter 402.

FIGS. 37A and 37B illustrate the tens cone 408, housing 409 and other components of the dose counter 402. Those other components conform generally to the configuration of like components in the embodiment illustrated in FIGS. 21-30. Thus, a lid 403 corresponds to lid 303, an indexer 404 corresponds to indexer 304, a units teeth ring 405 corresponds to units teeth ring 305, a compression spring 406 corresponds to compression ring 306, and a units rotational ring 407 corresponds to units rotational ring 307. The lid 403, indexer 404, units teeth ring 405, spring 406 and units rotational ring 407 are assembled with the tens cone 408 and housing 409 as illustrated in FIGS. 37A and 37B. This assembly, other than the relationship between the tens cone 408 and housing 409, is generally identical to that illustrated in the embodiment of FIGS. 21-30. Indexing of the units rotational ring 407 is accomplished in the same manner in the embodiment of FIGS. 31-40 as in the embodiment of FIGS. 21-30. In addition, indexing of the tens cone 408 is accomplished in the same manner in the embodiment of FIGS. 31-40 as in the embodiment of FIGS. 21-30. The spokes 496 of the tens cone 408 are periodically engaged and advanced by a lug 468 on the units rotational ring 407, in the fashion illustrated schematically by FIGS. 29A-29D (and as illustrated for like structure in FIGS. 39A-39E).

An outer cylindrical surface 466 bears ones units indicia of the units rotational ring 407, and is viewable through the viewing window 472. The tens cone 408 bears tens units indicia on the external surface 484 thereof. When assembled in the dose counter 402, the indicia on the surface 466 and the surface 484 are tangentially aligned within the viewing window 472, at the common viewing area, to present a representative dosage count to a user. The indicia bearing surfaces are aligned like those of like structure in the earlier described embodiments.

Figure 35:
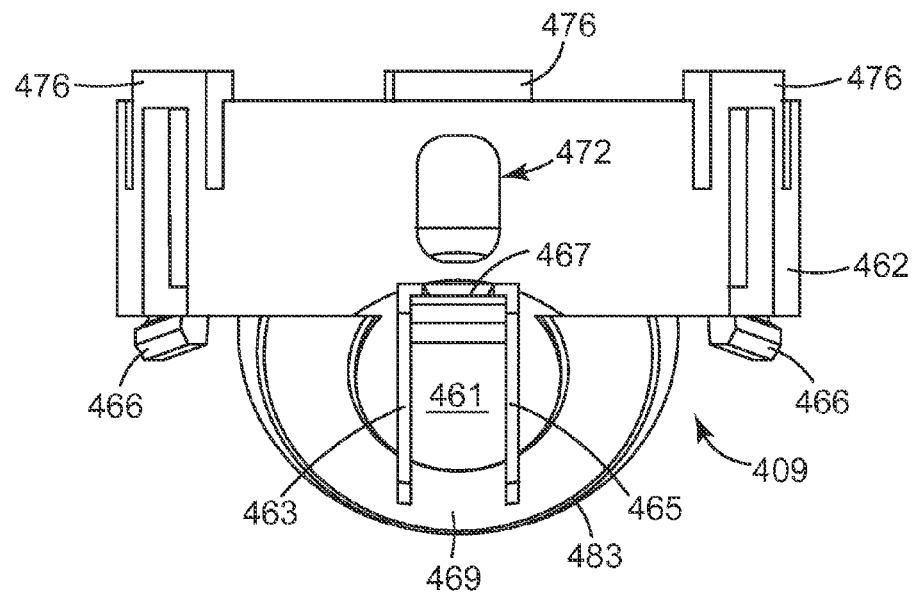
FIG. 35 represents a rear elevational view of a housing adapted for use in connection with the tens cone of FIGS. 31-34.
Figure 36:
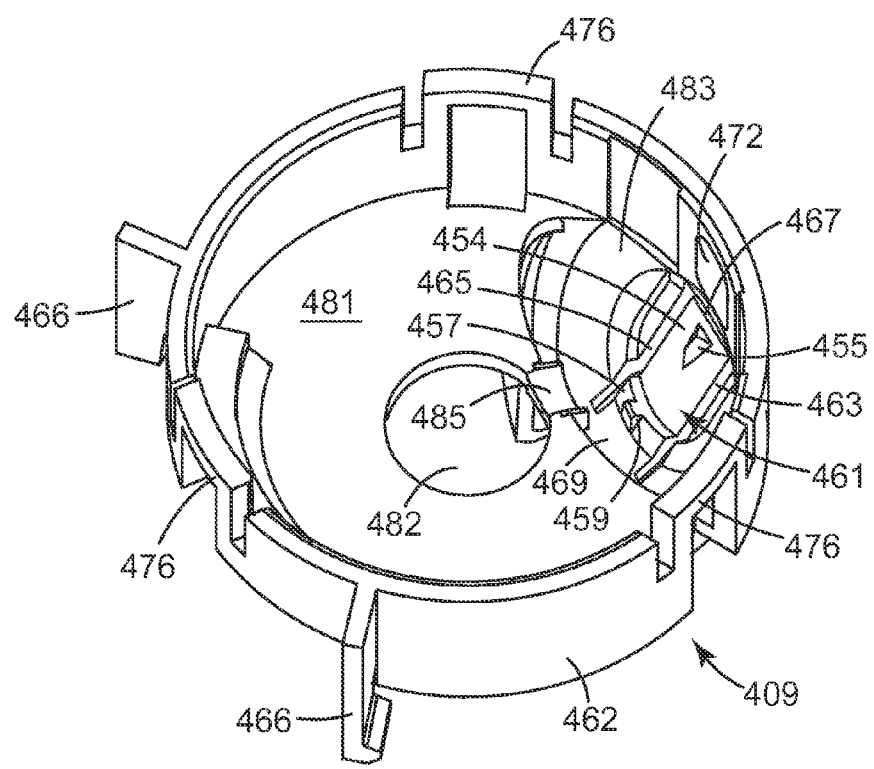
FIG. 36 represents an isometric view of the housing of FIG. 35, as viewed generally from the top thereof.

As seen in FIGS. 35 and 36, the conical housing section 483 has a center pivoting section 461 which is separated from the conical housing section 483 along its side edges 463 and 465 and its top edge 467. This configuration thus allows the center pivoting section 461 to flex outwards slightly from a bottom portion 469 thereof connected to the conical housing section 483 to allow the beveled protrusion 455 to ride over the sawtooth array 443 when sufficient force is applied to cause rotation of the tens cone 408.

Figure 38A:
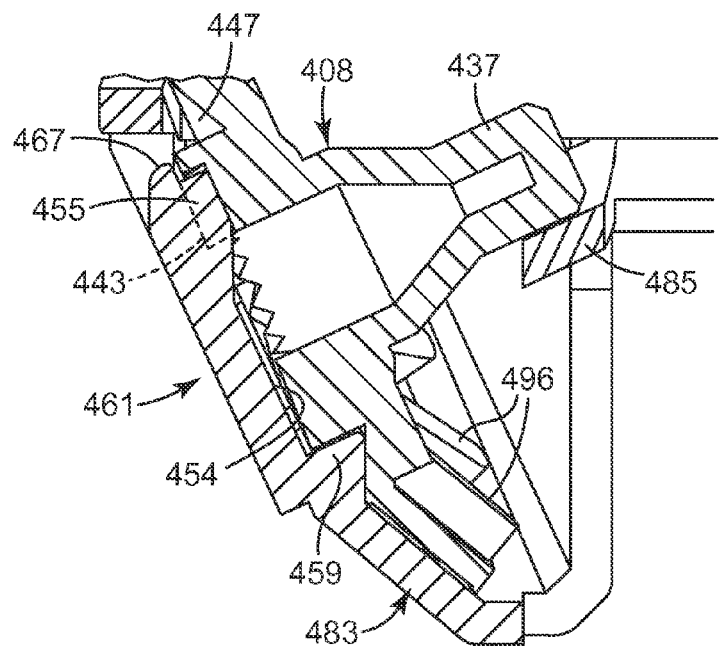
FIGS. 38A and 38B represent enlarged partial sectional views of FIGS. 37A and 37B respectively.
Figure 38B:
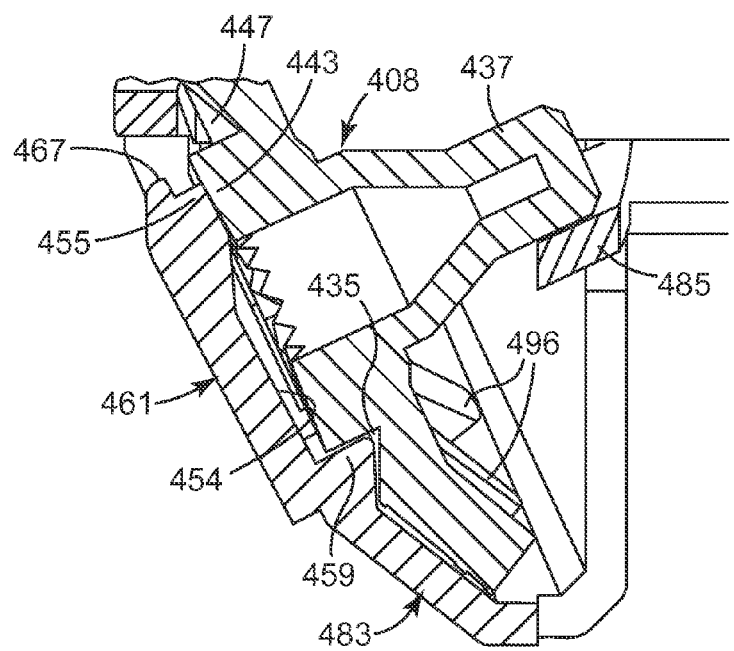
Figure 39A:
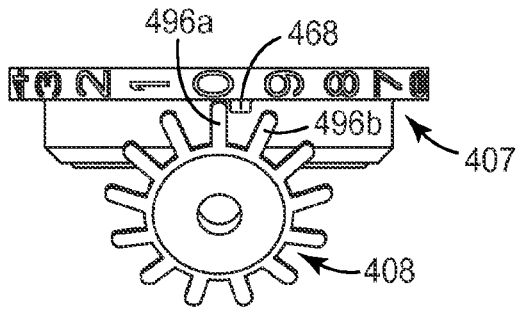
FIGS. 39A, 39B, 39C, 39D and 39E represent the interface between the tens cone of FIGS. 31-34 and an associated units rotational ring.
Figure 39B:
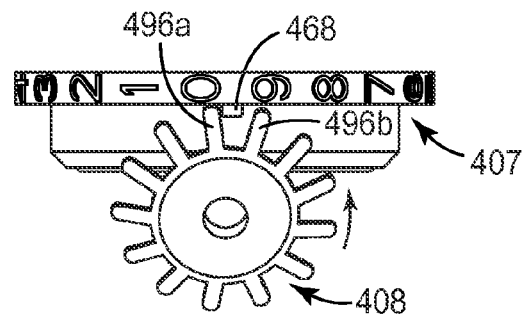
Figure 39C:
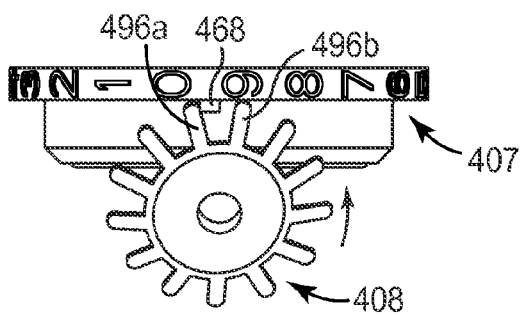
Figure 39D:
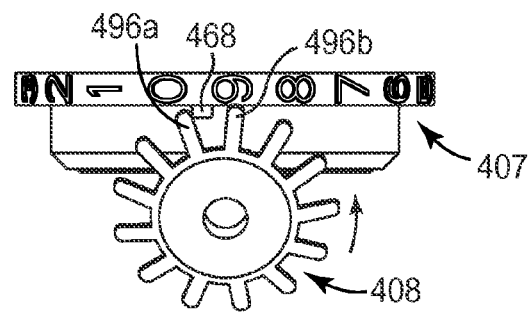
Figure 39E:
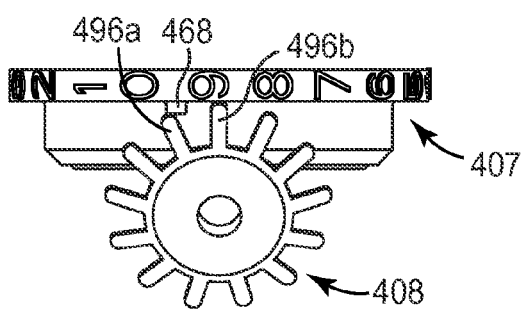
Figure 40A:
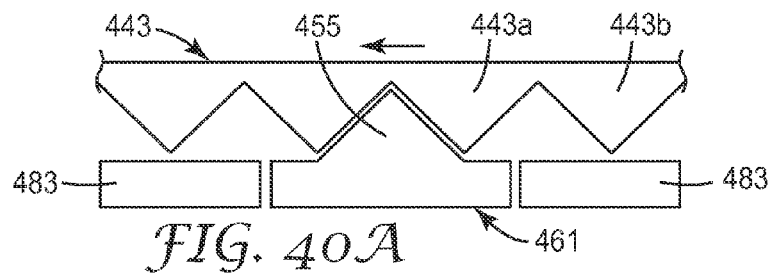
FIGS. 40A, 40B, 40C, 40D and 40E represent schematically the interface between an annular sawtooth array of teeth on the tens cone of FIGS. 31-34 and an associated protrusion on the housing of FIGS. 35 and 36.
Figure 40B:
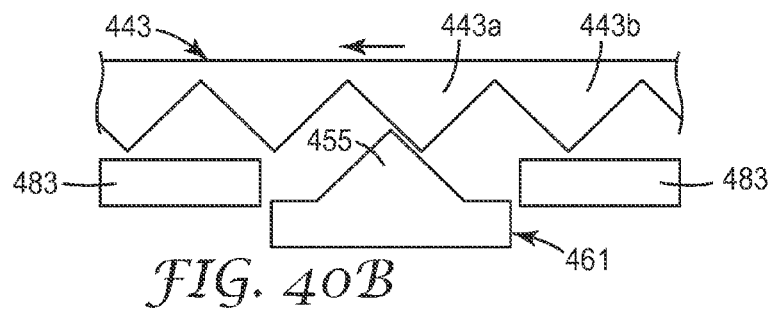
Figure 40C:
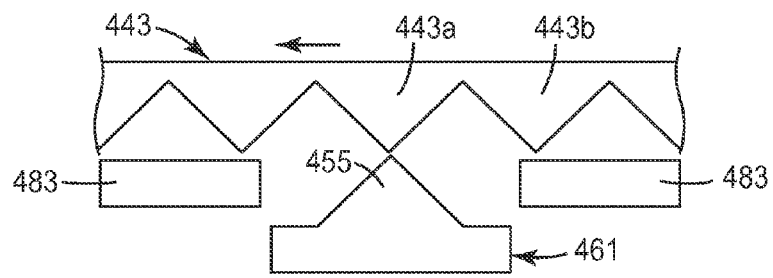
Figure 40D:
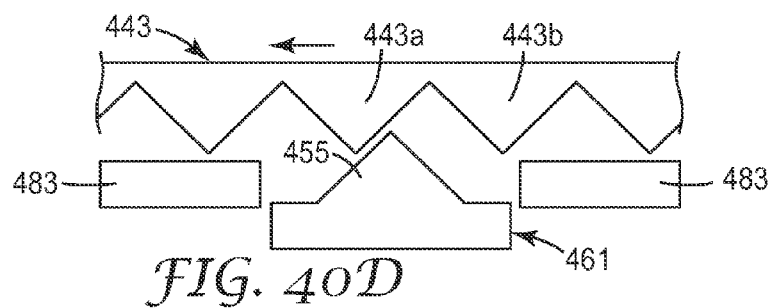
Figure 40E:
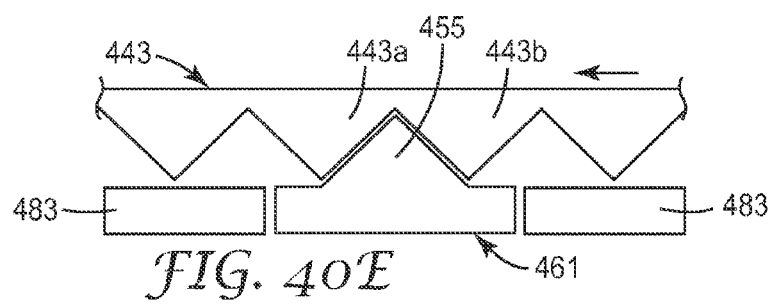

FIGS. 40A-40E illustrate schematically and sequentially the interaction between the beveled protrusion 455 on the center pivoting section 461 of the conical housing section 483 of the housing 409. FIG. 40A shows the relationship between the beveled protrusion 455 and the teeth of the sawtooth array 443 when the tens cone 408 is fixed in place rotationally to display one of the tens units numbers thereon (such as aligned in FIGS. 37A and 38A). As the tens cone 408 is rotated counterclockwise to change the tens units number displayed in the viewing window 472, a tooth 443a of the sawtooth array 443 moves to the left (as seen in FIG. 40B) and pushes, ramp on ramp, against the beveled protrusion 455, causing it to bend outwardly (downwardly as viewed in FIG. 40B). When the apex of tooth 443a encounters the apex of the beveled protrusion 455, the center pivoting section 461 is bent at its most outward position relative to the conical housing section 443, as seen in FIG. 40C (and as also seen in FIGS. 37B and 38B). Continued counterclockwise movement of the tens ring 408 causes the tooth 443a of the sawtooth array 443 to move past the beveled protrusion 455, ramp on ramp, thus reducing the extent of interference and allowing the center pivoting section 461 to flex back toward the tens cone 408 (or upwardly, as viewed in FIG. 40D). Once a tens units numeral has been changed by rotation of the tens unit 408, the beveled protrusion 455 is seated between the tooth 443a and a next tooth 443b of the sawtooth array 443, thus preventing further forward or reverse movement of the tens cone 408 (until it is again caused to be rotated as a function of the rotation of the units rotational ring 407).

Eventually, the in-fill element 447 on the tens cone 408 is rotated into abutment with the ramp 459 on the housing 409. Following this point of abutment (when the units rotational ring is showing a 9 as its ones units digit), as the units rotational ring 408 completes its last ten ones units counts, the protruding oblong lug 468 can no longer move a radial spoke 496 on the tens cone 408. Thus, the units rotational ring 407 will also be unable to advance beyond 0 as its ones units digit, once the tens cone 408 has reached 0 as its tens units numeral, despite further actuations of the inhaler.

In essence, the inventive dose counter 402 in the embodiment illustrated in FIGS. 31-40 operates in the following fashion. When a user actuates the inhaler by pushing the aerosol container downwardly into the actuator housing, the valve ferrule engages the indexer 404 to push it downwardly. Indexer 404 engages and then causes rotation of the units teeth ring 405. The units rotational ring 407 is coupled rotationally to the units teeth ring 405, so it rotates as well. As the aerosol container reciprocates down and up to complete a single dosage of medication therein, the indexer 404 and units teeth ring 405 also reciprocate down and up relative to the units rotational ring 407. When complete up and down reciprocal movement of the units teeth ring 405 causes the units rotational ring 407 to rotate on its axis 422, the ring 407 has a single ones units count change in position thereof. Rotation of the units rotational ring 407 is translated into rotation of the tens cone 408 by engagement of the lug 468 on the units rotational ring 407 with one of the spokes 496 on the tens cone 408. However, the tens cone 408 is only rotated periodically relative to the units rotational ring 407, to indicate a change in decade of the count (i.e., the tens cone 408 is only moved once for every ten movements of the units rotational ring 407). Each time the units rotational ring 407 counts ten ones units counts, the tens cone 408 is indexed one position to change the tens units counts displayed thereon.

A fifth embodiment of the inventive dose counter is illustrated in FIGS. 41-47. This embodiment is referenced as dose counter 502 (see FIGS. 45A and 45B), and is generally similar to the third embodiment, except that the mechanism for preventing reverse movement of the counter components has been modified. The tens cone no longer has splines visible through a circular hole in a conical housing section of the housing. Instead, the tens column has an annular array of teardrop shaped recesses disposed to engage a teardrop shaped protrusion on an inner face of the housing. In addition, the tens cone of this embodiment and its associated housing and units rotational ring are configured to allow a rocking motion of the tens cone as it is rotated to engage and disengage one of its teardrop shaped recesses with the teardrop shaped protrusion on the housing.

Figure 41:
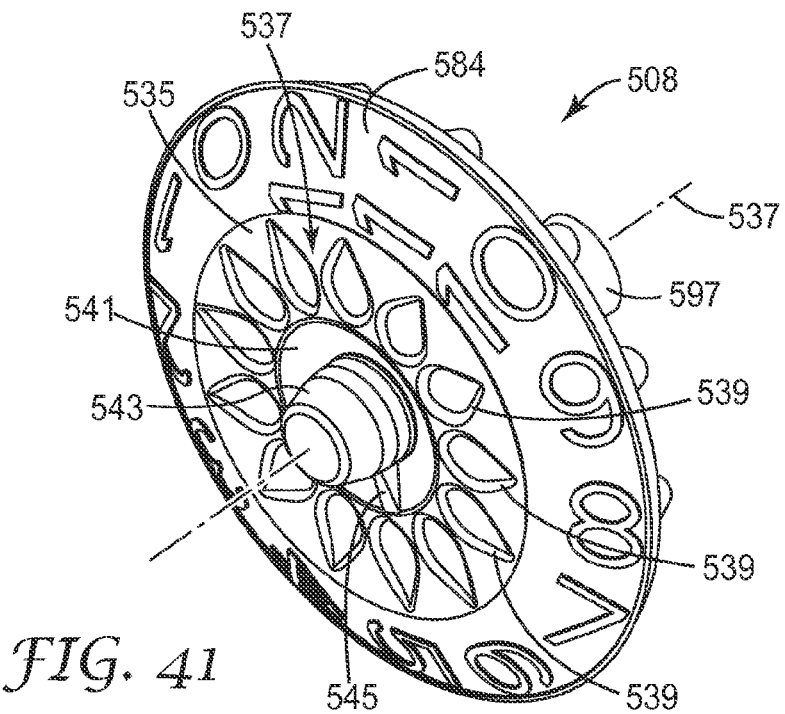
FIG. 41 represents an isometric view of a tens cone of a fifth embodiment of the dose counter of the present invention, as viewed generally from the external or front side thereof.
Figure 42:
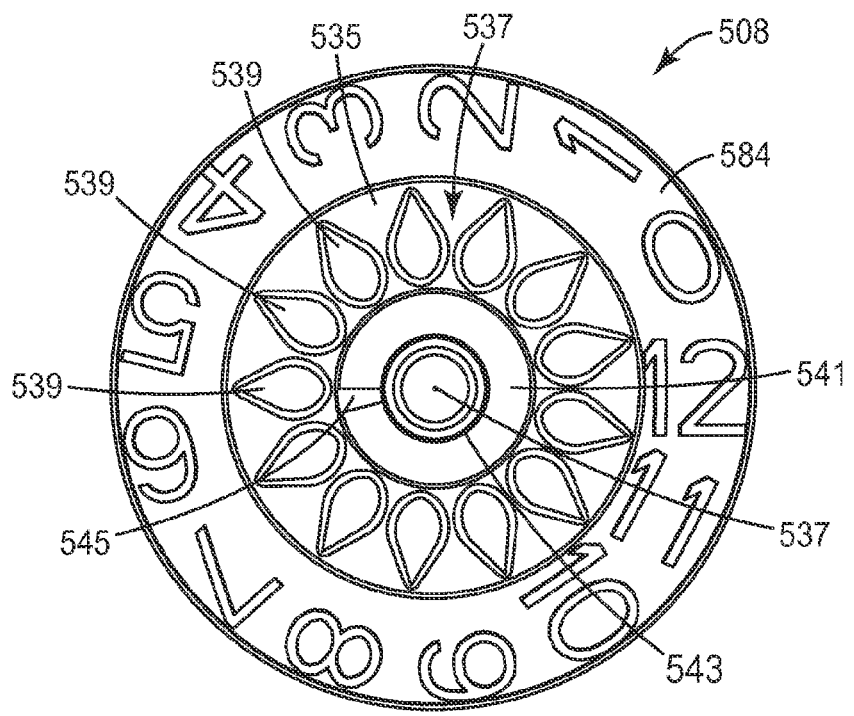
FIG. 42 represents a front or external view of the tens ring of FIG. 41.
Figure 43:
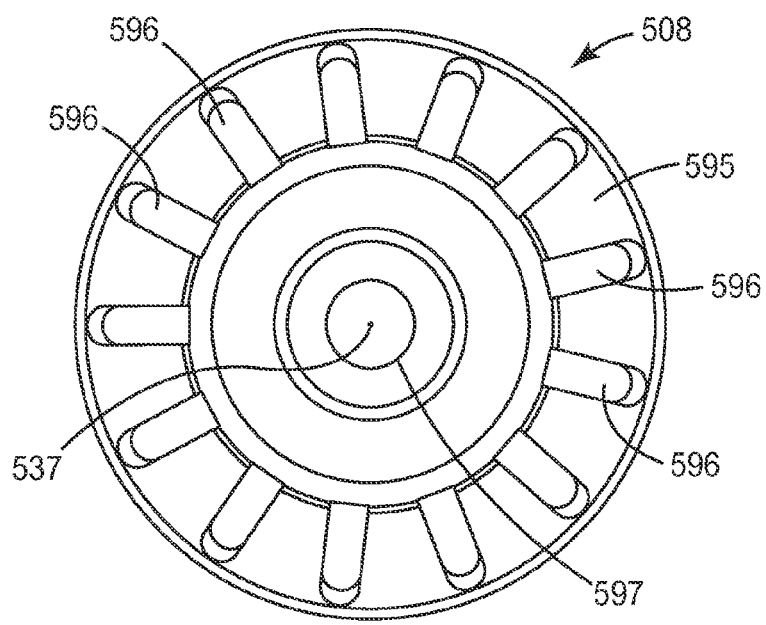
FIG. 43 represents a back or internal view of the tens cone of FIG. 41.

FIGS. 41-43 illustrate a tens cone 508 of the fifth embodiment dose counter 502. The tens cone has numbers 12 to 0 arranged descending clockwise about an external conical surface 584 of the tens cone 508 when viewed from an apex of the conical surface 584 (i.e., in the sequence 12 11 10 9 8 7 6 5 4 3 2 1 0). The orientation for readability of the numbers is similar to the orientation on the tens cone 8. On the tens cone 508, the conical surface 584 extends only in a band adjacent an outer circumferential edge of the tens cone 508. Concentrically within the band, the tens cone 508 has an annular surface 535 which adjoins the conical surface 584 and extends perpendicular to an axis 537 of rotation for the tens cone 508. An annular array 537 of teardrop shaped recesses 539 are disposed on the annular surface 535. Each teardrop shaped recess 539 has its narrower end pointed radially outwardly from the axis 537 of the tens cone 508. Concentrically within the annular surface 535, the tens cone 508 has an annular recess 541 that is sloped such that the recess 541 is deepest nearest the axis 537 of the tens cone 508. The annular recess 541 abuts and surrounds a protruding boss 543 of the tens cone 508, with the boss 543 being coaxial with the axis 537. A narrow radial in-fill element 545 bridges the recess 541 between the annular surface 535 and the boss 543, at about the "6 o'clock" position, as indicated by the tens units digits on the external conical surface 584.

An internal surface 595 of the tens cone 508 is formed the same as the internal surface 395 of the tens cone 308 (and the same as the internal surface 495 of the tens cone 408), bearing radial spokes 596 and a spindle 597 thereon (see FIG. 43).

For the fifth embodiment, a housing 509 is provided, which again has a generally cylindrical body 562 with two forward legs 566 extending downwardly therefrom, and a viewing window 572 thereon. Like the housing 309, the housing 509 has a plurality (e.g., three) of doorframe features 576 thereon, shaped similarly and for the same function as the doorframe features 376 of housing 309 (to clip the housing 509 to a lid for the dose counter 502). The housing 509 also has a lateral shelf 581 therein, which has a central hole 582 therethrough for accommodating the nozzle block of the actuator housing.

Figure 44:
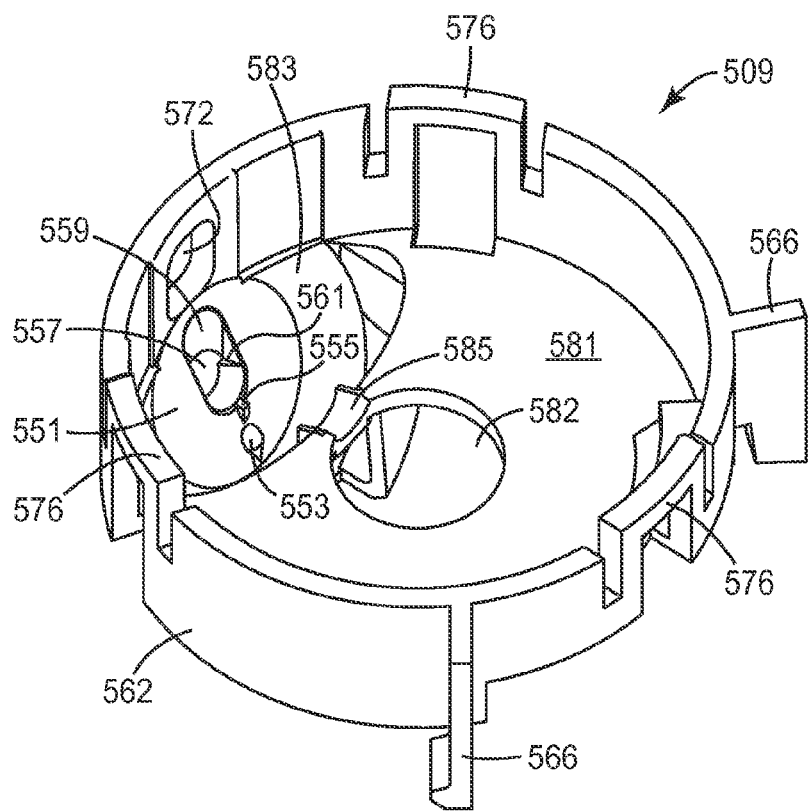
FIG. 44 represents an isometric view of a housing for the dose counter of the fifth embodiment of the present invention, as viewed generally from above.
Figure 45A:
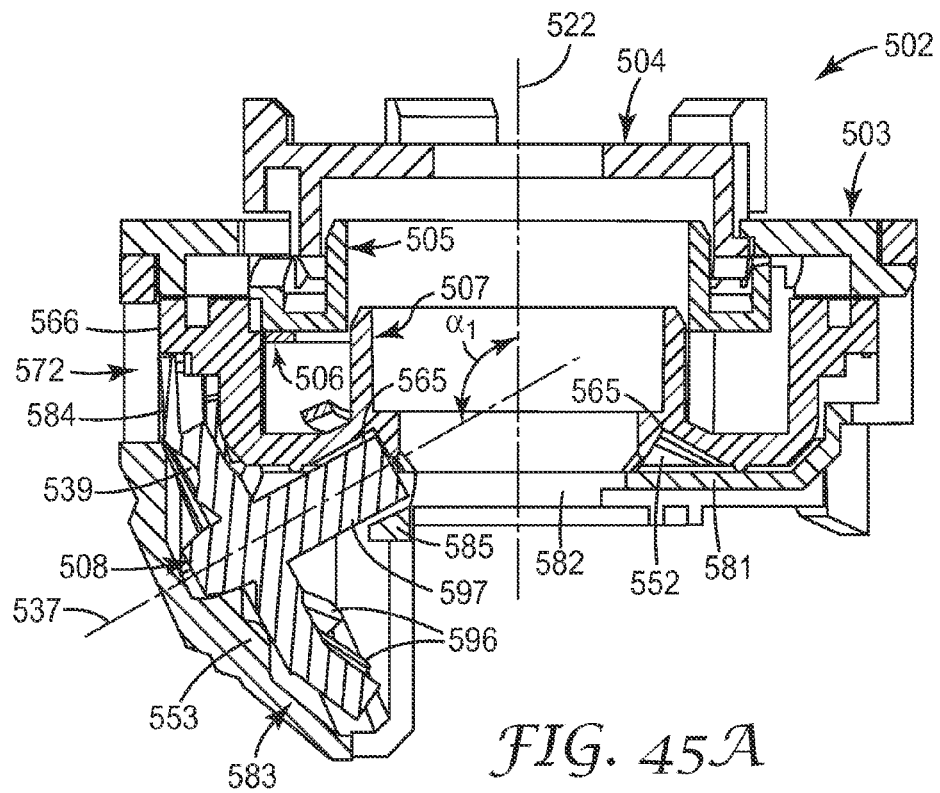
FIGS. 45A and 45B represent a sectional view of the assembled dose counter of the fifth embodiment, with the lateral section for each FIG. taken through the viewing window thereof, and showing the tens cone in two different orientations relative to the housing.
Figure 45B:
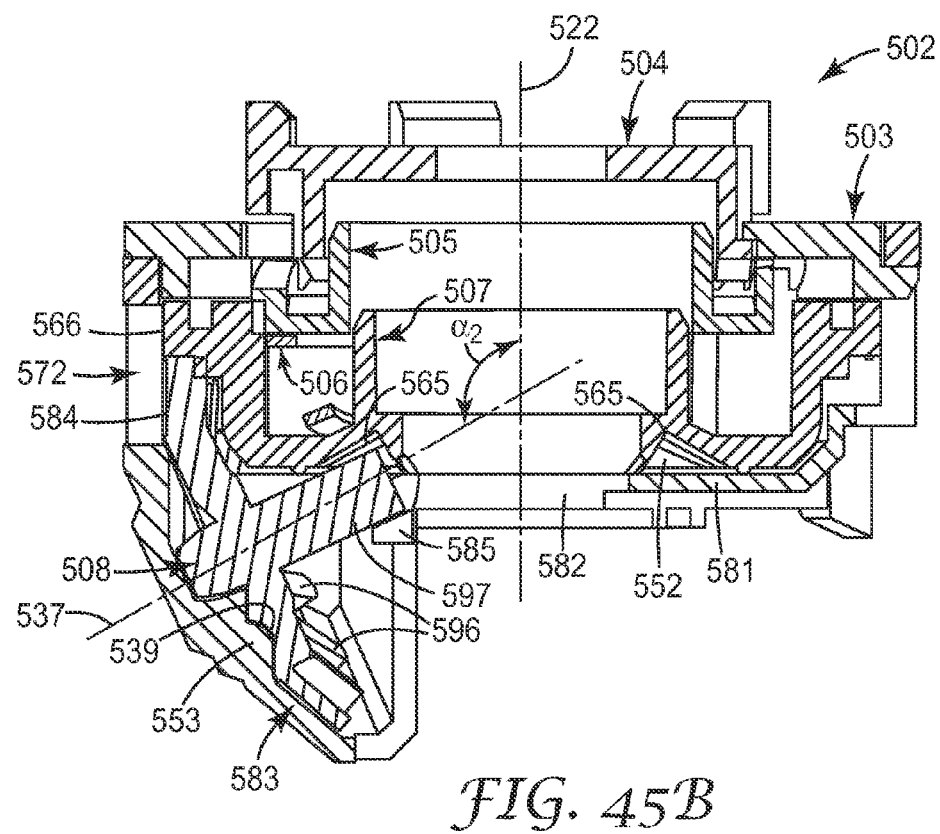

On a rear side thereof (defined as including the viewing window 572), the housing 509 has a conical housing section 583 extending downwardly therefrom and designed to accommodate the tens cone 508 therein, as seen in FIGS. 45A and 45B. The tens cone 508 is aligned to rotate generally about an axis directed diagonally forward and upward from the rear of the housing 509. The relationship of the axis 537 of the tens cone 508 relative to an axis 522 (see FIGS. 45A and 45B) of the housing 409 in this embodiment is similar to that illustrated and stated for those axes of the same components of the third embodiment (compare FIGS. 45A and 45B with FIG. 26). However, as explained below, during rotation of the tens cone 508, it wobbles or rocks relative to the housing 509, so that its axis 537 changes slightly in orientation relative to the axis 522 of the housing 509 (such as illustrated by comparison of angle $\alpha_1$ in FIG. 45A to angle $\beta_2$ in FIG. 45B, wherein $\alpha_1$ is greater than $\alpha_2$). The conical housing section 583 is shaped internally to generally conform to the external side of the tens cone 508 except within the annular surface 535 and recess 541 thereof. As best seen in FIG. 44, the conical housing section 583 has a generally planar surface 551 that corresponds to the annular surface 535 and recess 541 of the tens cone 508. A teardrop shaped protrusion 553 extends inwardly from the planar surface 551 at the lowest point corresponding to the annular surface 535 of the tens cone 508, and is shaped to conform to each one of the thirteen teardrop shaped recesses 539 on the tens cone 508. A ramp 555 also projects inwardly from the planar surface 551, radially inwardly from the teardrop shaped protrusion 553 and circumferentially offset therefrom. The ramp 555 is designed to project inwardly sufficient to abut the in-fill element 545 when the tens cone 508 has rotated far enough to bring the ramp 555 and in-fill element 545 into engagement. This corresponds to the zero position for the counter elements of the dose counter 502. The conical housing section 583 also has a hole 557 shaped to accommodate the boss 597 of the tens cone 508. Above the hole 557, a portion of the conical housing section 583 has a diagonal cutout 559 to facilitate assembly of the tens cone 508 and the housing 509. The cutout 559 and hole 557 interface so that the diameter of the boss 543 of the tens cone 508 must be pushed past a slightly necked region 561 in the conical housing section 583 during assembly, so that the boss 543 clips into place in the housing 509 upon assembly. Like the housing 309, the conical housing section is also provided with a gutter portion 585 for support of the spindle 597 of the tens cone 508.

Figure 47:
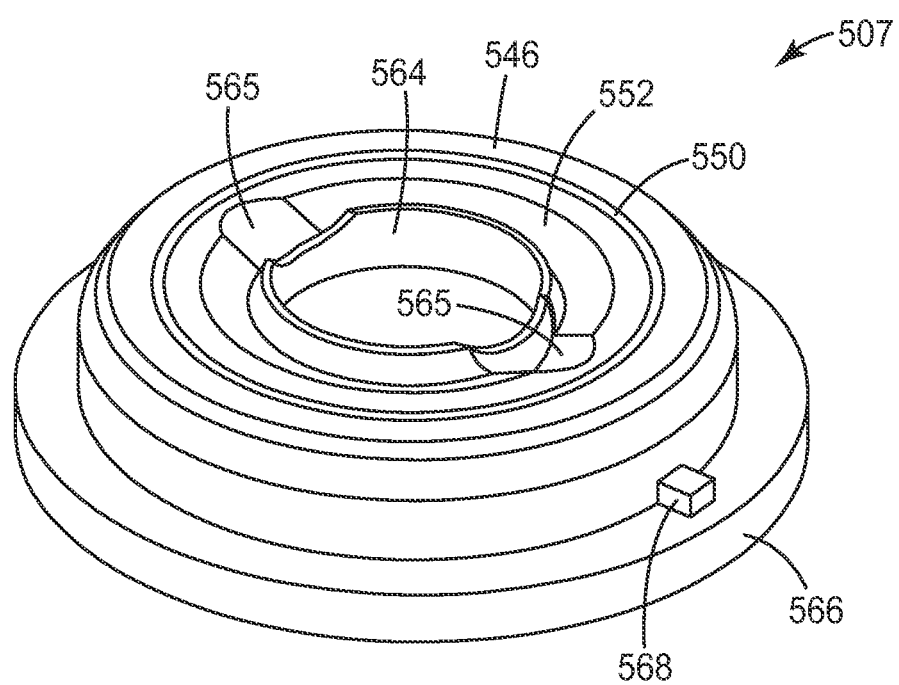
FIG. 47 represents an isometric view of the units rotational ring of FIGS. 46A, 46B, and 46C, viewed generally from a bottom side thereof.

FIGS. 45A and 45B illustrate the tens cone 508, housing 509 and other components of the dose counter 502. These other components conform generally to the configuration of like components in the embodiment illustrated in FIGS. 21-30 except for a revision to the underside of the units rotational ring 507. As seen in FIG. 47, the units rotational ring 507 has an annular base 546 at a bottom thereof. A circumferential rib 550 is disposed on the annular base 546. A circumferential groove 552 is also provided on a bottom surface of the annular base 546, coaxial within the rib 550. The groove 542 is provided to accommodate the spindle 597 of the tens cone 508, at all rotational positions of the units rotational ring 507 with respect to the tens cone 508. In this embodiment, however, the groove 552 has two diametrically opposed smoothly radially scooped deeper recessed regions 565 that extend radially slightly beyond the groove 552 and radially inwardly past the groove 552 and into a cylindrical section 564 of the units rotational ring 507. The recessed regions 565 are designed to allow the spindle 597 of the tens cone 508 to move to a temporary off-axis position while registering a change in the tens units number count, as explained below.

As noted above, the other components of the dose counter 502 conform generally to the configuration of like components in the embodiment illustrated in FIGS. 21-30. Thus, a lid 503 corresponds to lid 303, and indexer 504 corresponds to indexer 304, a units teeth ring 505 corresponds to units teeth ring 305, and a compression spring 506 corresponds to compression ring 306. The lid 503, indexer 504, units teeth ring 505, spring 506 and units rotational ring 507 are assembled with the tens cone 508 and housing 509 as illustrated in FIGS. 45A and 45B. This assembly, other than the relationship of the tens cone 508 with the units rotational ring 507 and the housing 509, is generally identical to that illustrated in the embodiment of FIGS. 21-30. Indexing of the units rotational ring 507 is accomplished in the same manner in the embodiment of FIGS. 41-47 as in the embodiment of FIGS. 21-30. In addition, indexing of the tens cone 508 is accomplished in the same manner in the embodiment of FIGS. 41-47 as in the embodiments of FIGS. 21-30. The spokes 596 of the tens cone 508 are periodically engaged and advanced by a lug 568 (see FIG. 47) on the units rotational ring 507, in the fashion illustrated schematically by FIGS. 29A-29D (and as illustrated for like structure in FIGS. 39A-39E).

An outer cylindrical surface 566 bears ones units indicia of the units rotational ring 507, and is viewable through the viewing window 572. The tens cone 508 bears tens units indicia on the external surface 584 thereof. When assembled in the dose counter 502, the indicia on the surface 566 and the surface 584 are tangentially aligned within the viewing window 572, at the common viewing area, to present a representative dosage count to a user. The indicia bearing surfaces are aligned like those of like structure in the earlier described embodiments.

As illustrated in FIGS. 45A and 45B (and in FIGS. 46A-46C), the tens cone 508 rocks or moves off the axis as it indexes from displaying one tens units number in the viewing window 572 to a next tens units number. When the lug 568 of the units rotational ring 507 engages one of the radial spokes 596 of the tens cone 508, the tens cone 508 is caused to rotate about its axis 537. This rotation becomes an off-axis movement as the teardrop shaped protrusion 553 rides out of whatever teardrop shaped recess 539 it currently is in. The recessed region 565 that the spindle 597 of the tens cone 508 is in allows the spindle 597 of the tens cone 508 to swivel off-axis, making such rotary off-axis movement of the tens cone 508 possible. As rotation of the tens cone 508 is completed as a function of rotation of the units rotational ring 507, a next teardrop shaped recess 539 comes into registration with the teardrop shaped protrusion 553 on the conical housing section 583. As the units rotational ring 507 continues its rotation, the recessed region 565 is moved out of engagement with the spindle 537, and the spindle again rides in the groove 552 that bears against the spindle 597 and pushes it back on axis (where it remains for the next 9 ones units digits counts of the units rotational ring 507).

Figure 46A:
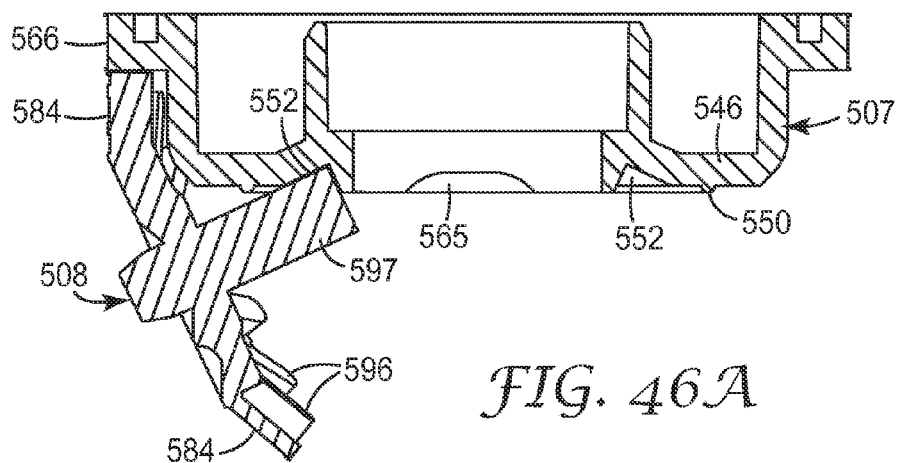
FIGS. 46A, 46B and 46C represent sectional views of the tens cone and an associated units rotational ring of the fifth embodiment, illustrating sequential orientations of the tens cone relative to the units rotational ring during rotation of units rotational ring and rotation of the tens cone.
Figure 46B:
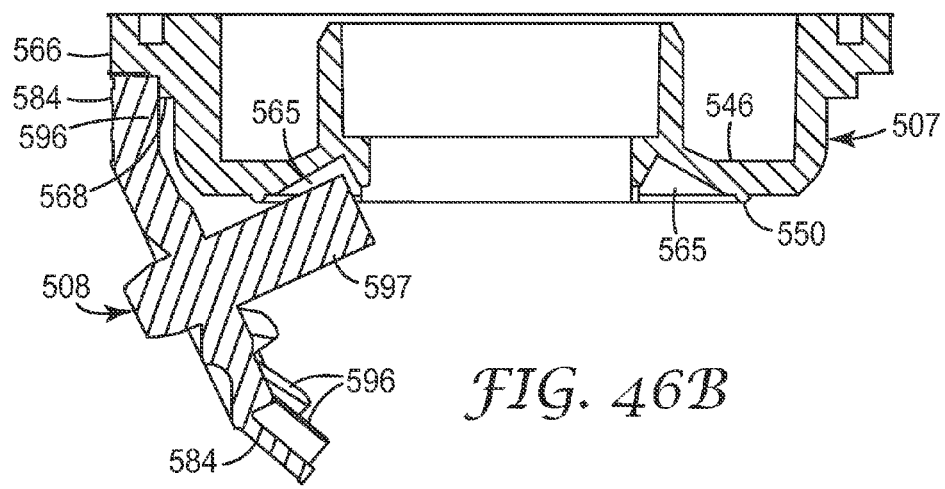
Figure 46C:
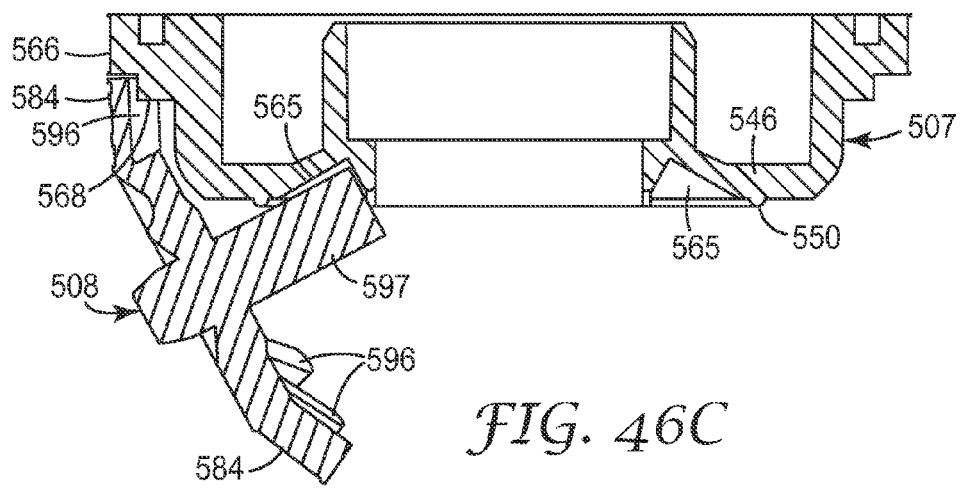

FIGS. 46A and 46B correspond to the position of the tens cone 508 when one of the teardrop shaped recesses 539 thereof is in mated engagement with the teardrop shaped protrusion 553 of the conical housing section 583 (as also shown in FIG. 45B). FIG. 46C illustrates the off-axis movement of the tens cone 508 relative to the units rotational ring 507 (which is allowed by the recessed region 565 thereof), when none of the teardrop shaped recesses 539 on the tens cone 508 are in mated engagement with the teardrop shaped protrusion 553 of the conical housing section 583 (as also shown in FIG. 45A).

Eventually, the in-fill element 545 on the tens cone 508 is rotated into abutment with the ramp 555 on the housing 509. Following this point of abutment (when the units rotational ring is showing a 9 as its ones units digit), as the units rotational ring 508 completes its last ten ones units counts, the protruding oblong lug 568 can no longer move a radial spoke 596 on the tens cone 508. Thus, the units rotational ring 507 will also be unable to advance beyond 0 as its ones units digit, once the tens cone 508 has reached 0 as its tens units numeral, despite further actuations of the inhaler.

In essence, the inventive dose counter 502 in the embodiment illustrated in FIGS. 41-47 operates in the following fashion. When a user actuates the inhaler by pushing the aerosol container downwardly into the actuator housing, the valve ferrule engages the indexer 504 to push it downwardly. Indexer 504 engages and then causes rotation of the units teeth ring 505. The units rotational ring 507 is coupled rotationally to the units teeth ring 505, so it rotates as well. As the aerosol container reciprocates down and up to complete a single dosage of medication therein, the indexer 504 and the units teeth ring 505 also reciprocate down and up relative to the units rotational ring 507. When complete up and down reciprocal movement of the units teeth ring 505 causes the units rotational ring 507 to rotate on its axis 522, the ring 507 has a single ones units count change in position thereof. Rotation of the units rotational ring 507 is translated into rotation of the tens cone 508 upon engagement of the lug 568 on the units rotational ring 507 with one of the spokes 596 on the tens cone 508. However, the tens cone 508 is only rotated periodically relative to the units rotational ring 507, to indicate a change in decade of the counts (i.e., the tens cone 508 is only moved once for every ten movements of the units ring 507). Each time the units rotational ring 507 counts ten ones units counts, the tens cone 508 is indexed one position to change the tens units counts displayed thereon.

In each embodiment, those portions of the components of the dose counter that are designed for engagement (e.g., sawtooth protrusions on an indexer and inner ring of teeth on a units teeth ring, circumferential rim or oblong lug on a units rotational ring and pegs or spokes on a tens cone) are formed from materials (e.g., suitable polymers) that are durable but of adequately low friction to facilitate ready interaction.

Although the present invention has been described with reference to preferred embodiments, workers skilled in the art will recognize that changes may be made in form and detail without departing from the spirit and scope of the invention.

The invention claimed is:
1. A dose counter comprising;
a lid, an indexer, a units teeth ring, a compression spring, a units rotational ring, a tens cone and a housing, wherein:
the lid has a fixed ratchet member,
the indexer is constructed and arranged to undergo a reciprocal movement coordinated with the reciprocal movement between an actuator and an aerosol container, said reciprocal movement comprising an outward stroke and a return stroke,
the housing comprising a cylindrical body and adapted to mate with interior surfaces of the actuator housing for the aerosol container, and being provided with a ledge to align with the units rotational ring, a cone-shaped lower rear recess to accommodate the tens cone for rotation about a first axis directed diagonally forward and upward from a rear corner of the recess, and a top rim with a plurality of slots to snap fit with projections on the lid,
the units teeth ring is constructed to undergo a predetermined counting movement each time a dose is dispensed, the units teeth ring being biased in the same direction towards the ratchet and the indexer by the compression spring and being capable of counting motion in a direction generally orthogonal to the direction of reciprocal movement of the indexer and about a second axis, the units teeth comprising a first region for interaction with the indexer which comprises at least one inclined surface which is engaged by the indexer during its outward stroke causing the units teeth ring to undergo counting motion, a second region for interaction with the ratchet member which comprises at least one inclined surface which is engaged by the ratchet member during the return stroke of the indexer causing the units teeth ring to undergo further counting motion to complete said predetermined counting movement,
the units rotational ring and the units teeth ring having keyed features therebetween constructed to allow relative axial movement therewith while being coupled for rotational motion about said second axis, the units rotational ring bearing indicia on its outer circumferential surface.

2. A dose counter according to claim 1 wherein the housing comprises two forward wings projecting outwardly and two forward legs projecting downwardly from the cylindrical body.

3. A dose counter according to claim 1 wherein the housing comprises a viewing window in the cylindrical body.

4. A dose counter according to claim 3 wherein portions of the tens cone and of the units rotational ring converge adjacent the viewing window.

5. A dose counter according to claim 4 wherein a circumferential segment of the units rotational ring and an arcuate segment of the tens cone are aligned to collectively present at least a portion of a medication dosage count at the viewing window.

6. A dose counter according to claim 1 wherein the indexer has a plurality of castellations and the lid has corresponding slots such that the castellations fit slideably through the slots.

7. A dose counter according to claim 1 wherein the units teeth ring comprises an outer ring of teeth for engagement with the fixed ratchet member.

8. A dose counter according to claim 7 wherein the outer ring of teeth comprises a gap in the teeth.

9. A dose counter according to claim 1 wherein the units teeth ring comprises an inner ring of teeth for engagement with teeth on the indexer.

10. A dose counter according to claim 1 wherein the keyed features comprise a plurality of axially aligned grooves on the units teeth ring and a plurality of axially aligned ribs on the units rotational ring.

11. A dose counter according to claim 1 wherein the units rotational ring has a plurality of oblong lugs, each spaced below and between each space between a 0 digit and its adjacent 9 digit.

12. A dose counter according to claim 11 wherein the units rotational ring comprises two oblong lugs.

13. A dose counter according to claim 12 wherein the tens cone comprises radial spokes each spoke configured and arranged to be engaged by an oblong lug to rotate the tens cone.

14. A dose counter according to claim 11 wherein the tens cone comprises radial spokes each spoke configured and arranged to be engaged by an oblong lug to rotate the tens cone.

15. A dose counter according to claim 1 wherein the compression spring is a leaf spring.

16. A dose counter according to claim 1 wherein the tens cone comprises thirteen numbers-bearing arcuate segments.

17. A method of assembly of a dose counter according to claim 1 wherein sequentially the tens cone, the units rotational ring, the compression spring, the units teeth ring and the indexer are inserted into the housing, and the lid is snap-fitted into place on the housing.

* * * * *

UNITED STATES PATENT AND TRADEMARK OFFICE
CERTIFICATE OF CORRECTION

| | |
|---|---|
| PATENT NO. | : 9,089,661 B2 |
| APPLICATION NO. | : 13/933148 |
| DATED | : July 28, 2015 |
| INVENTOR(S) | : Adam Stuart |

It is certified that error appears in the above-identified patent and that said Letters Patent is hereby corrected as shown below:

Drawings

<u>Sheet 30, Line 5, Figure 37A</u>
Delete "a" and insert -- $\alpha$ --, therefor.

<u>Sheet 30, Line 6, Figure 37B</u>
Delete "a" and insert -- $\alpha$ --, therefor.

<u>Sheet 34, Figure 42</u>
Delete "537" (labeling the annular array of teardrop shaped recesses), and insert -- 538 --, therefor.

Specification

<u>Page 21, Column 17</u>
Line 8, Delete "remaining" and insert -- remaining. -- therefor.

<u>Page 31, Column 24</u>
Line 65, Delete "a the" and insert -- the --, therefor.

<u>Page 34, Column 28</u>
Line 11, Delete "remaining)" and insert -- remaining). --, therefor.

<u>Page 36, Column 31</u>
Line 20, Delete "537" and insert -- 538 --, therefor.

<u>Page 36, column 31</u>
Line 62, Delete "$\beta_2$" and insert -- $\alpha_2$ --, therefor.

Signed and Sealed this
Fifth Day of April, 2016

Michelle K. Lee
*Director of the United States Patent and Trademark Office*